(12) United States Patent
Iwamiya et al.

(10) Patent No.: US 8,670,819 B2
(45) Date of Patent: Mar. 11, 2014

(54) OPTICAL BIOLOGICAL INFORMATION DETECTING APPARATUS AND OPTICAL BIOLOGICAL INFORMATION DETECTING METHOD

(75) Inventors: Hiroshi Iwamiya, Ome (JP); Shuji Nakajima, Kunitachi (JP)

(73) Assignee: Casio Computer Co., Ltd, Tokyo (JP)

( * ) Notice: Subject to any disclaimer, the term of this patent is extended or adjusted under 35 U.S.C. 154(b) by 567 days.

(21) Appl. No.: 12/825,601

(22) Filed: Jun. 29, 2010

(65) Prior Publication Data

US 2011/0004106 A1   Jan. 6, 2011

(30) Foreign Application Priority Data

| Jul. 1, 2009 | (JP) | 2009-156985 |
| Aug. 18, 2009 | (JP) | 2009-188987 |
| Dec. 22, 2009 | (JP) | 2009-291174 |
| Feb. 17, 2010 | (JP) | 2010-032088 |

(51) Int. Cl.
*A61B 6/00* (2006.01)

(52) U.S. Cl.
USPC .................................. 600/476; 606/9; 604/20

(58) Field of Classification Search
CPC .............................. A61B 1/227; A61B 5/1076
USPC .................................. 600/476; 606/9; 604/20
See application file for complete search history.

(56) References Cited

U.S. PATENT DOCUMENTS

| 7,733,224 B2* | 6/2010 | Tran ............................... 340/540 |
| 2005/0177140 A1* | 8/2005 | Jay ..................................... 606/9 |
| 2009/0198173 A1* | 8/2009 | Samuel et al. .................. 604/20 |
| 2010/0191125 A1* | 7/2010 | Foged et al. ................... 600/476 |

FOREIGN PATENT DOCUMENTS

| JP | 2000-116611 | 4/2000 |
| JP | 2001-353133 | 12/2001 |
| JP | 2004-337605 | 12/2004 |
| JP | 2008-237686 | 10/2008 |

OTHER PUBLICATIONS

Japanese Office Action for Application No. 2010-032088 mailed on Nov. 16, 2011.

* cited by examiner

*Primary Examiner* — Baisakhi Roy
(74) *Attorney, Agent, or Firm* — Turocy & Watson, LLP

(57) ABSTRACT

An optical biological information detecting apparatus includes a light emitting unit which emits observation light of a specific wavelength band to optically observe a desired portion of a tissue of a skin of a human body, and an annular light guide unit which guides the observation light to a desired area of a surface of the skin corresponding to the desired portion of the tissue of the skin, and which annularly irradiates the observation light onto the desired area of the surface of the skin. The apparatus further includes a light receiving unit which is disposed at a position surrounded by the annular light guide unit, and which receives scattered light scattered by the desired portion of the tissue of the skin after the observation light is annularly irradiated onto the desired area of the surface of the skin by the annular light guide unit.

9 Claims, 25 Drawing Sheets

| LIGHT EMISSION CONDITIONS OF INNER CIRCUMFERENTIAL SIDE LIGHT IRRADIATION PATH AND OUTER CIRCUMFERENTIAL SIDE LIGHT IRRADIATION PATH | | |
|---|---|---|
| LIGHT RECEIVING UNIT | LIGHT RECEPTION CONDITION 1 | LIGHT RECEPTION CONDITION 2 |
| INNER CIRCUMFERENTIAL SIDE LIGHT IRRADIATION PATH | ○ | × |
| OUTER CIRCUMFERENTIAL SIDE LIGHT IRRADIATION PATH | ○ | ○ |

○ : LIGHT EMISSION
× : LIGHT NON-EMISSION

FIG.28

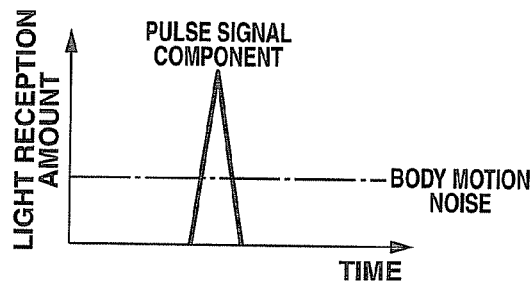

FIG.29A

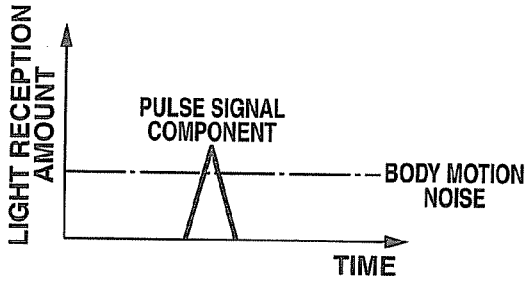

FIG.29B

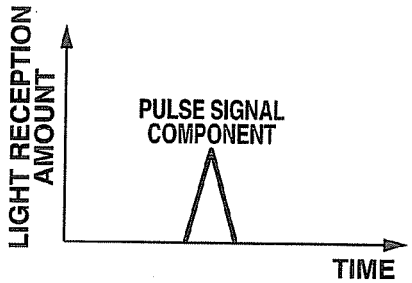

FIG.29C

OPTICAL BIOLOGICAL INFORMATION DETECTING APPARATUS AND OPTICAL BIOLOGICAL INFORMATION DETECTING METHOD

CROSS-REFERENCE TO RELATED APPLICATIONS

This application is based upon and claims the benefit of priority from prior Japanese Patent Applications No. 2009-156985, filed Jul. 1, 2009; No. 2009-188987, filed Aug. 18, 2009; No. 2009-291174, filed Dec. 22, 2009; and No. 2010-032088, filed Feb. 17, 2010, the entire contents of all of which are incorporated herein by reference.

BACKGROUND OF THE INVENTION

1. Field of the Invention

The present invention relates to an optical biological information detecting apparatus and an optical biological information detecting method that can optically detect biological information.

2. Description of the Related Art

As described in Japanese Patent Application KOKAI Publication No. 2001-353133, an optical biological information detecting apparatus combined with a wristwatch has been known.

An optical biological information detecting apparatus of a wristwatch type comprises a light emitting unit that emits observation light having a predetermined wavelength and a light receiving unit that receives scattered light of the observation light emitted from the light emitting unit and scattered in a biological tissue, which are provided on a back cover of the wristwatch. The optical biological information detecting apparatus causes the light emitting unit to intermittently emit light for a constant time with a constant period, causes the light receiving unit to receive the scattered light from the biological tissue according to pulsative light emission of the light emitting unit, performs photoelectric conversion, performs a frequency analysis on signals obtained by continuous observation for a predetermined time, and estimates biological information, such as a pulse wave.

The outline of an operational principle of the biological information detecting apparatus is as described above. However, according to the operational principle, absorbance where hemoglobin of blood absorbs light greatly changes at about 600 nanometers (hereinafter, simply referred to as nm), and the absorbance is very high at a wavelength shorter than 600 nm, as compared with a wavelength of 600 nm or more. For this reason, light having the wavelength shorter than 600 nm is generally used as the observation light emitted from the light emitting unit.

However, the biological information detecting apparatus according to the related art uses dermis including a blood capillary in a surface of a skin and epidermis containing melanine pigment of the surface side as an observation object of a pulse wave. However, if a large amount of melanine pigment is contained in the epidermis, the observation light may be absorbed by the melanine pigment. As a result, biological information, such as a pulse wave, cannot be accurately detected.

That is, the melanine pigment has extraordinarily high absorbance in a wavelength band from ultraviolet light to visible light. When the large amount of melanine pigment is contained in the epidermis (for example, in the case of a person of a dark skin color), even though observation light having a wavelength of 600 nm or less is irradiated onto the skin, the observation light that reaches the dermis including the blood capillary, repeats scattering and absorption in a dermis tissue, passes through the epidermis again, and arrives at the light receiving unit is weak light and cannot be sufficiently received. Therefore, biological information, such as a pulse wave, cannot be detected.

The biological information detecting apparatus according to the related art is configured such that the light emitting unit and the light receiving unit are two-dimensionally disposed on an observation light taking plate, light emitted from the light emitting unit is irradiated onto the skin through the observation light taking plate facing the surface of the skin, scattered light thereof is taken by the observation light taking plate, and the scattered light is received by the light receiving unit through the observation light taking plate. When the light emitted from the light emitting unit is incident in the skin from the observation light taking plate, a portion of the light may be reflected on an inner surface of the observation light taking plate, and the light reflected on the inner surface of the observation light taking plate may be received by the light receiving unit as light noise. As a result, only the scattered light from the skin cannot be accurately detected.

BRIEF SUMMARY OF THE INVENTION

Accordingly, it is an object of the present invention to provide an optical biological information detecting apparatus and an optical biological information detecting method that can efficiently and stably receive scattered light returned from a skin among observation light irradiated onto the skin and accurately and easily detect biological information.

In order to achieve the above described object, an optical biological information detecting apparatus according to one aspect of the present invention, comprises: a light emitting unit which emits observation light of a specific wavelength band to optically observe a desired portion of a tissue of a skin of a human body; an annular light guide unit which guides the observation light to a desired area of a surface of the skin corresponding to the desired portion of the tissue of the skin, and which annularly irradiates the observation light onto the desired area of the surface of the skin; and a light receiving unit which is disposed at a position surrounded by the annular light guide unit, and which receives scattered light scattered by the desired portion of the tissue of the skin after the observation light is annularly irradiated onto the desired area of the surface of the skin by the annular light guide unit.

An optical biological information detecting method according to one aspect of the present invention in order to achieve the above described object, is used in an optical biological information detecting apparatus, the optical biological information detecting apparatus comprising: a light emitting unit which emits observation light of a specific wavelength band to optically observe a desired portion of a tissue of a skin of a human body; an annular light guide unit which guides the observation light to a desired area of a surface of the skin corresponding to the desired portion of the tissue of the skin, and which annularly irradiates the observation light onto the desired area of the surface of the skin; and a light receiving unit which is disposed at a position surrounded by the annular light guide unit, and which receives scattered light scattered by the desired portion of the tissue of the skin after the observation light is annularly irradiated onto the desired area of the surface of the skin by the annular light guide unit.

And, the optical biological information detecting method according to the one aspect of the present invention comprises: causing the light emitting unit to emit observation light; annularly irradiating the observation light emitted from the light emitting unit onto the desired area of the surface of the skin by the light guide unit; receiving the scattered light after the irradiated observation light is scattered by the desired portion of the skin tissue, by the light receiving unit through the scattered light taking unit; and detecting biological information of the desired portion of the skin tissue, based on the scattered light received by the light receiving unit.

An optical biological information detecting method according to another aspect of the present invention in order to achieve the above described object, is used in an optical biological information detecting apparatus, the optical biological information detecting apparatus comprising: first and second light emitting portions each of which emit observation light of a specific wavelength band to optically observe a desired portion of a tissue of a skin of a human body; first and second light guiding ring portions which are mutually concentrically disposed, which guide the observation lights emitted from the first and second light emitting portions to desired area of a surface of the skin corresponding to the desired portion of the tissue of the skin, and which annularly irradiate the observation lights onto the desired area of the surface of the skin; a scattered light taking unit which is disposed at a position surrounded by the first and second light guiding ring portions, which contacts the desired area of the surface of the skin, and which takes scattered lights after the observation lights annularly irradiated onto the desired area of the surface of the skin by the first and second light guiding ring portions are scattered by the desired portion of the tissue of the skin; and a light receiving unit which is positioned at a side of the scattered light taking unit which is opposite to the surface of the skin and which receives the scattered lights through the scattered light taking unit.

And, the optical biological information detecting method comprises: causing the first and second light emitting portions to simultaneously emit the observation lights, guiding the observation lights emitted from the first and second light emitting portions to the desired area of the surface of the skin corresponding to the desired portion of the tissue of the skin by the first and second light guiding ring portions, annularly irradiating the observation lights onto the desired area of the surface of the skin, receiving the scattered lights after the irradiated observation lights are scattered by the desired portion of the tissue of the skin by the light receiving unit through the scattered light taking unit, and detecting first biological information of the desired portion of the skin tissue, based on the scattered lights received by the light receiving unit; causing only the first light emitting portion to emit the observation light, guiding the observation light emitted from the first light emitting portion to the desired area of the surface of the skin corresponding to the desired portion of the tissue of the skin by the first light guiding ring portion, annularly irradiating the observation light onto the desired area of the surface of the skin, receiving the scattered light after the irradiated observation light is scattered by the desired portion of the tissue of the skin by the light receiving unit through the scattered light taking unit, and detecting second biological information of the desired portion of the skin tissue, based on the scattered light received by the light receiving unit; and processing the first biological information and the second biological information and calculating biological information unique to the human body where the observation lights are irradiated.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 28 is a table illustrating light emission conditions of an outer circumferential side light irradiation path and an inner circumference side light irradiation path in the optical biological information detecting apparatus of FIG. 27;

FIG. 29A is a diagram illustrating a state where biological information, such as a pulse wave, is detected by the optical biological information detecting apparatus of FIG. 27, and illustrating a pulse wave signal when both the first and second light emitting portions are made to simultaneously emit light as shown in FIG. 24;

FIG. 29B is a diagram illustrating a state where biological information, such as a pulse wave, is detected by the optical biological information detecting apparatus of FIG. 27, and illustrating a pulse wave signal when only the first light emitting portion is made to emit light as shown in FIG. 25;

FIG. 29C is a diagram illustrating a state where biological information, such as a pulse wave, is measured by the optical biological information detecting apparatus of FIG. 27, and illustrating an estimated pulse wave signal when the biological information, such as the pulse wave, is optically detected as shown in FIG. 26;

DETAILED DESCRIPTION OF THE INVENTION

First Embodiment

Hereinafter, a first embodiment where the invention is applied to a wristwatch will be described with reference to FIGS. 1 to 10 and 30.

Figure 1:
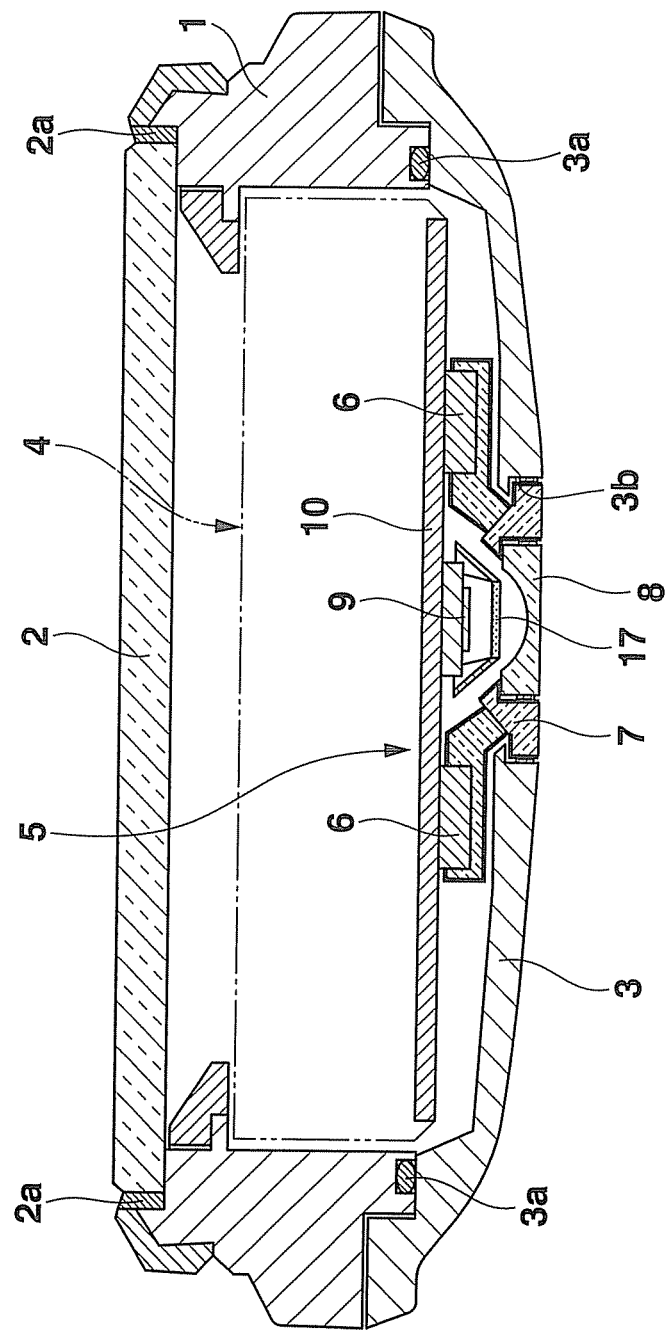
FIG. 1 is a schematic longitudinal cross-sectional view of a body case of a wristwatch where an optical biological information detecting apparatus according to a first embodiment of the present invention is combined.

As illustrated in FIG. 1, the wristwatch comprises a wristwatch case 1. In an upper opening of the wristwatch case 1, a watch glass 2 is mounted through a packing 2a. Below the wristwatch case 1, a back cover 3 is mounted through a waterproof ring 3a. In the wristwatch case 1, a time piece module 4 that has various components needed for a watch function is disposed.

Figure 2:
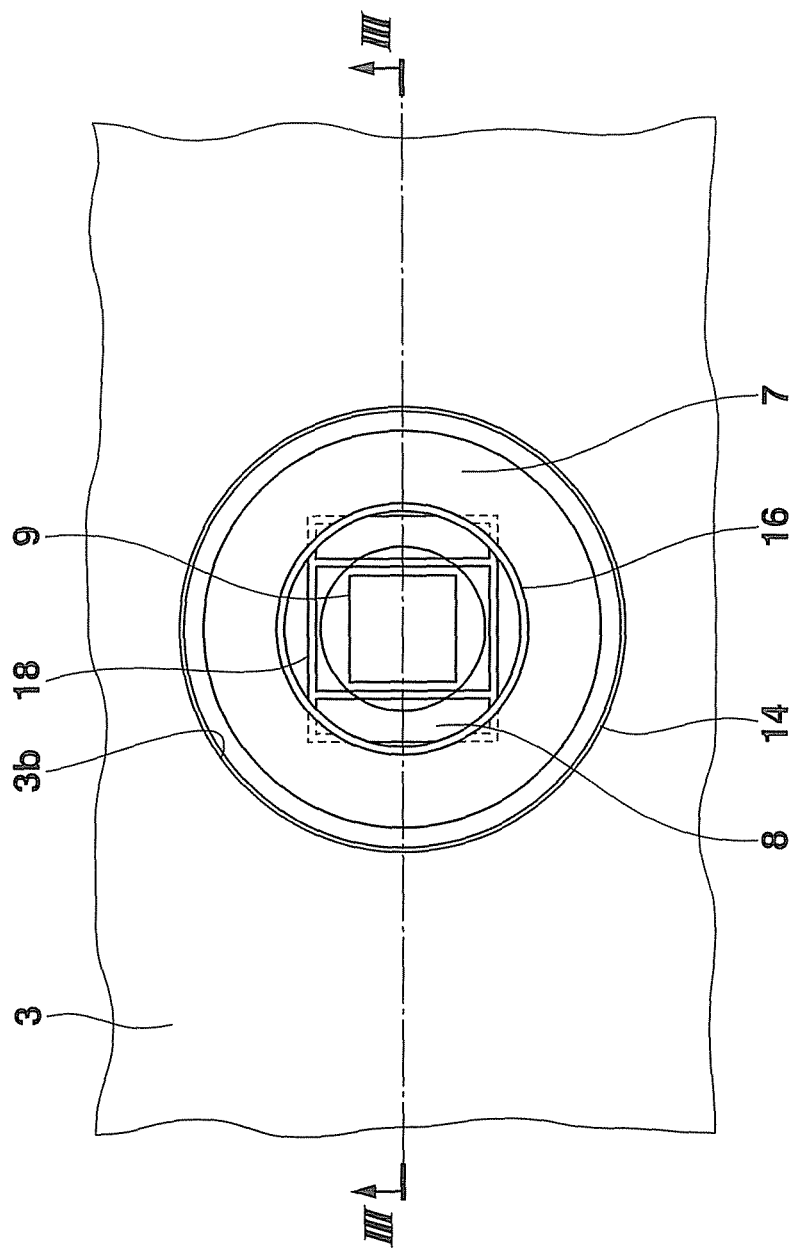
FIG. 2 is a plan view of a main portion of a back cover of the wristwatch of FIG. 1.
Figure 3:
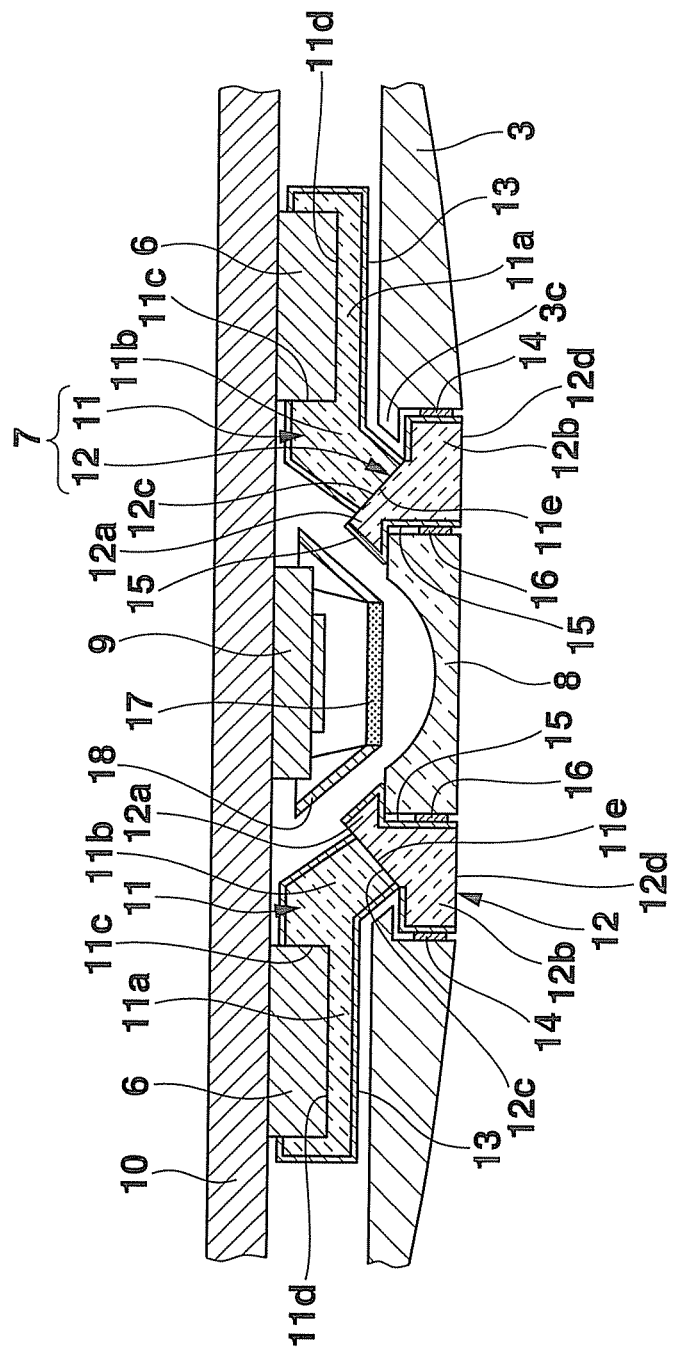
FIG. 3 is a cross-sectional view taken along a line III-III in FIG. 2.
Figure 4:
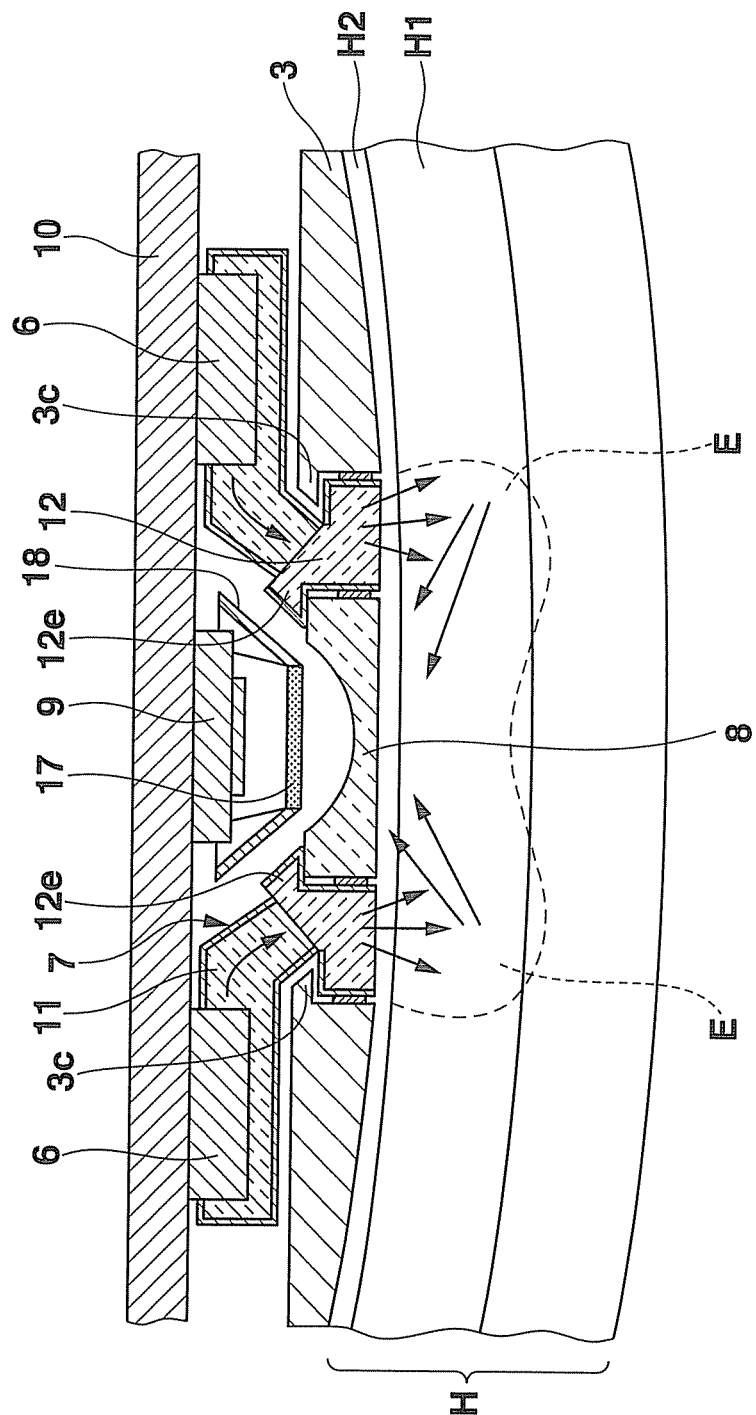
FIG. 4 is an enlarged cross-sectional view illustrating a state where biological information, such as a pulse wave, is detected while the back cover of the wristwatch illustrated in FIG. 1 contacts the skin of an arm.
Figure 5:
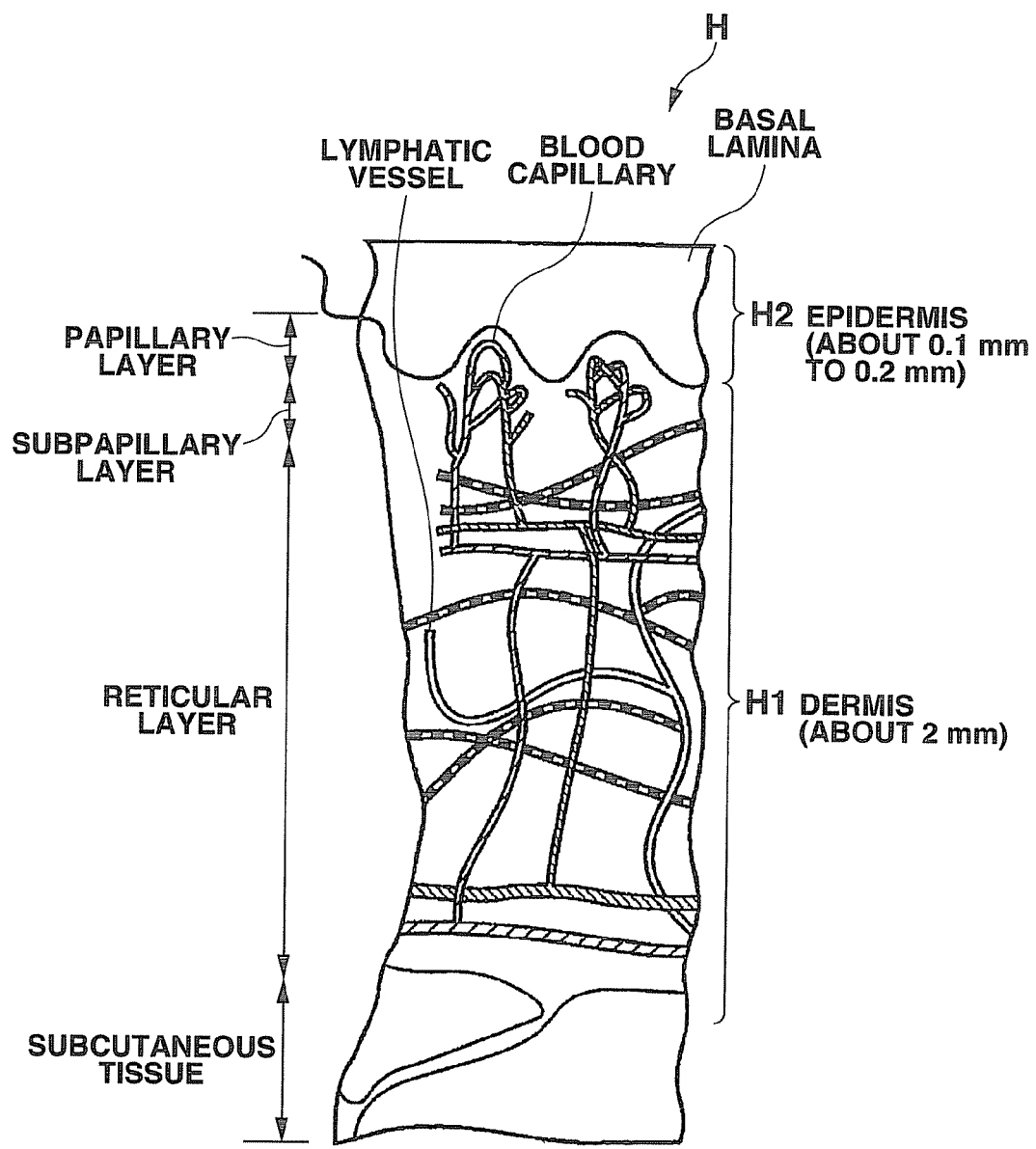
FIG. 5 is a schematic enlarged cross-sectional view of a tissue of the skin illustrated in FIG. 4.
Figure 6:
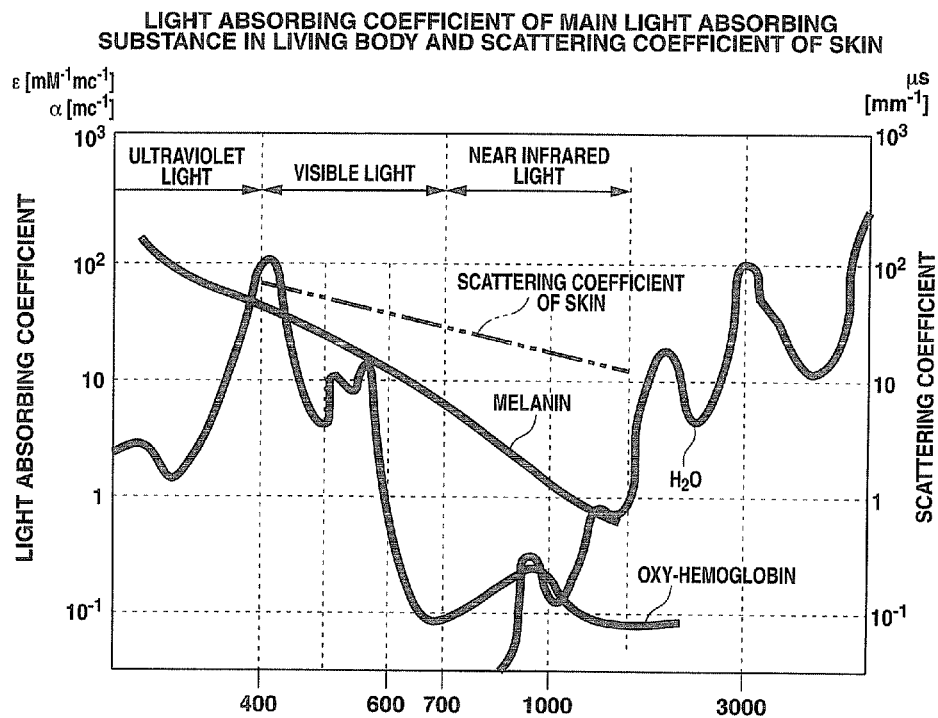
FIG. 6 is a diagram illustrating a relationship between a scattering characteristic and a light absorbing characteristic of a main light absorbing substance of a biological tissue in the skin illustrated in FIG. 5.
Figure 7:
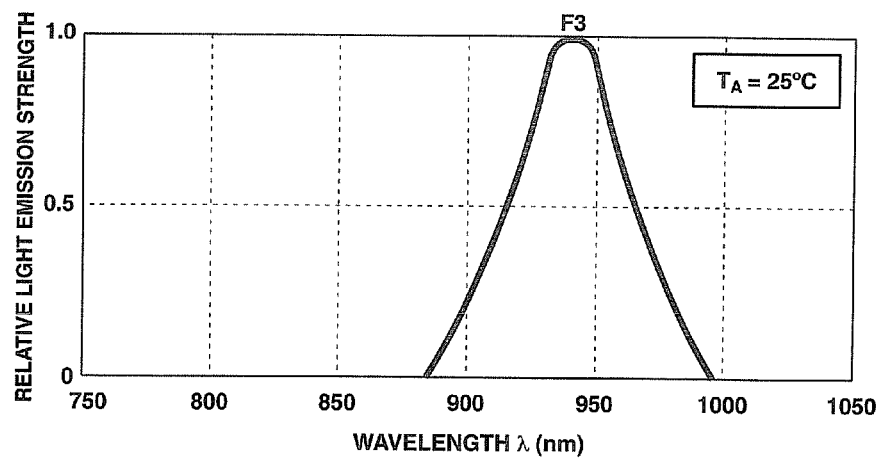
FIG. 7 is a diagram illustrating a relative light emission strength characteristic in observation light of an infrared band emitted by a light emitting unit illustrated in FIG. 4.

In a central portion of the back cover 3 of the wristwatch case 1, a biological information detecting apparatus 5 is provided, as illustrated in FIGS. 1 to 3. In this case, the back cover 3 is formed of a metal, such as stainless steel. As illustrated in FIGS. 3 and 4, a bottom surface of the back cover 3 protrudes to the lower side while being moderately curved toward the central portion, and a mounting hole 3b used to mount the biological information detecting apparatus 5 is provided in the protruded central portion to penetrate the central portion up and down.

As illustrated in FIGS. 3 and 4, the biological information detecting apparatus 5 comprises light emitting units 6 that emit observation light of a specific wavelength band to optically observe a skin tissue of a human body, an annular light guide unit 7 that guides the observation light emitted from the light emitting units 6 and annularly diffuses and irradiates the observation light with respect to a skin H, a scattered light taking unit 8 that contacts the skin H positioned in a central portion of an annular irradiation area E where the observation light is irradiated by the annular light guide unit 7, and a light receiving unit 9 that is disposed in a place positioned at the side opposite to the skin H in the scattered light taking unit 8 and receives scattered light of the observation light taken by the scattered light taking unit 8.

In this case, the light emitting unit 6 and the light receiving unit 9 are provided on a bottom surface of a circuit board 10 for measurement, as illustrated in FIGS. 1 to 4. The circuit board 10 is positioned on the light guide unit 7 and is disposed in the wristwatch case 1. The light guide unit 7 is mounted in the back case 3 in a state where its lower side is fitted into the mounting hole 3b of the back cover 3 and its upper side is disposed on an inner surface (top surface in FIG. 1) of the back cover 3.

Meanwhile, the light emitting unit 6 is composed of a light emitting diode (LED) and is configured to emit infrared light ($\lambda p=940$ nm) where absorbance of melanine pigment contained in the skin H is low as the observation light. As illustrated in FIGS. 3 and 4, the light emitting units 6 are provided in two places of the 3 o'clock side and the 9 o'clock side in a bottom surface of the circuit board 10 corresponding to the light guide unit 7, respectively.

The light guide unit 7 comprises a light guiding ring portion 11 and a diffusion/irradiation ring portion 12, as illustrated in FIGS. 3 and 4. The light guiding ring portion 11 is formed in almost a ring shape, using a material such as transparent glass or a transparent resin with a high light transmitting property. The light guiding ring portion 11 has the configuration where a flat ring portion 11a and an inclined ring portion 11b that is inclined to the oblique lower side toward the central side of the ring portion 11a from an inner circumferential surface thereof are integrally formed. In the places of the 3 o'clock side and the 9 o'clock side of the top surface in the flat ring portion 11a, concave portions 11c where the light emitting units 6 are disposed are provided.

Thereby, as illustrated in FIG. 4, the light guiding ring portion 11 is configured such that an inner surface of each concave portion 11c in the flat ring portion 11a is formed in an incident surface 11d, the observation light emitted from the incident surface 11d by the light emitting unit 6 is taken in the flat ring portion 11a, and the taken observation light is emitted from an emission surface 11e formed in a lower front end of the inclined ring portion 11b while being annularly guided by the flat ring portion 11a.

In this case, as illustrated in FIGS. 3 and 4, on an external surface of the light guiding ring portion 11, a first reflection layer 13 is provided by a metal vapor deposition method, except for the incident surface 11d of the flat ring portion 11a and the emission surface 11e of the inclined ring portion 11b. The first reflection layer 13 prevents the observation light, which is incident in the inner portion of the light guiding ring portion 11, from leaking to the outside of the light guiding ring portion 11.

As illustrated in FIGS. 3 and 4, the diffusion/irradiation ring portion 12 is formed in almost a ring shape, using a clouded or milky resin with a light diffusing property. The diffusion/irradiation ring portion 12 has the configuration where an inclined ring portion 12a corresponding to the emission surface 11e of the inclined ring portion 11b of the light guiding ring portion 11 and a ring portion 12b with almost a flat shape that is provided on the lower side of the inclined ring portion 12a and has a bottom surface formed to be flat are integrally formed.

Thereby, the diffusion/irradiation ring portion 12 is configured to take the observation light discharged from the emission surface 11e of the inclined ring portion 11b of the light guiding ring portion 11 in the inner portion of the incident surface 12c of the inclined ring portion 12a, annularly guide the taken observation light while diffusing the observation light by the inclined ring portion 12a, diffuse and discharge the observation light from the emission surface 12d of the bottom surface in the flat ring portion 12b, and uniformly diffuse and irradiate the observation light over a wide area of a ring shape with respect to the skin H.

In this case, as illustrated in FIGS. 3 and 4, the diffusion/irradiation ring portion 12 is mounted in a state where the flat ring portion 12b thereof is fitted into the mounting hole 3b provided in the central portion of the back cover 3 through a first waterproof packing 14. At this time, the position of the diffusion/irradiation ring portion 12 is regulated such that the diffusion/irradiation ring portion comes into contact with a protrusion portion 3c provided in the mounting hole 3b of the back cover 3 and is not pressed into the wristwatch case 1, as illustrated in FIG. 4.

Thereby, as illustrated in FIGS. 3 and 4, the bottom surface of the diffusion/irradiation ring portion 12, that is, the emission surface 12d of the bottom surface in the flat ring portion 12b is disposed at the same height as that of a lowermost portion in the bottom surface of the back cover 3 and contacts the skin H together with the bottom surface of the back cover 3. As illustrated in FIGS. 3 and 4, on an external surface of the diffusion/irradiation ring portion 12, a second reflection layer 15 is provided by a metal vapor deposition method, except for the incident surface 12c of the inclined ring portion 12a and the emission surface 12d of the flat ring portion 12b. The second reflection layer 15 prevents the observation light, which is incident in the inner portion of the diffusion/irradiation ring portion 12, from leaking to the outside of the diffusion/irradiation ring portion 12.

As illustrated in FIGS. 3 and 4, in the diffusion/irradiation ring portion 12, a scattered light taking unit 8 that takes the scattered light of the observation light irradiated onto the skin H is provided. The scattered light taking unit 8 is formed of a material, such as transparent glass or a transparent resin with a high refractive index. The scattered light taking unit 8 is formed in a shape of a concave lens to increase light reception sensitivity of an outer circumferential portion of the scattered light taking unit 8 of the light receiving unit 9 disposed on the side opposite to the skin H, with respect to the scattered light of the observation light incident in the skin H, scattered, and returned to the scattered light taking unit 8. The scattered light taking unit 8 is configured to contact the skin H positioned in a central portion of an irradiation area E having a ring shape where a bottom surface is irradiated with the observation light by the light guide unit 7.

In this case, as illustrated in FIG. 4, the position of the scattered light taking unit 8 is regulated such that the scattered light taking unit comes into contact with the protrusion portion 12e provided in an inner circumferential surface in the diffusion/irradiation ring portion 12 of the light guide unit 7 and is not pressed into the wristwatch case 1. Thereby, as illustrated in FIGS. 3 and 4, in the scattered light taking unit 8, the bottom surface that contacts the skin H is formed in a shape of a plano-concave lens. A flat surface of the bottom surface of the scattered light taking unit 8 forms the same plane as the bottom surface of the diffusion/irradiation ring portion 12 of the light guide unit 7 and is mounted in an inner circumferential surface of the diffusion/irradiation ring portion 12 of the light guide unit 7 through a second waterproof packing 16 in this state.

An outer circumferential surface of the scattered light taking unit 8 and an inner circumferential surface of the diffusion/irradiation ring portion 12 of the light guide unit 7 are optically isolated by the second reflection layer 15 formed in the inner circumferential surface of the diffusion/irradiation ring portion 12, as illustrated in FIG. 3.

Meanwhile, the light receiving unit 9 receives the scattered light of the observation light that is taken by the scattered light taking unit 8 and performs photoelectric conversion, and is composed of a silicon photo diode. As illustrated in FIGS. 3 and 4, the light receiving unit 9 is preferably disposed in a place positioned at the side (upper side in FIG. 3) opposite to the skin H in the scattered light taking unit 8, that is, in the vicinity of the focal position on an optical axis of the scattered light taking unit 8.

Figure 9:
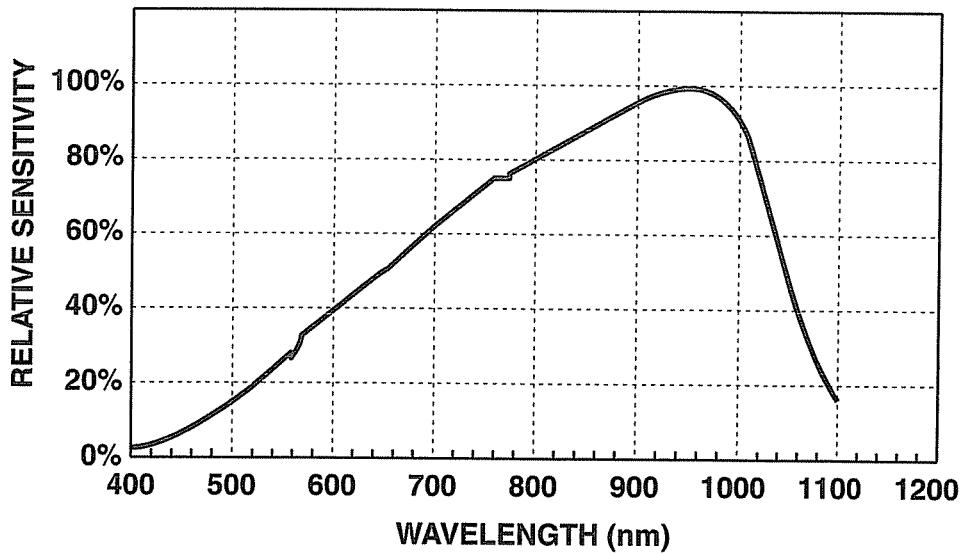
FIG. 9 is a diagram illustrating a spectral sensitivity characteristic of a light receiving unit illustrated in FIG. 4.

As illustrated in FIG. 9, the light receiving unit 9 has a spectral sensitivity characteristic of reacting strongest with light of a specific wavelength band of about $\lambda=940$ nm. That is, the light receiving unit 9 is configured such that light reception sensitivity is gradually lowered as the wavelength becomes short with respect to light of a wavelength band of 940 nm or less, is rapidly lowered with respect to light of a wavelength band of 940 nm or more, and becomes highest with respect to light having a wavelength of 940 nm.

Figure 8:
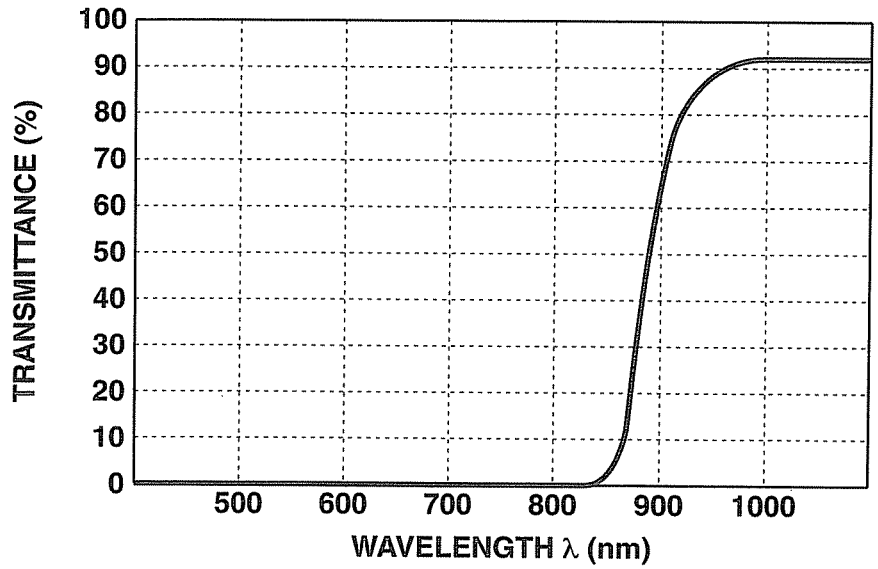
FIG. 8 is a diagram illustrating a spectral characteristic by transmittance of an optical filter illustrated in FIG. 4.

As illustrated in FIGS. 3 and 4, between the light receiving unit 9 and the scattered light taking unit 8, an optical filter 17 is disposed in a state where the optical filter is mounted on the lower side of a light shielding frame 18 to surround the light receiving unit 9. As illustrated in FIG. 8, the optical filter 17 is configured to transmit light of a specific wavelength band of 900 nm or more and shield light of a wavelength band of 900 nm or less, such that the light receiving unit 9 alleviates an influence from a measurement change due to external light, such as sunlight.

Thereby, when the scattered observation light that arrives at dermis H1 including a blood capillary in the skin H transmits epidermis H2 and is condensed by the scattered light taking unit 8, the optical filter 17 intercepts light of a wavelength band of less than 900 nm and transmits light of a wavelength band of 900 nm or more, and the light receiving unit 9 alleviates the influence from the measurement change due to the external light, receives only the light of the specific wavelength band transmitted through the optical filter 17, and performs photoelectric conversion.

Figure 10:
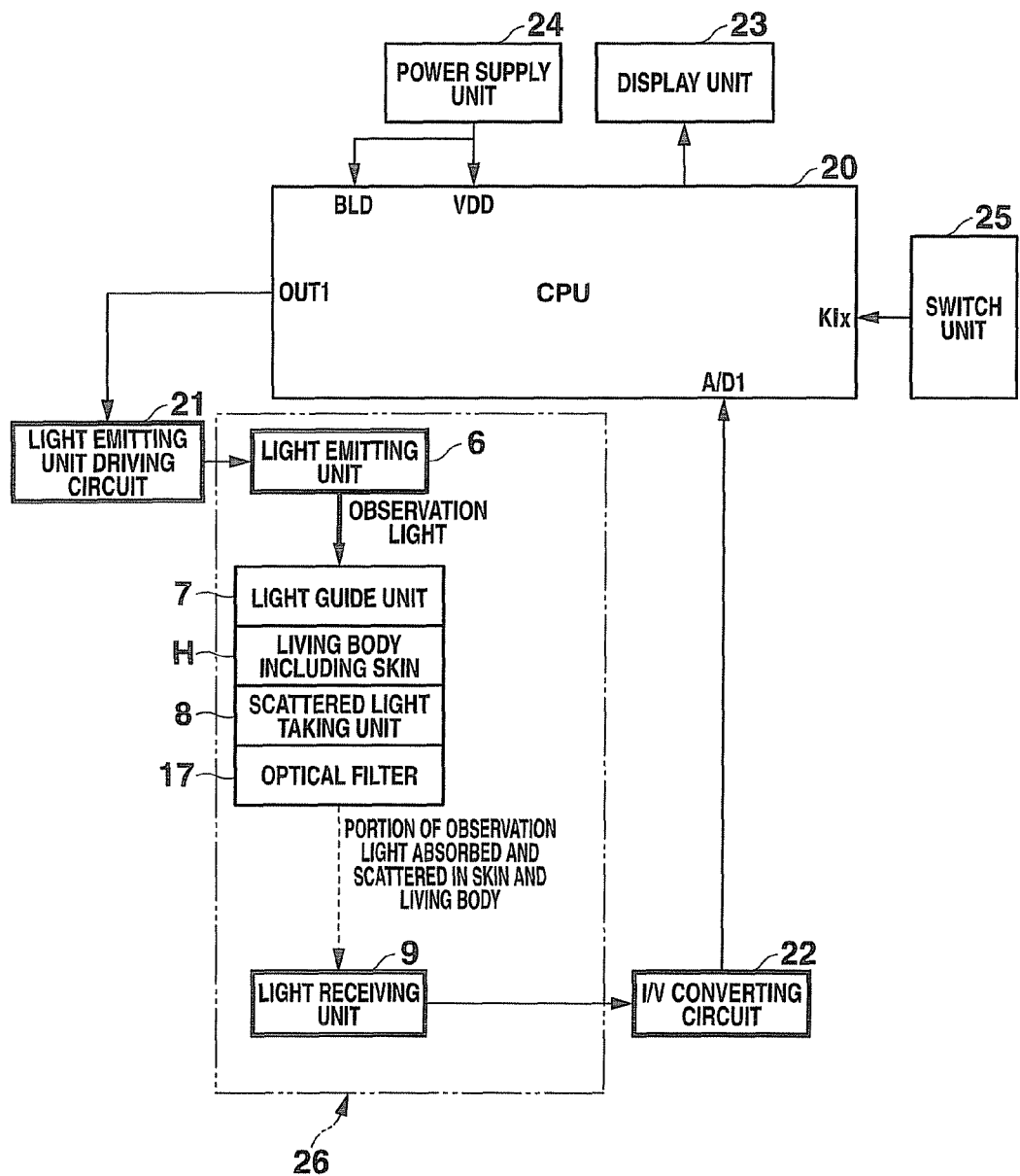
FIG. 10 is a block diagram illustrating a configuration of a circuit of the optical biological information detecting apparatus according to the first embodiment of the present invention.

Next, the circuit configuration of the biological information detecting apparatus 5 will be described with reference to a block diagram illustrated in FIG. 10.

The circuit configuration of the biological information detecting apparatus 5 comprises a CPU (central processing unit) 20 that performs whole control of the apparatus, a photoelectric signal detecting module 26 comprising the light emitting unit 6 and the light receiving unit 9, a light emitting unit driving circuit 21 that drives the light emitting unit 6 of the photoelectric signal detecting module 26, an I/V converting circuit 22 that converts a current signal output from the light receiving unit 9 of the photoelectric signal detecting module 26 into a voltage signal, a display unit 23 that displays a measurement result of biological information, such as a pulse wave, a power supply unit 24 that supplies a power supply voltage to the individual units, and a switch unit 25 that is operated by a user.

The CPU 20 is a large scale integrated circuit (LSI). The photoelectric signal detecting module 26 comprises the light emitting unit 6 that emits the observation light of a specific wavelength band and the light receiving unit 9 that receives the scattered light of the observation light, when the observation light emitted from the light emitting unit 6 is irradiated onto the skin H and is scattered in the skin H, and outputs a current signal according to the amount of received light. The power supply unit 24 supplies power to the CPU 20, the light emitting unit driving circuit 21, and the I/V converting circuit 22, and the supply of power to the circuit block other than the CPU 20 is controlled by the CPU 20. The two light emitting units 6 disposed in the two places of the 3 o'clock side and the 9 o'clock side are connected in series.

If the operation signal from the switch unit 25 is input from a KIx port, the CPU 20 outputs a driving signal to the light emitting unit driving circuit 21 from an OUT1 port, continuously controls driving of the light emitting unit 6 with a constant voltage pulse for a constant time with a constant period, and emits light from the light emitting, unit 6 with constant light intensity. If the observation light emitted from the light emitting unit 6 is irradiated onto the skin H and the scattered light thereof is received by the light receiving unit 9, the light receiving unit 9 outputs a current signal according to the amount of received light. The I/V converting circuit 22 converts the current signal output from the light receiving unit 9 into a voltage signal and inputs the signal to an A/D1 port of the CPU 20.

The CPU 20 converts the voltage signal, which is input to the A/D1 port, into a digital signal by an incorporated A/D converter at predetermined timing of the constant current pulse during a driving period and stores the signal as time-series data in an incorporated memory. The CPU 20 performs a frequency analysis on the time-series data, outputs the data as biological information such as a pulse wave to the display unit 23, and displays the data on the display unit 23.

Next, a biological information detecting method in the biological information detecting apparatus 5 will be described with reference to FIG. 30.

The biological information detecting method comprises a light emitting step S31 of causing the CPU 20 to emit observation light from the light emitting unit 6, an irradiating step S32 of annularly irradiating the observation light emitted by the light emitting step S31 onto the skin H by the light guide unit 7, a light receiving step S33 of scattering the observation light irradiated by the irradiating step S32 in the skin H, taking the scattered light by the scattered light taking unit 8, and receiving the taken scattered light by the light receiving unit 9, and a biological information detecting step S34 of causing the CPU 20 to detect biological information, based on the scattered light received by the light receiving step S33.

Next, a function of the biological information detecting apparatus 5 will be described.

The wristwatch case 1 is previously mounted on the arm and the bottom surface of the back cover 3 is made to contact the skin H of the arm, as illustrated in FIG. 4. At this time, the bottom surface of the back cover 3 is moderately curved and protruded. However, the bottom surface of each of the diffusion/irradiation ring portion 12 of the light guide unit 7 and the scattered light taking unit 8 in the biological information detecting apparatus 5 is formed to become a flat surface, and the flat surfaces thereof are disposed on the same plane. Thereby, the flat surfaces of the diffusion/irradiation ring portion 12 and the scattered light taking unit 8 equally contact the surface of the skin H of the arm.

In this state, if a command that causes the switch unit 25 to be operated and start the measurement is given to the CPU 20, the CPU 20 outputs a driving signal to the light emitting unit driving circuit 2, which in turn continuously outputs a constant current pulse to the light emitting unit 6 for a constant time with a constant period, and controls the driving of the light emitting unit 6. While the driving of the light emitting unit 6 is controlled, the light emitting unit 6 stably emits the observation light with constant light intensity.

At this time, if the light emitting unit 6 is driven by the light emitting unit driving circuit 21, the light emitting unit 6 emits light of an infrared band of $\lambda p=940$ nm as the observation light. As illustrated in FIG. 4, the emitted observation light is taken in the light guiding ring portion 11 from the incident surface 11d of the light guiding ring portion 11 of the light guide unit 7, and the taken observation light is annularly discharged from the emission surface 11e of the light guiding ring portion 11 while annularly being guided by the light guiding ring portion 11.

The discharged observation light is annularly diffused and discharged from the emission surface 12d of the diffusion/irradiation ring portion 12 contacting the skin H while being incident in the diffusion/irradiation ring portion 12 of the light guide unit 7 from the incident surface 12c and being diffused, and the discharged observation light is uniformly irradiated onto the skin H of the arm over a wide range of a ring shape. As illustrated in FIG. 4, the irradiated observation light is incident in the epidermis H2 and the dermis H1 of the skin H.

At this time, even though the epidermis H2 contains the large amount of melanine pigment, the observation light is light of an infrared band of $\lambda p=940$ nm. For this reason, the amount of light absorbed by the melanine pigment is small and the light is securely incident in the dermis H1. Since the epidermis H2 has the layer thickness of about 0.1 to 0.2 mm, which is smaller than that of the dermis H1, most of the irradiated observation light transmits the epidermis H2 and is incident in the dermis H1 having the layer thickness of about 2 mm.

The observation light incident in the inner portion of the dermis H1 is uniformly irradiated over a wide area of a ring shape and the amount of hemoglobin that is a light absorbing substance in the dermis H1 in the irradiation area becomes large, as compared with the case where the observation light is spotlightingly irradiated onto a portion. Therefore, the large amount of observation light is absorbed in the dermis H1 and the amount of observation light that arrives at a subcutaneous tissue of the inner side (lower side in FIG. 5) of the dermis H1 decreases.

The observation light incident in the dermis H1 is absorbed and scattered by the biological tissue of the dermis H1, and a portion of the scattered light transmits the epidermis H2 again and is discharged from the surface of the epidermis H2. Even at this time, since the small amount of scattered light is absorbed by the melanine pigment, the scattered light securely transmits the epidermis H2 and is irradiated onto the scattered light taking unit 8.

Since the scattered light taking unit 8 is formed in a shape of a convex lens using a material having a high refractive index, the scattered light that is taken in the scattered light taking unit 8 among the scattered light scattered by the biological tissue in the dermis H1, and the scattered light that is taken from the outer circumferential portion of the scattered light taking unit 8 can be incident in the light receiving unit 9 disposed on the side opposite to the skin H, from a front direction. Among the scattered light, light of a specific wavelength band of 900 nm or more is selected by the optical filter 17, the selected light of the specific wavelength band transmits the optical filter 17, and the transmitted light of the specific wavelength band is received by the light receiving unit 9 and is subjected to photoelectric conversion.

The current signal subjected to the photoelectric conversion in the light receiving unit 9 is converted into a voltage signal by the I/V converting circuit 22, and the voltage signal is converted into a digital signal by the A/D converter of the CPU 20. The converted digital signal is stored in the incorporated memory as time-series data by the CPU 20, and the CPU 20 performs a frequency analysis based on the time-series data, estimates the signal as biological information such as a pulse wave, and displays the information on the display unit 23.

As such, according to the biological information detecting apparatus 5, if the observation light of the specific wavelength band of $\lambda p=940$ nm is emitted by the light emitting unit 6, the observation light can be annularly diffused and irradiated onto the skin H by the light guide unit 7. Therefore, the observation light can be uniformly irradiated over the wide range of the skin H, and the scattered light of the observation light that is scatted in the skin H can be taken by the scattered light taking unit 8 positioned in the central portion in the annular irradiation area E and can be received by the light receiving unit 9. As a result, the scattered light of the observation light can be efficiently and stably received by the light receiving unit 9.

For this reason, the observation light from the light emitting unit 6 can be uniformly irradiated over the wide range of the skin H, and the light irradiation path through which the observation light from the light emitting unit 6 is irradiated onto the skin H and the light reception path through which the scattered light of the observation light scattered in the skin H is received can be perfectly isolated from each other. Therefore, the scattered light of the observation light that is diffused in and irradiated onto the skin H can be efficiently and stably received by the light receiving unit 9. Thereby, biological information, such as a pulse wave, can be accurately detected.

In this case, since the light emitting unit 6 emits the infrared light of $\lambda p=940$ nm where absorbance of the melanine pigment contained in the epidermis H2 of the skin H is low as the observation light, even though the epidermis H2 contains the large amount of melanine pigment, the observation light irradiated onto the skin H can be securely incident in the dermis H1 without being absorbed by the melanine pigment. Since the epidermis H2 has the layer thickness smaller than that of the dermis H1, most of the observation light irradiated onto the skin H transmits the epidermis H2. Therefore, most of the observation light irradiated onto the skin H can be securely incident in the dermis H1.

The light guide unit 7 comprises the light guiding ring portion 11 that takes the observation light emitted from the light emitting unit 6 from the incident surface 11d, annularly guides the observation light, and annularly discharges the annularly guided observation light from the emission surface 11e and the diffusion/irradiation ring portion 12 that takes the observation light discharged from the emission surface 11e of the light guiding ring portion 11 from the incident surface 12c, diffuses the observation light from the emission surface 12d contacting the skin H, and annularly irradiates the observation light onto the skin H, and can efficiently and securely diffuse and irradiate the observation light emitted from the light emitting unit 6 in an annular shape, with respect to the skin H. Thereby, the observation light can be uniformly irradiated over the wide area of the skin H.

In this case, since the light guiding ring portion 11 is formed of a material with a high light transmitting property, the light guiding ring portion 11 can securely take the observation light emitted from the light emitting unit 6, efficiently guide the observation light in an annular shape, and annularly discharge the observation light from the emission surface 11e of the light guiding ring portion 11. Since the external surface of the light guiding ring portion 11 is provided with the first reflection layer 13, except for the incident surface 11d and the emission surface 11e of the light guiding ring portion 11, when the observation light emitted from the light emitting unit 6 is taken and annularly guided, the observation light can be securely and annularly discharged from the emission surface 11e of the light guiding ring portion 11 without leaking to the outside of the light guiding ring portion 11.

Since the diffusion/irradiation ring portion 12 is formed of a material with diffuseness that takes and diffuses the observation light discharged from the emission surface 11e of the light guiding ring portion 11, the taken observation light can be annularly guided while being efficiently diffused, the observation light can be annularly diffused in the skin H as the uniform irradiation light from the emission surface 12d of the diffusion/irradiation ring portion 12 and can be irradiated onto the skin H.

Even in this case, since the external surface of the diffusion/irradiation ring portion 12 is provided with the second reflection layer 15, except for the incident surface 12c and the emission surface 12d of the diffusion/irradiation ring portion 12, the observation light taken by the diffusion/irradiation ring portion 12 can be securely, efficiently and annularly diffused in the skin H as the uniform irradiation light from the emission surface 12d of the diffusion/irradiation ring portion 12 without leaking to the outside of the diffusion/irradiation ring portion 12 and can be irradiated onto the skin H.

As such, the observation light incident in the inner portion of the dermis H1 is uniformly irradiated over the wide area of the ring shape, as compared with the case where the observation light is spotlightingly irradiated onto the portion. Therefore, the amount of hemoglobin that is a light absorbing substance in the dermis H1 where the observation light is irradiated can be increased. Thereby, a change in the amount of hemoglobin in the biological tissue of the dermis H1 can be accurately detected.

That is, if the amount of hemoglobin that is the light absorbing substance in the dermis H1 increases, the large amount of observation light is absorbed in the dermis H1, the amount of observation light that arrives at the subcutaneous tissue of the lower side of the dermis H1 decreases, and the scattered light of the observation light from the subcutaneous tissue decreases. As a result, a change in the amount of hemoglobin generated in the biological tissue of the dermis H1 can be accurately detected.

The scattered light taking unit 8 is made of a material with a high refractive index and is formed in a shape of a concave lens to increase light reception sensitivity of an outer circumferential portion of the scattered light taking unit 8 in order to receive the scattered light of the observation light scattered in the biological tissue in the skin H by the light receiving unit 9 disposed on the side opposite to the skin H. Therefore, most of the scattered light of the observation light that is scattered in the biological tissue in the skin H and diffuses in the scattered light taking unit 8 can be efficiently and securely taken and irradiated onto the light receiving unit 9. Thereby, detection precision of the pulse wave of the human body based on the light receiving unit 9 can be enhanced.

Since the optical filter 17 that transmits light of a specific wavelength band of 900 nm or more is provided between the light receiving unit 9 and the scattered light receiving unit 8, irradiation of the unnecessary light, such as the external light, onto the light receiving unit 9 can be alleviated by the optical filter 17. Thereby, since only the scattered light of the observation light emitted from the light emitting unit 6 and scattered in the skin H can be securely received by the light receiving unit 9, the pulse wave of the human body can be accurately detected and detection precision of the pulse wave of the human body can be enhanced.

Since the light receiving unit 9 has a spectral sensitivity characteristic of reacting with the light of the specific wavelength band of about 900 nm transmitted by the optical filter 17, only light of the specific wavelength band that is transmitted through the optical filter 17 can be accurately received and can be subjected to photoelectric conversion. At this time, the unnecessary light included in the external light such as the sunlight can be shielded by the optical filter 17 and the change of the light receiving unit 9 due to the external light can be alleviated. Thereby, the pulse wave of the human body can be accurately detected and detection precision of the pulse wave of the human body can be enhanced.

The diffusion/irradiation ring portion 12 of the light guide unit 7 is mounted in the mounting hole 3b of the back cover 3 through the first waterproof packing 14, and the scattered light taking unit 8 is mounted in the diffusion/irradiation ring portion 12 through the second waterproof packing 16. When the biological information detecting apparatus 5 is mounted on the arm and used, even though moisture that contains a secretory substance, such as sweat, is generated on the surface of the arm, the moisture can be securely prevented from being infiltrated into the biological information detecting apparatus 5.

According to the biological information detecting method, the light emitting unit 6 is made to emit the observation light, the emitted observation light is annularly irradiated onto the skin H by the light guiding ring portion 11 and the diffusion/irradiation ring portion 12 of the light guide unit 7, the irradiated observation light is scattered in the skin H, the scattered light is taken by the scattered light taking unit 8 positioned in the central portion in the annular irradiation area E, the taken scattered light is received by the light receiving unit 9, and the biological information is detected. Therefore, the scattered light that is returned from the skin H among the observation light irradiated onto the skin H can be efficiently and stably received, and the biological information, such as the pulse wave, can be accurately detected.

That is, as illustrated in FIGS. 1 to 10, the first biological information detecting apparatus 5 that executes the biological information detecting method comprises the light emitting units 6 that emit the observation light of the specific wavelength band to optically observe the skin tissue of the human body, the annular light guide unit 7 that guides the observation light emitted from the light emitting units 6 and annularly diffuses and irradiates the observation light with respect to the skin H, the scattered light taking unit 8 that is disposed to contact the skin H at the position of the central portion surrounded by the annular irradiation area E where the observation light is annularly irradiated by the annular light guide unit 7 and takes the scattered light scattered in the skin H, and the light receiving unit 9 that is disposed on the side opposite to the skin H in the scattered light taking unit 8 and receives the scattered light taken by the scattered light taking unit 8.

Figure 30:
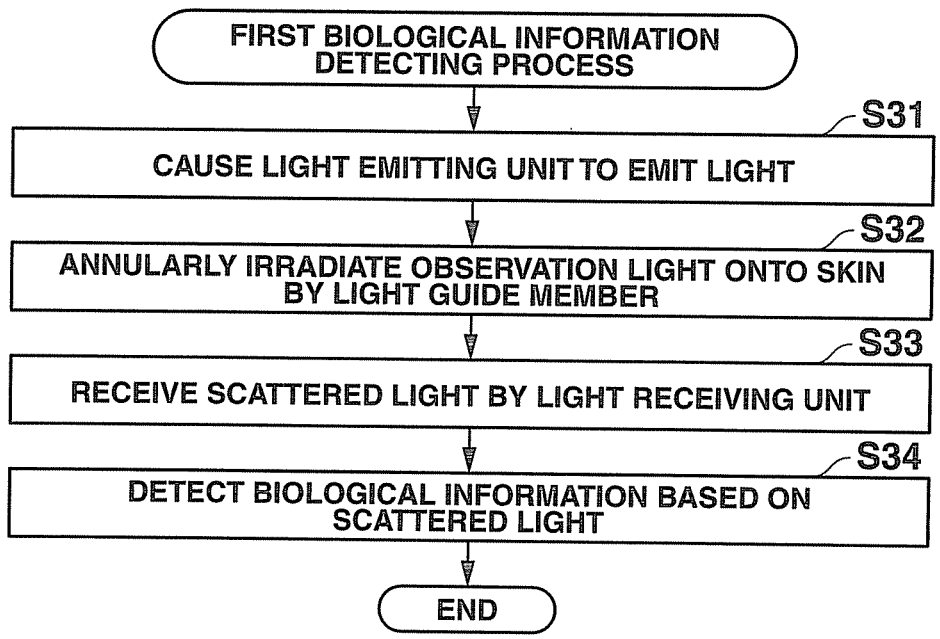
FIG. 30 is a flow chart illustrating an optical biological information detecting method according to a first embodiment of the present invention.

In the biological information detecting apparatus 5 having the above configuration, as shown in FIG. 30, the biological information detecting method according to the first embodiment comprises the light emitting step S31 of causing the light emitting unit 6 to emit the observation light, the irradiating step S32 of annularly irradiating the observation light emitted by the light emitting step S31 onto the skin H by the light guide unit 7, the light receiving step S33 of scattering the observation light irradiated by the irradiating step S32 in the skin H, taking the scattered light by the scattered light taking unit 8, and receiving the taken scattered light by the light receiving unit 9, and the biological information detecting step S34 of detecting the biological information, based on the scattered light received by the light receiving step S33.

According to the biological information detecting method having the above configuration, the light emitting unit 6 is made to emit the observation light, the emitted observation light is annularly irradiated onto the skin H by the light guide unit 7, the irradiated observation light is scattered in the skin H, the scattered light is taken by the scattered light taking unit 8, the taken scattered light is received by the light receiving unit 9, and the biological information can be accurately and easily detected based on the received scattered light.

In the first embodiment, the case where the light emitting units 6 are provided in the two places of the 3 o'clock side and the 9 o'clock side in the bottom surface of the circuit board 10 corresponding to the light guiding ring portion 11 has been described, but the present invention is not limited thereto. For example, the light emitting units 6 may be provided in three places or more in the bottom surface of the circuit board 10 corresponding to the light guiding ring portion 11 or the light emitting unit 6 may be provided only in one place in the bottom surface of the circuit board 10 corresponding to the light guiding ring portion 11.

In the first embodiment and the modification thereof, the case where one light receiving unit 9 is provided in the place positioned at the side opposite to the skin H in the scattered light taking unit 8 has been described, but the present invention is not limited thereto. For example, plural light receiving units 9 may be two-dimensionally disposed in the places positioned at the side opposite to the skin H in the scattered light taking unit 8. In this case, the plural light receiving units 9 are preferably disposed on the same circumference centered on an optical axis of the scattered light taking unit 8.

In the first embodiment and the modification thereof, the case where the bottom surface of the scattered light taking unit 8 that contacts the skin H is formed in the shape of the plano-concave lens has been described, but the present invention is not limited thereto. For example, the bottom surface of the scattered light taking unit 8 may be formed in a shape of a flat window. Even in this case, the scattered light taking unit 8 only needs to be disposed such that the observation light scattered in the skin H is obtained in a sensitivity area of the light receiving unit 9 in the vicinity of a central portion of the window.

Second Embodiment

Next, a second embodiment where the invention is applied to a wristwatch will be described with reference to FIGS. 11 to 14 and 30. In this case, the same components as those of the first embodiment illustrated in FIGS. 1 to 10 are denoted by the same reference numerals.

Figure 11:
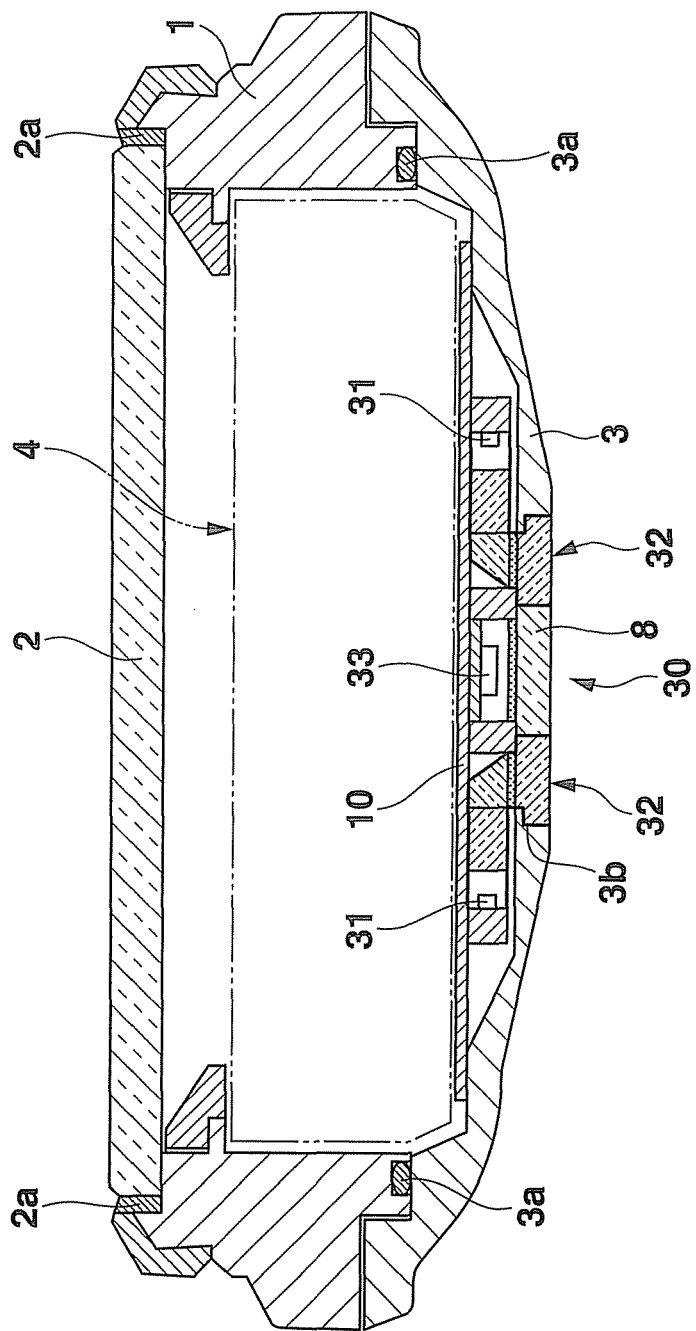
FIG. 11 is a schematic longitudinal cross-sectional view of a body case of a wristwatch where an optical biological information detecting apparatus according to a second embodiment of the present invention is combined.

As illustrated in FIG. 11, the configuration of the wristwatch according to the second embodiment is different from the configuration of the wristwatch according to the first embodiment in that a biological information detecting apparatus 30 is provided in a central portion of the back cover 3 of the wristwatch case 1, and the other configuration thereof is almost the same as that of the first embodiment.

Figure 12:
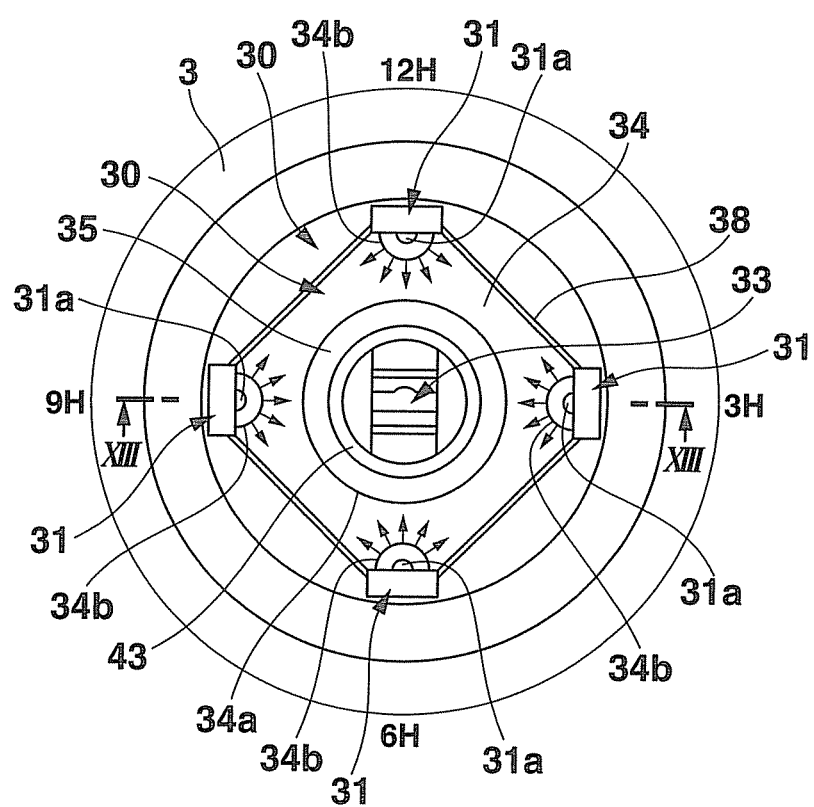
FIG. 12 is an enlarged view of a main portion of a back cover of the wristwatch of FIG. 11.
Figure 13:
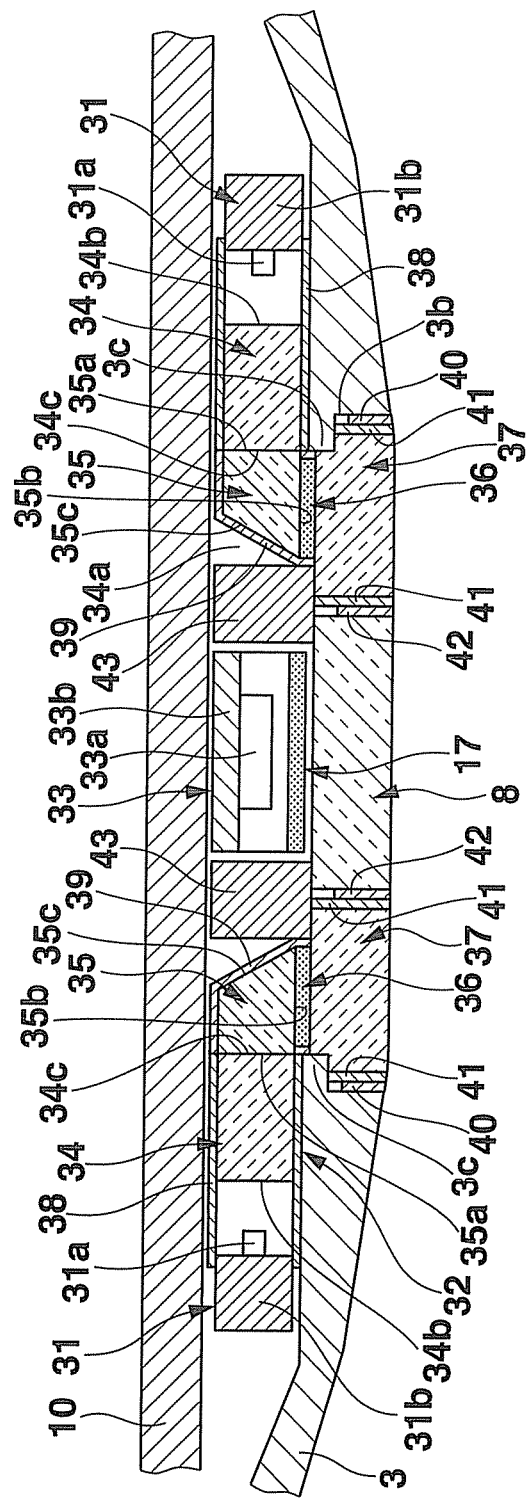
FIG. 13 is a cross-sectional view taken along a line XIII-XIII in FIG. 12.

As illustrated in FIGS. 11 to 13, the biological information detecting apparatus 30 comprises light emitting units 31 that emit observation light of a specific wavelength band to optically observe a skin tissue of a human body, an annular light guide unit 32 that guides the observation light emitted from the light emitting units 31 and annularly diffuses and irradiates the observation light with respect to a skin H, a scattered light taking unit 8 that contacts the skin H positioned in a central portion of an annular irradiation area E where the observation light is irradiated by the annular light guide unit 32, and a light receiving unit 33 that is disposed in a place positioned at the side opposite to the side of the skin H in the scattered light taking unit 8 and receives scattered light of the observation light taken by the scattered light taking unit 8.

In this case, the light emitting unit 31 and the light receiving unit 33 are provided on a bottom surface of a circuit board 10 for measurement, similar to the first embodiment. The circuit board 10 is positioned on the light guide unit 32 and is disposed in the wristwatch case 1. In the light guide unit 32, its lower side is fitted into the mounting hole 3b of the back cover 3 and its upper side is disposed on the bottom surface of the circuit board 10 in the wristwatch case 1.

Figure 14:
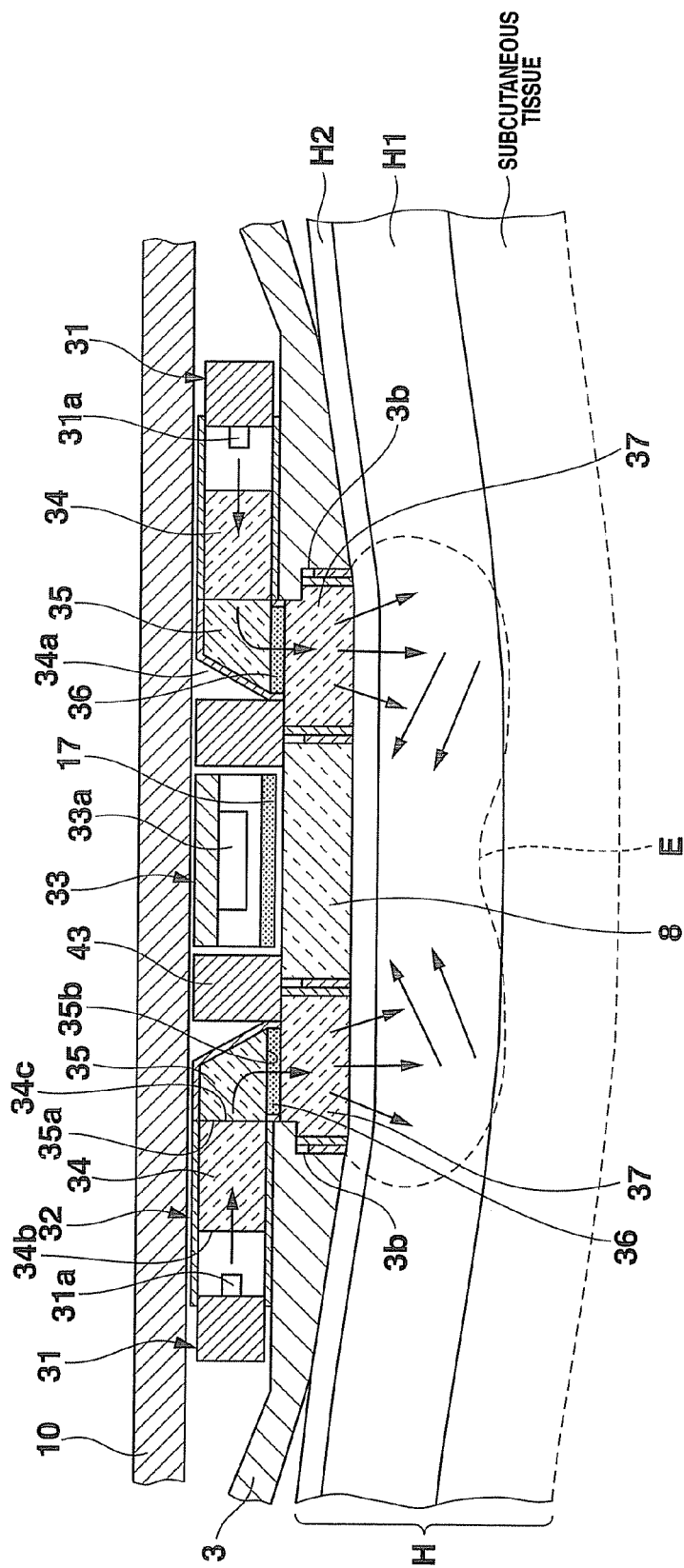
FIG. 14 is a cross-sectional view illustrating a state where biological information, such as a pulse wave, is optically measured while the back cover of the wristwatch illustrated in FIG. 13 contacts a skin of an arm.

Meanwhile, the light emitting unit 31 is of a side light emission type and has the configuration where a light emitting element 31a, such as a light emitting diode (LED), is provided on a side of an element substrate 31b. The light emitting element 31a is configured to emit infrared light ($\lambda p=940$ nm) where absorbance of melanine pigment contained in the skin H is low as the observation light. As illustrated in FIGS. 13 and 14, the light emitting units 31 are provided in four places corresponding to four directions of the 12 o'clock side, the 3 o'clock side, the 6 o'clock side, and the 9 o'clock side in a bottom surface of the circuit board 10 corresponding to the outer circumference of the light guide unit 32, respectively.

The light guide unit 32 comprises a light guiding ring portion 34, a diffusion/reflection ring portion 35, a diffusion ring portion 36, and a diffusion/irradiation ring portion 37, as illustrated in FIGS. 13 and 14. The light guiding ring portion 34 is formed in a flat, almost square shape, using a material such as transparent glass or a transparent resin with a high light transmitting property. In the light guiding ring portion 34, a circular hole 34a is formed in a central portion thereof and incident surfaces 34b where the corresponding light emitting units 31 are disposed are formed in corner portions, respectively.

In this case, in the light guiding ring portion 34, the incident surfaces 34b of the corner portions are disposed on the bottom surface of the circuit board 10 to correspond to the four directions of the 12 o'clock side, the 3 o'clock side, the 6 o'clock side, and the 9 o'clock side. That is, as illustrated in FIG. 12, the incident surface 34b of the light guiding ring portion 34 is a notched concave portion that is formed by biting each corner portion of the light guiding ring portion 34 in a semicircular shape, and the light emitting element 31a of the light emitting unit 31 is inserted into the notched concave portion having the semicircular shape. Thereby, the light guiding ring portion 34 is configured such that the observation light emitted from the light emitting element 31a is incident radially from the four directions, toward the circular hole 34a of the central portion from the four corner portions of the light guiding ring portion 34.

In the light guiding ring portion 34, an inner circumferential surface of the circular hole 34a of the central portion is formed in the emission surface 34c. Thereby, as illustrated in FIG. 14, the light guiding ring portion 34 is configured to take the observation light emitted from the light emitting unit 31 from the incident surfaces 34b of the corner portions of the four directions, guide the taken observation light from the four directions to the circular hole 34a of the central portion, and discharge the guided observation light from the emission surface 34c corresponding to the inner circumferential surface of the circular hole 34a.

In this case, as illustrated in FIGS. 13 and 14, on an external surface of the light guiding ring portion 34, a first reflection layer 38 is provided by a metal vapor deposition method using aluminum or a plating method, except for the incident surfaces 34b of the corner portions and the emission surface 34c corresponding to the inner circumferential surface of the circular hole 34a. The first reflection layer 38 prevents the observation light, which is incident in the inner portion of the light guiding ring portion 34, from leaking to the outside of the light guiding ring portion 34.

As illustrated in FIGS. 13 and 14, a diffusion/reflection ring portion 35 is formed in an almost circular ring shape, using a synthetic resin such as a clouded or milky acrylic resin with a light diffusing property. The diffusion/reflection ring portion 35 is formed to have almost the same thickness as the light guiding ring portion 34, and is disposed in the circular hole 34a of the light guiding ring portion 34. In this case, the diffusion/reflection ring portion 35 is configured such that an outer circumferential surface thereof is formed in an incident surface 35a and the incident surface 35a is disposed to adhere closely to the emission surface 34c corresponding to the inner circumferential surface of the circular hole 34a of the light guiding ring portion 34.

As illustrated in FIGS. 13 and 14, the bottom surface of the diffusion/reflection ring portion 35 is formed in an emission surface 35b that discharges the observation light taken from the incident surface 35a of the outer circumferential surface to the skin H. In the inner circumferential surface of the diffusion/reflection ring portion 35, a reflection surface 35c that reflects the observation light taken from the incident surface 35a of the outer circumferential surface to the emission surface 35b of the bottom surface is formed to be annularly continuous. The reflection surface 35c is formed in a portion of a reverse conical face, that is, a portion of the reverse conical face tapered toward the lower side.

As illustrated in FIGS. 13 and 14, on an external surface of the diffusion/reflection ring portion 35, a second reflection layer 39 is provided by a metal vapor deposition method using aluminum or a plating method, except for the incident surfaces 35a of the outer circumferential surface and the emission surface 35b of the bottom surface. The second reflection layer 39 prevents the observation light, which is incident in the inner portion of the diffusion/reflection ring portion 35, from leaking to the outside of the diffusion/reflection ring portion 35 and optically isolates a light receiving portion 33 to be described below.

Thereby, the diffusion/reflection ring portion 35 is configured to take the observation light discharged from the emission surface 34c corresponding to the inner circumferential surface of the light guiding ring portion 34 in the inner portion thereof from the incident surface 35a of the outer circumferential surface, diffuse the taken observation light while guiding the observation light along the annular shape of the diffusion/reflection ring portion 35, reflect the observation light to the emission surface 35b of the bottom surface by the reflection surface 35c provided in the inner circumferential portion, and discharge the diffused and reflected observation light from the emission surface 35b of the bottom surface to the lower side.

As illustrated in FIGS. 13 and 14, the diffusion ring portion 36 is formed in an almost circular ring shape, using a synthetic resin with a light diffusing property. The diffusion ring portion 36 is formed in a sheet shape having the small thickness, and is disposed to adhere closely to the emission surface 35*b* of the bottom surface of the diffusion/reflection ring portion 35. Similar to the diffusion/reflection ring portion 35, on each of the outer circumferential surface and the inner circumferential surface of the diffusion ring portion 36, a second reflection layer 39 that prevents the incident observation light from leaking to the outside of the diffusion ring portion 36 and optically isolates the light receiving portion 33 to be described below is provided by a metal vapor deposition method using aluminum or a plating method.

Thereby, as illustrated in FIGS. 13 and 14, the diffusion ring portion 36 is configured to take the observation light discharged from the emission surface 35*b* of the diffusion/reflection ring portion 35 in the inner portion thereof from the top surface, sufficiently diffuse the taken observation light to become uniform while guiding the observation light along the annular shape of the diffusion ring portion 36, and uniformly discharge the diffused observation light from the bottom surface to the skin H without irregularity.

As illustrated in FIGS. 13 and 14, the diffusion/irradiation ring portion 37 is formed in an almost circular ring shape, using a synthetic resin such as an acrylic resin with diffuseness. The diffusion/irradiation ring portion 37 is disposed on the lower side of the diffusion/reflection ring portion 35 through the diffusion ring portion 36 and is fitted into the mounting hole 3*b* of the back cover 3 through the first waterproof packing 40. In this case, the diffusion/irradiation ring portion 37 is formed such that the outer circumference thereof is slightly lager than the outer circumference of the diffusion/reflection ring portion 35 and the inner circumference thereof is slightly smaller than the inner circumference of the diffusion/reflection ring portion 35.

Thereby, the diffusion/irradiation ring portion 37 is configured to take the observation light discharged from the diffusion/reflection ring portion 35 and annularly diffused without irregularity in the diffusion ring portion 36 from the top surface, further diffuse the taken observation light, annularly discharge the diffused observation light from the bottom surface, and uniformly diffuse and irradiate the observation light over the wide area of the ring shape with respect to the skin H.

Even in this case, as illustrated in FIGS. 13 and 14, on the outer circumferential surface and the inner circumferential surface of the diffusion/irradiation ring portion 37, a third reflection layer 41 is provided by a metal vapor deposition method using aluminum or a plating method, except for the top surface and the bottom surface. The third reflection layer 41 prevents the observation light, which is incident in the inner portion of the diffusion/irradiation ring portion 37, from leaking to the outside of the diffusion/irradiation ring portion 37 and optically isolates the light receiving portion 33 to be described below.

The position of the diffusion/irradiation ring portion 37 is regulated such that the diffusion/irradiation ring portion comes into contact with a protrusion portion 3*c* provided in the mounting hole 3*b* of the back cover 3 and is not pressed into the wristwatch case 1. In this case, as illustrated in FIGS. 13 and 14, the bottom surface of the diffusion/irradiation ring portion 37 is disposed at the same height as that of a lowermost portion in the bottom surface of the back cover 3. Thereby, the diffusion/irradiation ring portion 37 contacts the skin H together with the bottom surface of the back cover 3 without generating a step by the bottom surface of the diffusion/irradiation ring portion 37 and the bottom surface of the back cover 3.

As illustrated in FIGS. 13 and 14, in the diffusion/irradiation ring portion 37, a scattered light taking unit 8 that takes the scattered light of the observation light irradiated onto the inner portion of the skin H is provided. The scattered light taking unit 8 is also formed in a circular flat shape, using a material such as a transparent glass or a transparent resin with a high refractive index, similar to the first embodiment. In this case, the scattered light taking unit 8 is formed to have almost the same thickness as that of the diffusion/irradiation ring portion 37. Thereby, the top surfaces and the bottom surfaces of the scattered light taking unit 8 and the diffusion/irradiation ring portion 37 are disposed on almost the same plane.

As illustrated in FIGS. 13 and 14, the scattered light taking unit 8 is mounted in the diffusion/irradiation ring portion 37 with the second waterproof packing 42 between the outer circumferential surface thereof and the inner circumferential surface of the diffusion/irradiation ring portion 37. The scattered light taking unit 8 is configured to contact the skin H positioned in a central portion of an irradiation area E having a ring shape where a bottom surface is irradiated with the observation light by the diffusion/irradiation ring portion 37. Thereby, the scattered light taking unit 8 is configured to take the scattered light of the observation light irradiated onto the inner portion of the skin H from the bottom surface and irradiate the taken scattered light from the top surface to the light receiving portion 33.

Similar to the first embodiment, the light receiving unit 33 receives the scattered light of the observation light taken by the scattered light taking unit 8 and performs photoelectric conversion. The light receiving unit 33 has the configuration where a light receiving element 33*a*, such as a silicon photo diode, is provided downward on the bottom surface of the element substrate 33*b*. As illustrated in FIGS. 13 and 14, the light receiving unit 33 is provided on the bottom surface of the circuit board 10 in the place positioned at the side (upper side in FIG. 13) opposite to the skin H in the scattered light taking unit 8, that is, the place positioned in the vicinity of the focal position on an optical axis of the scattered light taking unit 8, in a state where the light receiving element 33*a* is stored in a holder portion 43.

Similar to the first embodiment, the light receiving element 33*a* of the light receiving unit 33 has a spectral sensitivity characteristic of reacting strongest with light of a specific wavelength band of about $\lambda=940$ nm. That is, the light receiving element 33*a* is configured such that light reception sensitivity is gradually lowered as the wavelength becomes short with respect to light of a wavelength band of 940 nm or less, is rapidly lowered with respect to light of a wavelength band of 940 nm or more, and becomes highest with respect to light having a wavelength of 940 nm.

As illustrated in FIGS. 13 and 14, at the lower side of the light receiving element 33*a*, that is, between the light receiving element 33*a* and the scattered light taking unit 8, an optical filter 17 is disposed in the holder portion 43 positioned below the light receiving element 33*a*. Similar to the first embodiment, the optical filter 17 is configured to transmit light of a specific wavelength band of 900 nm or more and shield light of a wavelength band of 900 nm or less, such that the light receiving element 33*a* alleviates an influence from a measurement change due to external light such as sunlight.

In this case, the holder portion 43 of the light receiving unit 33 is formed of a metal with a light shielding property, such as aluminum, and its surface is subjected to alumite treatment to have a reflection function. Thereby, the light receiving element 33*a* can be optically protected. As illustrated in FIGS. 13 and 14, the holder portion 43 is formed to have the same thickness as that of the light emitting unit 31 (length of a vertical direction), and is disposed in a central portion of the diffusion/reflection ring portion 35.

Thereby, the light guiding ring portion 34, the diffusion/reflection ring portion 35, and the light receiving unit 33 are formed to have the thicknesses within the thickness of the light emitting unit 31 (length of the vertical direction), and the top and bottom surfaces thereof are disposed on almost the same plane. In this state, the light guiding ring portion 34, the diffusion/reflection ring portion 35, and the light receiving unit 33 are two-dimensionally disposed at the thickness of about 1 mm. The optical filter 17 is formed to have almost the same thickness as that of the diffusion ring portion 36, and is disposed on almost the same plane as the inner surface (top surface in FIG. 13) of the back cover 3 together with the diffusion ring portion 36.

Similar to the first embodiment, the circuit configuration of the biological information detecting apparatus 30 comprises a CPU (central processing unit) 20 that performs whole control of the apparatus, a photoelectric signal detecting module 26 that comprises the light emitting unit 31 and the light receiving unit 33, a light emitting unit driving circuit 21 that drives the light emitting unit 31 of the photoelectric signal detecting module 26, an I/V converting circuit 22 that converts a current signal output from the light receiving unit 33 of the photoelectric signal detecting module 26 into a voltage signal, a display unit 23 that displays a measurement result of biological tissue, such as a pulse wave, as the biological information, a power supply unit 24 that supplies a power supply voltage to the individual units, and a switch unit 25 operated by a user.

As illustrated in FIG. 30, a biological information detecting method of the biological information detecting apparatus 30 comprises a light emitting step S31 of causing the CPU 20 to emit observation light from the light emitting element 31*a*, an irradiating step S32 of annularly irradiating the observation light emitted by the light emitting step S31 onto the skin H by the light guide unit 32, a light receiving step S33 of scattering the observation light irradiated by the irradiating step S32 in the skin H, taking the scattered light by the scattered light taking unit 8, and receiving the taken scattered light by the light receiving element 33*a*, and a biological information detecting step S34 of causing the CPU 25 to detect biological information, based on the scattered light received by the light receiving step S33.

Next, a function of the biological information detecting apparatus 30 will be described.

The wristwatch case 1 is previously mounted on the arm and the bottom surface of the back cover 3 is made to contact the skin H of the arm, as illustrated in FIG. 4. At this time, the bottom surface of the back cover 3 is moderately curved and protruded. However, the bottom surface of each of the diffusion/irradiation ring portion 37 of the light guide unit 32 and the scattered light taking unit 8 in the biological information detecting apparatus 30 is formed to become a flat surface, and the flat surfaces thereof are disposed on the same plane without a step. Thereby, the flat surfaces of the diffusion/irradiation ring portion 37 and the scattered light taking unit 8 equally contact the surface of the skin H of the arm.

In this state, if a command that causes the switch unit 25 to be operated and start the measurement is given to the CPU 25, the CPU 25 outputs a driving signal to the light emitting portion driving circuit 21, the light emitting unit driving circuit 21 continuously outputs a constant current pulse to the plural light emitting units 31 for a constant time with a constant period, and simultaneously controls the driving of the plural light emitting units 31. While the driving of the plural light emitting units 31 is controlled, the plural light emitting units 31 stably emit the observation light with constant light intensity.

At this time, if the plural light emitting units 31 are driven by the light emitting unit driving circuit 21, the light emitting element 31*a* emits light of an infrared band of $\lambda p=940$ nm as the observation light. As illustrated in FIG. 14, the emitted observation light is taken in the light guiding ring portion 34 from the incident surfaces 34*b* of the four directions in the light guiding ring portion 34 of the light guide unit 32. The taken observation light is guided to the circular hole 34*a* of the central portion by the light guiding ring portion 34, and is annularly discharged from the emission surface 34*c* corresponding to the inner circumferential surface of the circular hole 34*a* of the light guiding ring portion 34.

The observation light discharged from the light guiding ring portion 34 is incident from the incident surface 35*a* corresponding to the outer circumferential surface of the diffusion/reflection ring portion 35 that is disposed in the circular hole 34*a* of the light guiding ring portion 34. The incident observation light is annularly guided along the diffusion/reflection ring portion 35 while being diffused by the diffusion/reflection ring portion 35, and is reflected to the emission surface 35*b* of the bottom surface of the diffusion/reflection ring portion 35 by the reflection surface 35*c* provided on the inner circumferential surface of the diffusion/reflection ring portion 35. The observation light annularly guided and reflected is discharged to the lower side toward the skin H from the emission surface 35*b* of the bottom surface of the diffusion/reflection ring portion 35.

The observation light discharged from the diffusion/reflection ring portion 35 is incident in the diffusion ring portion 36 disposed on the lower side of the diffusion/reflection ring portion 35. The incident observation light is sufficiently diffused to become uniform and discharged to the lower side, while being annularly guided by the diffusion ring portion 36. The observation light uniformly discharged from the diffusion ring portion 36 is incident in the diffusion/irradiation ring portion 37 disposed on the lower side of the diffusion ring portion 36.

The observation light incident in the diffusion/irradiation ring portion 37 is further diffused by the diffusion/irradiation ring portion 37, and is annularly discharged as the uniform observation light from the bottom surface of the diffusion/irradiation ring portion 37 contacting the skin H. The discharged observation light is uniformly irradiated onto the skin H of the arm over the wide range of the ring shape. As illustrated in FIG. 14, the irradiated observation light is incident in the epidermis H2 and the dermis H1 of the skin H.

At this time, even though the epidermis H2 contains the large amount of melanine pigment, the observation light is light of an infrared band of $\lambda p=940$ nm. For this reason, the amount of light that is absorbed by the melanine pigment is small and the light is securely incident in the dermis H1. Since the epidermis H2 has the layer thickness of about 0.1 to 0.2 mm, which is smaller than that of the dermis H1, most of the irradiated observation light transmits the epidermis H2 and is incident in the dermis H1 having the layer thickness of about 2 mm.

The observation light incident in the inner portion of the dermis H1 is uniformly irradiated over a wide area of a ring shape, as compared with the case where the observation light is spotlightingly irradiated onto a portion. For this reason, since the amount of hemoglobin that is a light absorbing substance in the dermis H1 in the irradiation area increases, the large amount of observation light is absorbed in the dermis H1 and the amount of observation light that arrives at a subcutaneous tissue of the inner side (lower side in FIG. 14) of the dermis H1 decreases.

The observation light incident in the dermis H1 is absorbed and scattered by the biological tissue of the dermis H1, and a portion of the scattered light transmits the epidermis H2 again and is discharged from the surface of the epidermis H2. Even at this time, since the small amount of scattered light is absorbed by the melanine pigment, the scattered light securely transmits the epidermis H2 and is taken in the scattered light taking unit 8.

Since the scattered light taking unit 8 is formed of a material having a high refractive index, the scattered light taken by the scattered light taking unit 8 among the scattered light scattered by the biological tissue in the dermis H1 and the scattered light taken from the outer circumferential portion of the scattered light taking unit 8 can be incident in the light receiving unit 33 disposed on the side opposite to the skin H, from a front direction. Among the scattered light transmitted through the scattered light taking unit 8, light of a specific wavelength band of 900 nm or more is selected by the optical filter 17, the selected light of the specific wavelength band transmits the optical filter 17, and the transmitted light of the specific wavelength band is received by the light receiving element 33a of the light receiving unit 33 and is subjected to photoelectric conversion.

The current signal subjected to the photoelectric conversion in the light receiving element 33a is converted into a voltage signal by the I/V converting circuit 22, and the voltage signal is converted into a digital signal by the A/D converter of the CPU 20. The converted digital signal is stored in the incorporated memory as time-series data by the CPU 20, and the CPU 20 performs a frequency analysis based on the time-series data, estimates the signal as biological information such as a pulse wave, and displays the information on the display unit 23.

Meanwhile, the outline of the operational principle of the biological information detecting apparatus 30 is as described above. According to the operational principle, absorbance where hemoglobin in blood absorbs light greatly changes at about 600 nm, and the absorbance is very high at a wavelength shorter than 600 nm, as compared with a wavelength of 600 nm or more. This reason is as follows. The surface-side inner portion of the skin H consists essentially of the dermis H1 including the blood capillary corresponding to an observation object of the pulse wave and the epidermis H2 including the melanine pigment of the surface side, and the observation light may be absorbed by the melanine pigment, if the large amount of melanine pigment is contained in the epidermis H2.

That is, the melanine pigment has extraordinarily high absorbance in a wavelength band from ultraviolet light to visible light. When the large amount of melanine pigment is contained in the epidermis H2 (for example, in the case of a person of a dark skin color), even though observation light having a wavelength of 600 nm or less is irradiated onto the skin, the observation light that reaches the dermis H1 including the blood capillary, repeats scattering and absorption in a tissue of the dermis H1, passes through the epidermis H2 again, and arrives at the light receiving element 33a is weak light and cannot be sufficiently received. For this reason, if the light of the infrared band of 940 nm is observed and emitted by the light emitting portion 31a, the amount of observation light that is absorbed by the melanine pigment contained in the epidermis H2 can be minimally suppressed and a biological tissue, such as a pulse wave, can be accurately measured.

As such, according to the biological information detecting apparatus 30, if the observation light of the specific wavelength band of $\lambda p=940$ nm is emitted by the light emitting unit 31, the observation light can be annularly diffused and irradiated onto the skin H by the light guide unit 32. Therefore, the observation light can be uniformly irradiated over the wide range of the skin H, and the scattered light of the observation light scattered in the skin H can be received by the light receiving unit 33 disposed to correspond to the central portion in the annular irradiation area E. As a result, the scattered light of the observation light can be efficiently and stably received by the light receiving unit 33.

For this reason, the observation light from the light emitting unit 31 can be uniformly irradiated over the wide range of the skin H, and the light irradiation path through which the observation light from the light emitting unit 31 is irradiated onto the skin H and the light reception path through which the scattered light of the observation light scattered in the skin H is received can be perfectly isolated from each other. Therefore, the scattered light of the observation light that is diffused in and irradiated onto the skin H can be efficiently and stably received by the light receiving unit 33. Thereby, a biological tissue, such as a pulse wave, can be accurately measured.

In this case, since the light emitting element 31a of the light emitting unit 31 emits the infrared light ($\lambda p=940$ nm) where absorbance of the melanine pigment contained in the epidermis H2 of the skin H is low as the observation light, even though the epidermis H2 contains the large amount of melanine pigment, the observation light irradiated onto the skin H can be securely incident in the dermis H1 without being absorbed by the melanine pigment. Since the epidermis H2 has the layer thickness smaller than that of the dermis H1, most of the observation light irradiated onto the skin H transmits the epidermis H2. Therefore, most of the observation light irradiated onto the skin H can be securely incident in the dermis H1.

As such, the observation light incident in the dermis H1 is uniformly irradiated over the wide area of the ring shape, as compared with the case where the observation light is spot-lightingly irradiated onto the portion. Therefore, the amount of hemoglobin that is a light absorbing substance in the dermis H1 where the observation light is irradiated can be increased. Thereby, a change in the amount of hemoglobin in the biological tissue of the dermis H1 can be accurately measured.

That is, if the amount of hemoglobin that is the light absorbing substance in the dermis H1 increases, the large amount of observation light is absorbed in the dermis H1, the amount of observation light that arrives at the subcutaneous tissue of the lower side of the dermis H1 decreases, and the scattered light of the observation light from the subcutaneous tissue decreases. As a result, a change in the amount of hemoglobin generated in the biological tissue of the dermis H1 can be accurately measured.

The light guide unit 32 comprises the light guiding ring portion 34 that takes the observation light emitted from the light emitting unit 31 from the incident surface 34b of the side, guides the observation light to the circular hole 34a of the central portion, and discharges the guided observation light from the emission surface 34c corresponding to the inner circumferential surface of the circular hole 34a, and the diffusion/reflection ring portion 35 that is disposed in the circular hole 34a of the light guiding ring portion 34, takes the observation light discharged from the emission surface 34c of the light guiding ring portion 34 from the incident surface 35a of the outer circumferential surface, diffuses and reflects the observation light while annularly guiding the observation light, and discharges the observation light from the emission surface 35b of the bottom surface to the lower side. The observation light emitted from the light emitting unit 31 can be efficiently and securely diffused in and irradiated onto the skin H in an annular shape and the size of the biological information detecting apparatus 30 can be decreased.

That is, the plural light emitting units 31, the light guiding ring portion 34, the diffusion/reflection ring portion 35, and the light receiving unit 33 have almost the same thickness and their top and bottom surfaces are parallel to each other and are disposed on almost the same plane. Therefore, the light guiding ring portion 34, the diffusion/reflection ring portion 35, and the light receiving unit 33 can be two-dimensionally disposed at the same position within the thickness of the light emitting unit 31 having the largest thickness. Thereby, all of the plural light emitting elements 31a, the light guiding ring portion 34, the diffusion/reflection ring portion 35, and the light receiving element 33a can be two-dimensionally disposed within the same thickness.

For this reason, when the thickness of the light emitting unit 31 is about 1 mm, the plural light emitting units 31, the light guiding ring portion 34, the diffusion/reflection ring portion 35, and the light receiving unit 33 can be formed to have the thickness of about 1 mm. Therefore, the size of the biological information detecting apparatus 30 can be decreased and the plural light emitting units 31, the light guiding ring portion 34, the diffusion/reflection ring portion 35, and the light receiving unit 33 can be two-dimensionally mounted on the bottom surface of the common circuit board 10. As a result, the biological information detecting apparatus can be compactly and easily assembled in the wristwatch case 1.

Since the plural light emitting units 31 are disposed in the plural places of the outer circumferential surface of the light guiding ring portion 34, for example, in the corner portions positioned in the four directions of the 12 o'clock side, the 3 o'clock side, the 6 o'clock side, and the 9 o'clock side, respectively, the observation light of the sufficiently large amount can be discharged from the emission surface 34c corresponding to the inner circumferential surface of the circular hole 34a of the light guiding ring portion 34, and the observation light of the large amount can be discharged from the emission surface 35b of the diffusion/reflection ring portion 35 to the skin H.

In this case, the light guiding ring portion 34 is formed in a flat, square shape, the circular hole 34a is provided in the central portion of the light guiding ring portion 34, and the incident surfaces 34b where the light emitting units 31 are disposed are provided in the corner portions, respectively. For example, the observation light emitted by the light emitting units 31 from the four directions of the 12 o'clock side, the 3 o'clock side, the 6 o'clock side, and the 9 o'clock side can be uniformly taken in the light guiding ring portion 34. Thereby, the observation light can be almost uniformly discharged from the emission surface 34c corresponding to the inner circumferential surface of the circular hole 34a of the light guiding ring portion 34.

In the inner circumferential portion of the diffusion/reflection ring portion 35, the reflection surface 35c that reflects the observation light taken from the incident surface 35a corresponding to the outer circumferential surface to the emission surface 35b of the bottom surface of the diffusion/reflection ring portion 35 is provided to be annularly continuous. When the observation light that is discharged from the emission surface 34c of the light guiding ring portion 34 and taken from the incident surface 35a of the diffusion/reflection ring portion 35 is annularly guided while being diffused by the diffusion/reflection ring portion 35, the observation light can be efficiently reflected to the emission surface 35b of the bottom surface of the diffusion/reflection ring portion 35 by the reflection surface 35c. Thereby, the observation light can be efficiently and annularly discharged.

On the external surfaces of the light guiding ring portion 34 and the diffusion/reflection ring portion 35, the first and second reflection layers 38 and 39 that prevent the observation light from being leaked and optically isolate the light receiving unit 33 are provided, except for the incident surfaces 34b and 35a and the emission surfaces 34c and 35b. Thereby, the observation light emitted from the light emitting unit 31 can be securely taken in the light guiding ring portion 34, and the taken observation light can be efficiently and sufficiently discharged from the emission surface 35b of the diffusion/reflection ring portion 35 without being leaked to the outside.

On the emission surface 35b of the diffusion/reflection ring portion 35, the diffusion ring portion 36 that takes the observation light discharged from the emission surface 35b and uniformly diffuses the observation light while guiding the observation light along an annular shape is provided. Therefore, when the observation light diffused and reflected by the diffusion/reflection ring portion 35 is taken by the diffusion ring portion 36 and the taken observation light is discharged from the bottom surface, the observation light can be uniformly discharged along the annular shape without irregularity.

Since the optical filter 17 that transmits the light of the specific wavelength band is provided on the bottom surface corresponding to the incident surface of the light receiving unit 33, irradiation of the unnecessary light, such as the external light, onto the light receiving unit 33 can be alleviated by the optical filter 17. Thereby, since only the scattered light of the observation light emitted from the light emitting unit 31 and scattered in the skin H can be securely received by the light receiving unit 33, the biological tissue can be accurately measured and detection precision of the pulse wave of the human body can be enhanced.

In this case, since the light receiving unit 33 has a spectral sensitivity characteristic of reacting with the light of the specific wavelength band of about 900 nm transmitted by the optical filter 17, only light of the specific wavelength band transmitted through the optical filter 17 can be accurately received and can be subjected to photoelectric conversion. At this time, the unnecessary light included in the external light such as the sunlight can be shielded by the optical filter 7 and the change of the light receiving unit 33 due to the external light can be alleviated. Thereby, the biological tissue can be accurately measured and detection precision of the pulse wave of the human body can be enhanced.

The biological information detecting apparatus 30 comprises the diffusion/irradiation ring portion 37 that is disposed to correspond to the emission surface 35b of the diffusion/reflection ring portion 35, takes the observation light discharged from the emission surface 35b from the top surface, and annularly diffuses and irradiates the observation light from the bottom surface to the skin H, and the observation light taking unit 8 that is disposed in the central portion positioned at the inner circumferential side of the diffusion/irradiation ring portion 37 to correspond to the light receiving unit 33, takes the scattered light of the observation light irradiated onto the skin H by the diffusion/irradiation ring portion 37, and irradiates the observation light onto the light receiving unit 33. Therefore, the observation light can be uniformly irradiated over the wide range of the skin H and the scattered light of the observation light that is scattered in the skin H can be taken by the scattered light taking unit 8 and received by the light receiving unit 33. As a result, the scattered light of the observation light can be efficiently and stably received by the light receiving unit 33.

In this case, the thicknesses of the diffusion/reflection ring portion 37 and the scattered light taking unit 8 are almost equal to each other, and the top surfaces and the bottom surfaces thereof are parallel to each other and are disposed on almost the same plane. Therefore, when the scattered light taking unit 8 is fitted into the diffusion/irradiation ring portion 37, the diffusion/reflection ring portion 37 and the scattered light taking unit 8 are two-dimensionally disposed, and can be mounted without generating a step on the bottom surfaces. In this state, since the diffusion/reflection ring portion 37 and the scattered light taking unit 8 can be fitted into the mounting hole 3b of the back cover 3, the size of the biological information generating apparatus can be decreased.

The bottom surfaces of the diffusion/irradiation ring portion 37 and the scattered light taking unit 8 are disposed on the same plane as the bottom surface of the back cover 3, the bottom surfaces of the diffusion/irradiation ring portion 37 and the scattered light taking unit 8 and the bottom surface of the back cover 3 can contact the skin H in a flat state without generating a step, and the biological tissue can be accurately measured.

Even in this case, the third reflection layer 41 that optically isolates the diffusion/irradiation ring portion 37 and the scattered light taking unit 8 from each other is formed between the diffusion/irradiation ring portion 37 and the scattered light taking unit 8, and the observation light emitted from the light emitting unit 31 is taken in the diffusion/irradiation ring portion 37 via the light guiding ring portion 34, the diffusion/reflection ring portion 35, and the diffusion ring portion 36. When the taken observation light is irradiated onto the skin H, the observation light can be prevented from being directly incident in the scattered light taking unit 8. Thereby, the pulse wave can be measured with high precision.

The diffusion ring portion 36 of the light guide unit 32 is mounted in the mounting hole 3b of the back cover 3 through the first waterproof packing 40, and the scattered light taking unit 8 is mounted in the diffusion ring portion 36 through the second waterproof packing 42. When the biological information detecting apparatus 30 is mounted on the arm and used, even though moisture that contains a secretory substance, such as sweat, is generated on the surface of the arm, the moisture can be securely prevented from being infiltrated into the biological information detecting apparatus 30.

In the wristwatch, the biological information detecting apparatus 30 is provided in the back cover 3 in the wristwatch case 1. Thus, the wristwatch case 1 can be mounted on the arm and used. That is, if the wristwatch case 1 is mounted on the arm, since the back cover 3 contacts the skin H of the arm, a portion of the biological information detecting apparatus 30 that is exposed from the mounting hole 3b of the contacted back cover 3 can be contacted with the skin H. For this reason, the biological tissue can be easily and simply measured anytime and anywhere, in a state where the wristwatch case 1 is mounted on the arm.

According to the biological information detecting method, the light emitting element 31a of the light emitting unit 31 is made to emit the observation light, the emitted observation light is annularly irradiated onto the skin H by the light guiding ring portion 34 corresponding to the light guide unit 32, the diffusion/reflection ring portion 35, the diffusion ring portion 36, and the diffusion/irradiation ring portion 37, the irradiated observation light is scattered in the skin H, the scattered light is taken by the scattered light taking unit 8 positioned in the central portion in the annular irradiation area E, the taken scattered light is received by the light receiving element 33a of the light receiving unit 33, and the biological information is detected. Therefore, the scattered light returned from the skin H among the observation light irradiated onto the skin H can be efficiently and stably received, and the biological information, such as the pulse wave, can be accurately detected.

That is, as illustrated in FIGS. 11 to 14, the biological information detecting apparatus 30 that executes the biological information detecting method comprises the light emitting element 31a that emits the observation light of the specific wavelength band to optically observe the skin tissue of the human body, the annular light guide unit 32 that guides the observation light emitted from the light emitting element 31a and annularly diffuses and irradiates the observation light with respect to the skin H, the scattered light taking unit 8 that is disposed to contact the skin H at the position of the central portion surrounded by the annular irradiation area E where the observation light is annularly irradiated by the annular light guide unit 32, and takes the scattered light scattered in the skin H, and the light receiving element 33a that is disposed on the side opposite to the skin H in the scattered light taking unit 8 and receives the scattered light taken by the scattered light taking unit 8.

In the biological information detecting apparatus 30 having the above configuration, the biological information detecting method according to the second embodiment comprises the light emitting step S31 of causing the light emitting element 31a to emit the observation light, the irradiating step S32 of annularly irradiating the observation light emitted by the light emitting step S31 onto the skin H by the light guide unit 32, the light receiving step S33 of scattering the observation light irradiated by the irradiating step S32 in the skin H, taking the scattered light by the scattered light taking unit 8, and receiving the taken scattered light by the light receiving element 33a, and the biological information detecting step S34 of detecting the biological information, based on the scattered light received by the light receiving step S33, as illustrated in FIG. 30.

According to the biological information detecting method having the above configuration, the light emitting element 31a is made to emit the observation light, the emitted observation light is annularly irradiated onto the skin H by the light guide unit 32, the irradiated observation light is scattered in the skin H, the scattered light is taken by the scattered light taking unit 8, the taken scattered light is received by the light receiving element 33a, and the biological information can be accurately and easily detected based on the received scattered light.

Third Embodiment

Next, a third embodiment where the invention is applied to a wristwatch will be described with reference to FIGS. 15, 16, and 30. In this case, the same components as those of the second embodiment illustrated in FIGS. 11 to 14 are denoted by the same reference numerals.

Figure 15:
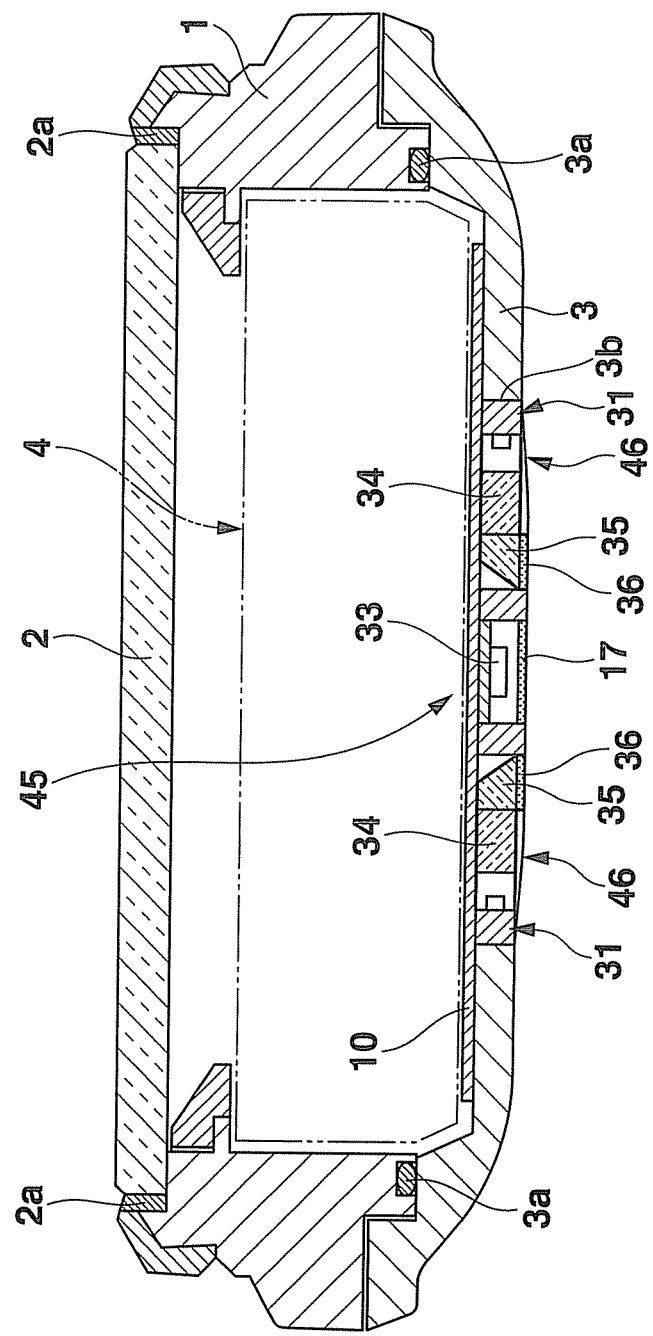
FIG. 15 is a schematic cross-sectional view of a body case of a wristwatch where an optical biological information detecting apparatus according to a third embodiment of the present invention is combined.
Figure 16:
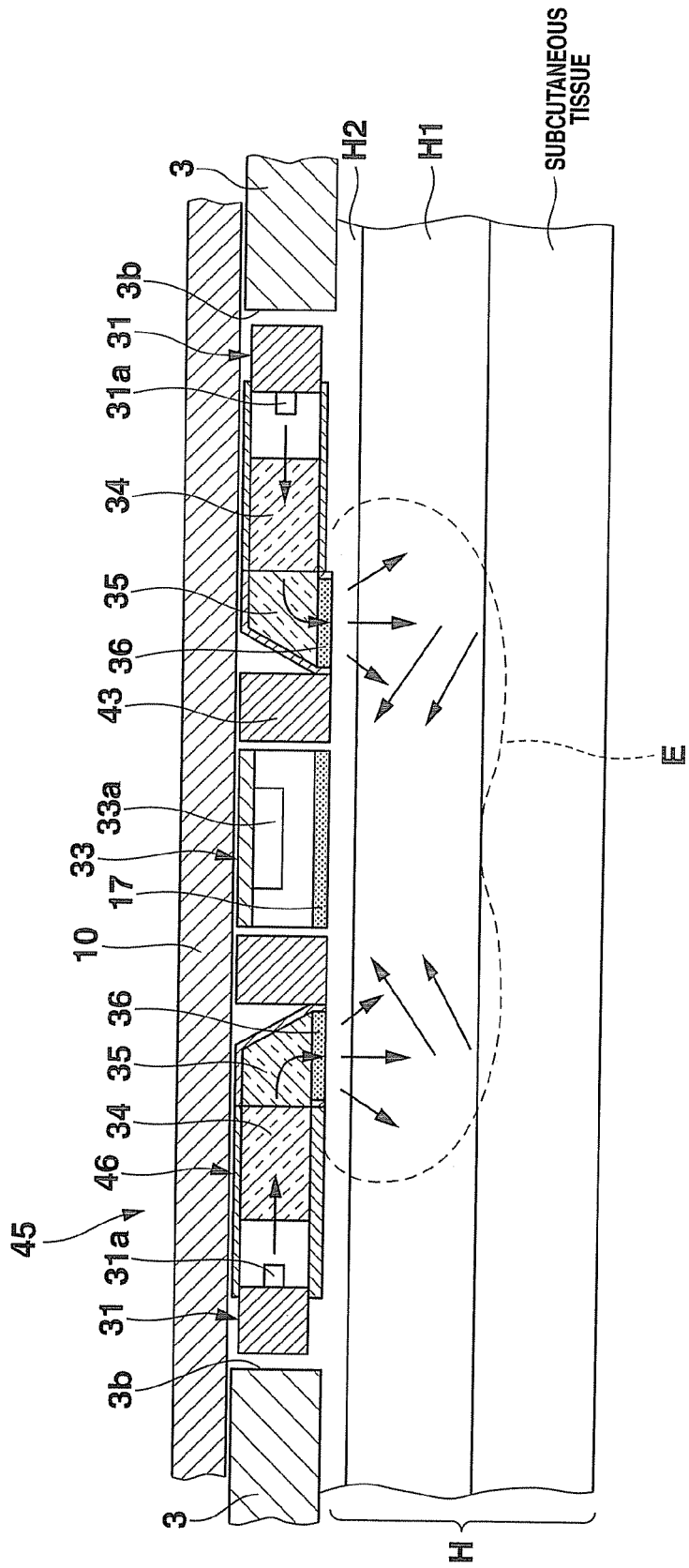
FIG. 16 is a cross-sectional view illustrating a state where biological information, such as a pulse wave, is optically measured while the back cover of the wristwatch illustrated in FIG. 15 contacts a skin of an arm.

As illustrated in FIGS. 15 and 16, the configuration of the wristwatch according to the third embodiment is different from the configuration of the wristwatch according to the second embodiment in that a biological information detecting apparatus 45 is provided in the mounting hole 3b provided in the back cover 3, and the other configuration thereof is almost the same as that of the second embodiment.

As illustrated in FIGS. 15 to 16, the biological information detecting apparatus 45 comprises light emitting units 31 that emit observation light of a specific wavelength band to optically observe a skin tissue of a human body, a light guide unit 46 that guides the observation light emitted from the light emitting units 31 and annularly diffuses and irradiates the observation light with respect to a skin H, and a light receiving unit 33 that is disposed in a place corresponding to the skin H positioned in a central portion of an annular irradiation area E where the observation light is irradiated by the light guide unit 46, and receives scattered light of the observation light irradiated onto the skin H.

In this case, the light emitting unit 31 and the light receiving unit 33 have the same configuration as that of the first embodiment. The light guide unit 46 is configured to contact the skin H, in a state where the light guide unit 46 is fitted into the mounting hole 3b of the back cover 3. That is, as illustrated in FIGS. 15 and 16, the light guide unit 46 comprises only a light guiding ring portion 34, a diffusion/reflection ring portion 35, and a diffusion ring portion 36.

The light guiding ring portion 34 is formed in a flat, almost square shape, using a material such as transparent glass or a transparent resin having a high light transmitting property, similar to the second embodiment. In the light guiding ring portion 34, a circular hole 34a is formed in a central portion thereof and incident surfaces 34b where the light emitting units 31 are disposed are formed in corner portions of four directions, respectively.

In the light guiding ring portion 34, an inner circumferential surface of the circular hole 34a of the central portion is formed in the emission surface 34c. Thereby, as illustrated in FIG. 16, the light guiding ring portion 34 is configured to take the observation light emitted from the light emitting unit 31 in the inner portion thereof from the incident surfaces 34b of the corner portions of the four directions, guide the taken observation light to the circular hole 34a of the central portion, and discharge the guided observation light from the emission surface 34c corresponding to the inner circumferential surface of the circular hole 34a.

Even in this case, as illustrated in FIG. 16, on an external surface of the light guiding ring portion 34, a first reflection layer 38 is provided by a metal vapor deposition method using aluminum or a plating method, except for the incident surfaces 34b of the corner portions and the emission surface 34c corresponding to the inner circumferential surface of the circular hole 34a. The first reflection layer 38 prevents the observation light, which is incident in the inner portion of the light guiding ring portion 34, from leaking to the outside of the light guiding ring portion 34.

Similar to the second embodiment, the diffusion/reflection ring portion 35 is also formed in an almost circular ring shape, using a synthetic resin such as a clouded or milky acrylic resin with a light diffusing property. The diffusion/reflection ring portion 35 is formed to have the same thickness as that of the light guiding ring portion 34, and is disposed in the circular hole 34a of the light guiding ring portion 34. In this case, the diffusion/reflection ring portion 35 is configured such that an outer circumferential surface thereof is formed in the incident surface 35a and the incident surface 35a thereof is disposed to adhere closely to the emission surface 34c corresponding to the inner circumferential surface of the circular hole 34a of the light guiding ring portion 34.

As illustrated in FIGS. 15 and 16, the bottom surface of the diffusion/reflection ring portion 35 is formed in the emission surface 35b that discharges the observation light taken from the incident surface 35a of the outer circumferential surface to the skin H. In the inner circumferential surface of the diffusion/reflection ring portion 35, a reflection surface 35c that reflects the observation light taken from the incident surface 35a of the outer circumferential surface to the emission surface 35b is formed to be annularly continuous. The reflection surface 35c is also formed in a portion of a reverse conical face, that is, a portion of the reverse conical face tapered toward the lower side.

As illustrated in FIG. 16, on an external surface of the diffusion/reflection ring portion 35, a second reflection layer 39 is provided by a metal vapor deposition method using aluminum or a plating method, except for the incident surfaces 35a of the outer circumferential surface and the emission surface 35b of the bottom surface. The second reflection layer 39 prevents the observation light, which is incident in the inner portion of the diffusion/reflection ring portion 35, from leaking to the outside of the diffusion/reflection ring portion 35 and optically isolates the light receiving unit 33.

Thereby, the diffusion/reflection ring portion 35 is configured to take the observation light discharged from the emission surface 34c of the light guiding ring portion 34 in the inner portion thereof from the incident surface 35a of the outer circumferential surface, diffuse the taken observation light while guiding the observation light along the annular shape of the diffusion/reflection ring portion 35, reflect the observation light to the emission surface 35b of the bottom surface by the reflection surface 35c provided in the inner circumferential portion, and discharge the diffused and reflected observation light from the emission surface 35b of the bottom surface to the lower side.

Similar to the second embodiment, the diffusion ring portion 36 is also formed in an almost circular ring shape, using a synthetic resin with a light diffusing property. The diffusion ring portion 36 is formed in a sheet shape having the small thickness, and is disposed to adhere closely to the emission surface 35b of the bottom surface of the diffusion/reflection ring portion 35. Similar to the diffusion/reflection ring portion 35, on each of the outer circumferential surface and the inner circumferential surface of the diffusion ring portion 36, a second reflection layer 39 that prevents the incident observation light from leaking to the outside of the diffusion ring portion 36 and optically isolates the light receiving unit 33 to be described below is provided by a metal vapor deposition method using aluminum or a plating method.

Thereby, as illustrated in FIG. 15, the diffusion ring portion 36 is configured to take the observation light discharged from the emission surface 35b of the diffusion/reflection ring portion 35 in the inner portion thereof from the top surface, sufficiently diffuse the taken observation light to become uniform while guiding the observation light along the annular shape of the diffusion ring portion 36, and uniformly discharge the diffused observation light from the bottom surface, such that the observation light is uniformly diffused and irradiated over the wide area of the ring shape, with respect to the skin H.

As illustrated in FIG. 16, the light receiving unit 33 is disposed in the central portion positioned at the inner circumferential side of the diffusion/reflection ring portion 35, in a state where the light receiving element 33a and the element substrate 33b are stored in a holder portion 43. On the bottom surface of the light receiving unit 33, an optical filter 17 is disposed. Similar to the first and second embodiments, the optical filter 17 is also configured to transmit light of a specific wavelength band of 900 nm or more and shield light of a wavelength band of 900 nm or less, such that the light receiving element 33a alleviates an influence from a measurement change due to external light such as sunlight.

Even in this case, the holder portion 43 of the light receiving unit 33 is formed of a metal with a light shielding property, such as aluminum, and its surface is subjected to alumite treatment to have a reflection function. Thereby, the light receiving element 33a can be optically protected. As illustrated in FIG. 16, the holder portion 43 is also formed to have the same thickness as that of the light emitting unit 31 (length of a vertical direction), and is disposed in a central portion of the diffusion/reflection ring portion 35.

Thereby, the light guide unit 46 and the light receiving unit 33 are formed to have the thicknesses within the thickness of the light emitting unit 31 (length of the vertical direction), and the top and bottom surfaces thereof are disposed on almost the same plane. In this state, the light guide unit 46 and the light receiving unit 33 are two-dimensionally disposed at the thickness of about 1 mm. The optical filter 17 is formed to have almost the same thickness as that of the diffusion ring portion 36 of the light guide unit 46, and is disposed on almost the same plane as the inner surface of the back cover 3 together with the diffusion ring portion 36.

Similar to the second embodiment, the circuit configuration of the biological information detecting apparatus 45 comprises a CPU (central processing unit) 20 that performs whole control of the apparatus, a photoelectric signal detecting module 26 comprising the light emitting unit 31 and the light receiving unit 33, a light emitting unit driving circuit 21 that drives the light emitting unit 31 of the photoelectric signal detecting module 26, an I/V converting circuit 22 that converts a current signal output from the light receiving unit 33 of the photoelectric signal detecting module 26 into a voltage signal, a display unit 23 that displays a measurement result of a biological tissue, such as a pulse wave, as the biological information, a power supply unit 24 that supplies a power supply voltage to the individual units, and a switch unit 25 operated by a user.

As illustrated in FIG. 30, a biological information detecting method of the biological information detecting apparatus 45 comprises a light emitting step S31 of causing the CPU 25 to emit observation light from the light emitting element 31a, an irradiating step S32 of annularly irradiating the observation light emitted by the light emitting step S31 onto the skin H by the light guide unit 46, a light receiving step S33 of scattering the observation light irradiated by the irradiating step S32 in the skin H and receiving the scattered light by the light receiving element 33a, and a biological information detecting step S34 of causing the CPU 25 to detect biological information, based on the scattered light received by the light receiving step S33.

As such, according to the biological information detecting apparatus 45, similar to the second embodiment, if the observation light of the specific wavelength band of $\lambda p=940$ nm is emitted by the light emitting unit 31, the observation light can be annularly diffused and irradiated onto the skin H by the light guide unit 46. Therefore, the observation light can be uniformly irradiated over the wide range of the skin H, and the scattered light of the observation light that is scattered in the skin H can be received by the light receiving unit 33 positioned in the central portion in the annular irradiation area E. As a result, the scattered light of the observation light can be efficiently and stably received by the light receiving unit 33.

For this reason, similar to the second embodiment, the observation light emitted from the light emitting unit 31 can be uniformly irradiated over the wide range of the skin H, and the light irradiation path through which the observation light emitted from the light emitting unit 31 is irradiated onto the skin H and the light reception path through which the scattered light of the observation light scattered in the skin H is received can be perfectly isolated by the first and second reflection layers 38 and 39. Therefore, the scattered light of the observation light that is diffused in and irradiated onto the skin H can be efficiently and stably received by the light receiving unit 33. Thereby, a biological tissue, such as a pulse wave, can be accurately measured.

In this case, the light guide unit 46 comprises the light guiding ring portion 34 that takes the observation light emitted from the light emitting unit 31 from the incident surface 34b of the side and guides the observation light to the circular hole 34a of the central portion, and the diffusion/reflection ring portion 35 that is disposed in the circular hole 34a of the light guiding ring portion 34, takes the observation light discharged from the emission surface 34c of the light guiding ring portion 34 from the incident surface 35a of the outer circumferential surface, and diffuses and reflects the observation light. Similar to the second embodiment, therefore, the observation light emitted from the light emitting unit 31 can be efficiently and securely diffused in and irradiated onto the skin H in an annular shape. As compared with the second embodiment, the size of the biological information detecting apparatus 45 can be further decreased.

That is, the plural light emitting units 31, the light guide unit 46, and the light receiving unit 33 have almost the same thickness and their top and bottom surfaces are parallel to each other and are two-dimensionally disposed on almost the same plane. In this state, the plural light emitting units 31, the light guide unit 46, and the light receiving unit 33 are formed to have almost the same thickness as that of the back cover 3. Therefore, the plural light emitting units 31, the light guide unit 46, and the light receiving unit 33 can be fitted into the mounting hole 3b of the back cover 3. Thereby, since the plural light emitting elements 31a, the light guide unit 46, and the light receiving element 33a can be two-dimensionally disposed within the same thickness, the size of the biological information detecting apparatus 45 can be further decreased and the wristwatch case 1 can be compacted.

Even in the biological information detecting apparatus 45, on the emission surface 35b of the diffusion/reflection ring portion 35, the diffusion ring portion 36 that takes the observation light discharged from the emission surface 35b and uniformly diffuses the observation light along an annular shape is provided. Therefore, when the observation light that is diffused and reflected by the diffusion/reflection ring portion 35 is taken by the diffusion ring portion 36 and the taken observation light is discharged from the bottom surface, the observation light can be uniformly irradiated onto the skin H along the annular shape without irregularity.

Even in the biological information detecting method, the light emitting element 31a of the light emitting unit 31 is made to emit the observation light, the emitted observation light is annularly irradiated onto the skin H by the light guiding ring portion 34 corresponding to the light guide unit 46, the diffusion/reflection ring portion 35, and the diffusion ring portion 36, the irradiated observation light is scattered in the skin H, the scattered light is taken by the scattered light taking unit 8 positioned in the central portion in the annular irradiation area E, the taken scattered light is received by the light receiving element 33a of the light receiving unit 33, and the biological information is detected. Therefore, the scattered light returned from the skin H among the observation light irradiated onto the skin H can be efficiently and stably received, and the biological information, such as the pulse wave, can be accurately detected.

That is, as illustrated in FIGS. 15 and 16, the biological information detecting apparatus 45 that executes the biological information detecting method comprises the light emitting element 31a that emits the observation light of the specific wavelength band to optically observe the skin tissue of the human body, the annular light guide unit 46 that guides the observation light emitted from the light emitting element 31a and annularly diffuses and irradiates the observation light with respect to the skin H, and the light receiving element 33*a* that is disposed to contact the skin H at the position of the central portion surrounded by the annular irradiation area E where the observation light is annularly irradiated by the annular light guide unit 46 and receives the scattered light scattered in the skin H.

In the biological information detecting apparatus 45 having the above configuration, the biological information detecting method according to the third embodiment comprises the light emitting step S31 of causing the light emitting unit 31*a* to emit the observation light, the irradiating step S32 of annularly irradiating the observation light emitted by the light emitting step S31 onto the skin H by the light guide unit 46, the light receiving step S33 of scattering the observation light irradiated by the irradiating step S32 in the skin H and receiving the scattered light by the light receiving element 33*a*, and the biological information detecting step S34 of detecting the biological information, based on the scattered light received by the light receiving step S33, as illustrated in FIG. 30.

According to the biological information detecting method having the above configuration, the light emitting element 31*a* is made to emit the observation light, the emitted observation light is annularly irradiated onto the skin H by the light guide unit 46, the irradiated observation light is scattered in the skin H, the scattered light is received by the light receiving element 33*a*, and the biological information can be accurately and easily detected based on the received scattered light.

In the second and third embodiments, the case where the light guiding ring portion 34 is formed in the flat, square shape, the circular hole 34*a* is provided in the central portion thereof, and the incident surfaces 34*b* are provided in the corner portions of the four directions, respectively, has been described, but the present invention is not limited thereto. For example, the light guiding ring portion 34 may be formed in a flat shape of a regular polygon, such as a regular triangle, a regular pentagon, and a regular hexagon, the circular hole may be provided in the central portion thereof, the incident surfaces may be provided in the corner portions, respectively, and the light emitting units 31 may be disposed to correspond to the incident surfaces.

Alternatively, the light guiding ring portion 34 may be formed in a flat shape, such as a circular shape or an elliptical shape, the circular hole may be provided in the central portion thereof, and the incident surfaces that the light emitting units 31 correspond to may be provided in the plural places of the outer circumferential surface, respectively.

Fourth Embodiment

Next, a fourth embodiment where the invention is applied to a wristwatch will be described with reference to FIGS. 17 to 29 and 31. Also in this case, the same components as those of the second embodiment illustrated in FIGS. 11 to 14 are denoted by the same reference numerals.

Figure 17:
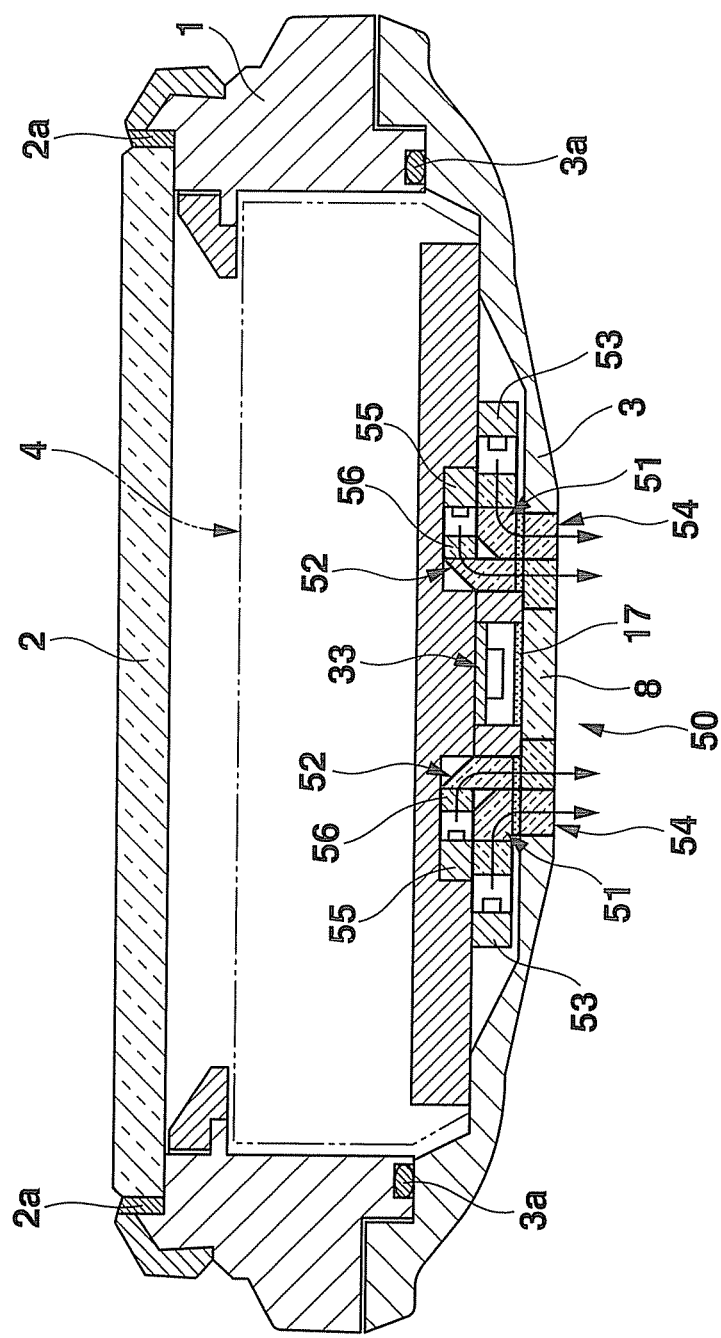
FIG. 17 is a schematic cross-sectional view of a body case of a wristwatch where an optical biological information detecting apparatus according to a fourth embodiment of the present invention is combined.

As illustrated in FIG. 17, the configuration of the wristwatch according to the fourth embodiment is different from the configuration of the wristwatch according to the second embodiment in that a biological information detecting apparatus 50 is provided in the central portion of the back cover 3 of the wristwatch case 1, and the other configuration thereof is almost the same as that of the second embodiment.

Figure 18:
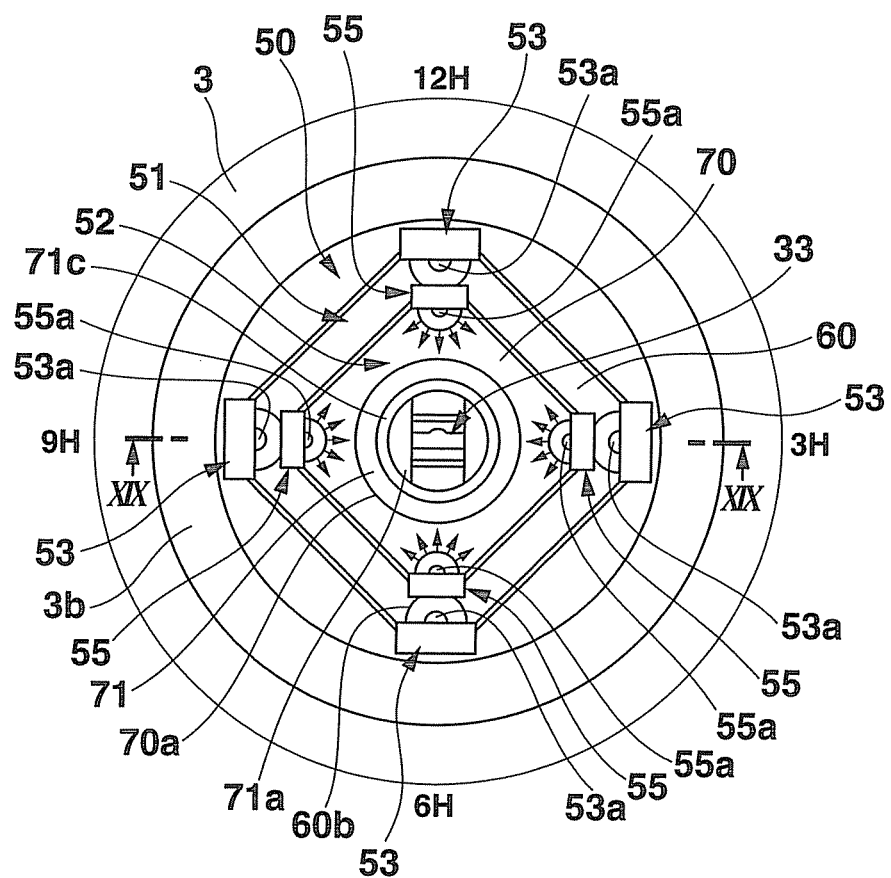
FIG. 18 is a plan view of a main portion of a back cover of the wristwatch of FIG. 17.
Figure 19:
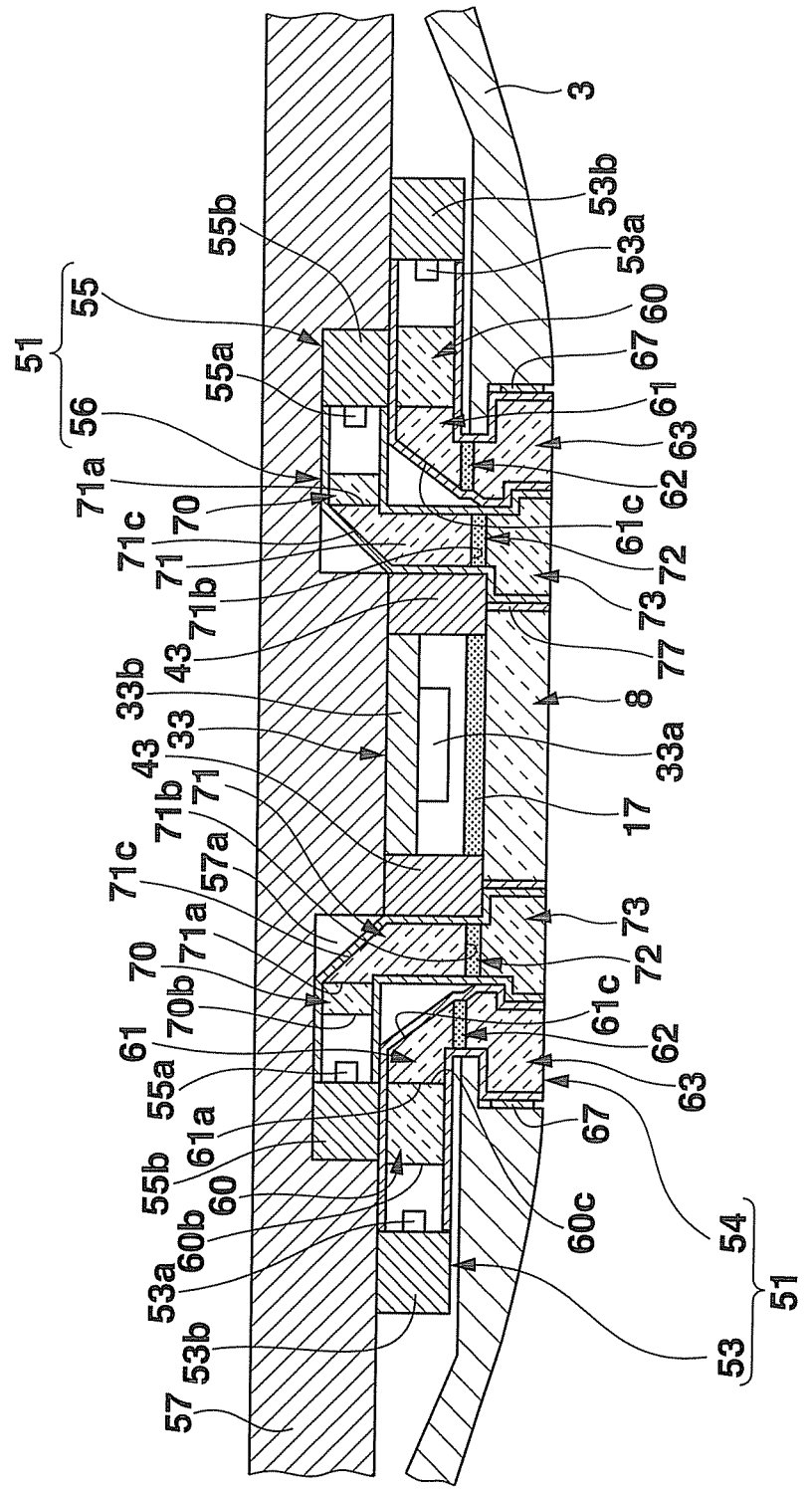
FIG. 19 is a cross-sectional view taken along a line XIX-XIX in FIG. 18.

As illustrated in FIGS. 17 to 19, the biological information detecting apparatus 50 comprises an outer circumferential side light irradiation path 51 through which observation light is irradiated onto a skin H, an inner circumferential side light irradiation path 52 through which the observation light is irradiated onto the skin H, a scattered light taking unit 8 that contacts the skin H positioned in a central portion of an annular irradiation area E1 where the observation light is irradiated by both or one of the outer circumferential side light irradiation path 51 and the inner circumferential side light irradiation path 52, and a light receiving unit 33 that is disposed in a place positioned at the side opposite to the skin H in the scattered light taking unit 8 and receives scattered light of the observation light taken by the scattered light taking unit 8.

Figure 20:
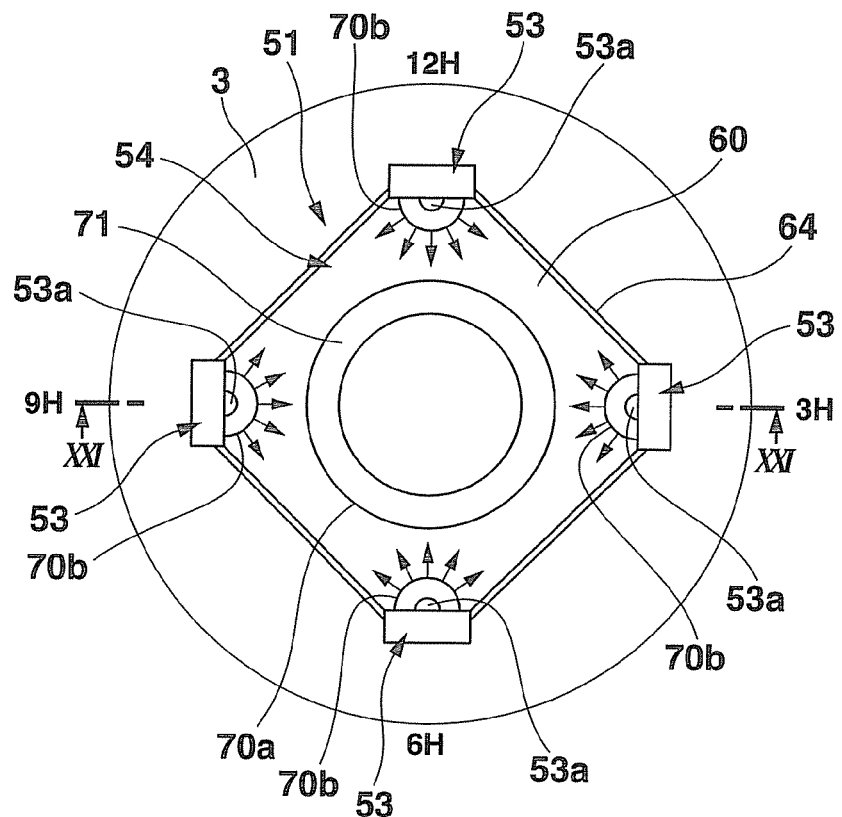
FIG. 20 is a schematic enlarged plan view of only an outer circumferential side light irradiating path of FIG. 18.
Figure 21:
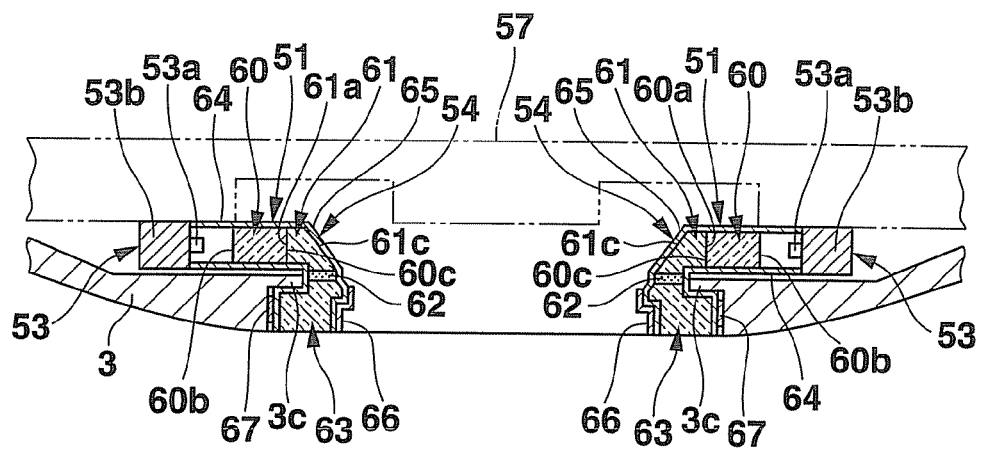
FIG. 21 is a cross-sectional view taken along a line XXI-XXI in FIG. 20.
Figure 22:
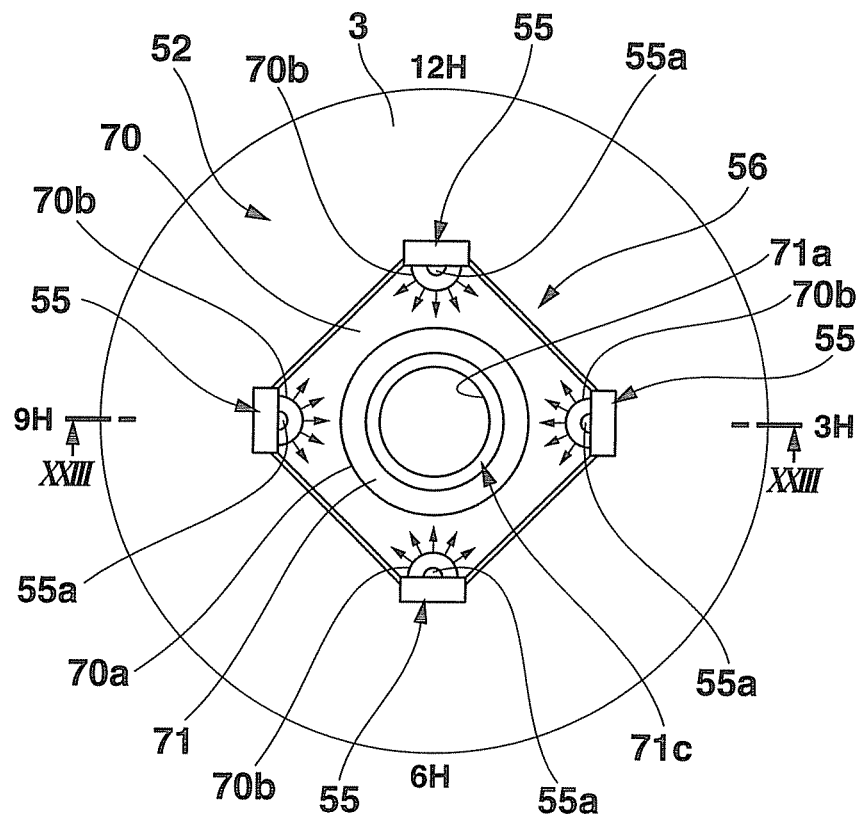
FIG. 22 is a schematic enlarged plan view of only an inner circumferential side light irradiating path of FIG. 18.
Figure 23:
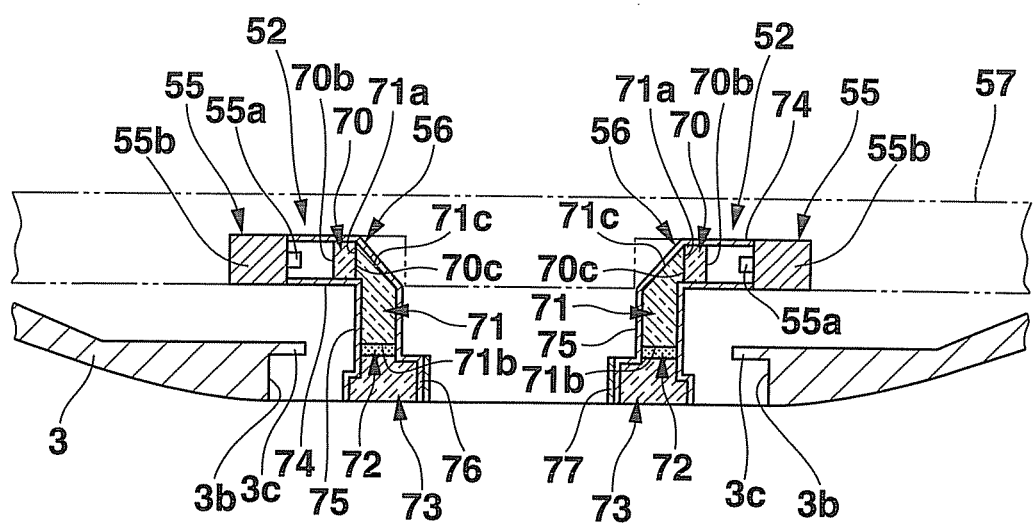
FIG. 23 is a cross-sectional view taken along a line XXIII-XXIII in FIG. 22.

As illustrated in FIGS. 19 to 21, the outer circumferential side light irradiation path 51 comprises a first light emitting portion 53 that emits observation light of a specific wavelength band to optically observe a skin tissue of a human body and a first light guide member 54 that guides the observation light emitted from the first light emitting portion 53 and annularly diffuses and irradiates the observation light with respect to the skin H. As illustrated in FIGS. 19, 22, and 23, the inner circumferential side light irradiation path 52 comprises a second light emitting portion 55 that emits observation light of a specific wavelength band to optically observe a skin tissue of a human body and a second light guide member 56 that guides the observation light emitted from the second light emitting portion 55 and annularly diffuses and irradiates the observation light with respect to the skin H positioned at the inner circumferential side of the irradiation area where the observation light is irradiated by the first light guide member 54. In this case, the first light emitting portion 53 and the second light emitting portion 55 are included in a light emitting unit. And, the first light guide member 54 and the second light guide member 56 are included in a light guide unit.

In this case, as illustrated in FIG. 19, the first light emitting portion 53 and the light receiving unit 33 are provided on a bottom surface of a circuit board 57 for measurement. The second light emitting portion 55 is disposed in a concave portion 57*a* that is formed in the bottom surface of the circuit board 57 in a ring shape. The circuit board 57 that is a multilayer wiring substrate is disposed in the wristwatch case 1, in a state where a wiring pattern is provided in the top and bottom surfaces and the concave portion 57*a* of the ring shape. Further, lower portions of the first and second light guide members 54 and 56 are fitted into the mounting hole 3*b* of the back cover 3, an upper portion of the first light guide member 54 is disposed on a bottom surface of the circuit board 10 in the wristwatch case 1, and an upper portion of the second light guide member 56 is disposed in the concave portion 57*a* having the ring shape in the circuit board 10 in the wristwatch case 1.

Meanwhile, similar to the second embodiment, each of the first and second light emitting portions 53 and 55 is of a side light emission type. As illustrated in FIG. 19, the first and second light emitting portions 53 and 55 have the configuration where first and second light emitting elements 53*a* and 55*a*, such as a light emitting diode (LED), are provided on sides of first and second element substrates 53*b* and 55*b*, respectively. The first and second light emitting elements 53*a* and 55*a* are configured to emit infrared light ($\lambda p=940$ nm) where absorbance of melanine pigment contained in the skin H is low as the observation light.

In this case, as illustrated in FIGS. 19 to 21, the first light emitting portions 53 of the outer circumferential side light irradiation path 51 are provided in four places corresponding to four directions of the 12 o'clock side, the 3 o'clock side, the 6 o'clock side, and the 9 o'clock side in a bottom surface of the circuit board 57 corresponding to the outer circumference of the first light guide member 54, respectively. As illustrated in FIGS. 19 to 21, the first light guide member 54 comprises a first light guiding ring portion 60, a first diffusion/reflection ring portion 61, a first diffusion ring portion 62, and a first diffusion/irradiation ring portion 63.

The first light guiding ring portion 60 is made of a material, such as transparent glass or a transparent resin having a high light transmitting property, and is formed in a flat, almost square shape, similar to the second embodiment. In the first light guiding ring portion 60, a circular hole 60a is formed in a central portion thereof and incident surfaces 60b where the first light emitting portions 53 are disposed are formed in corner portions, respectively. In this case, the first light guiding ring portion 60 is disposed on the bottom surface of the circuit board 57, such that the incident surfaces 60b of the corner portions correspond to the four directions of the 12 o'clock direction, the a 3 o'clock direction, the 6 o'clock direction, and the 9 o'clock direction.

That is, as illustrated in FIG. 18, the incident surface 60b of the first light guiding ring portion 60 is a notched concave portion that is formed by biting each corner portion of the first light guiding ring portion 60 in a semicircular shape, and the first light emitting element 53a of the first light emitting portion 53 is inserted into the notched concave portion having the semicircular shape. Thereby, the first light guiding ring portion 60 is configured such that the observation light emitted from the first light emitting element 53a is incident radially from the four directions, toward the circular hole 60a of the central portion from the four corner portions of the first light guiding ring portion 60.

As illustrated in FIGS. 19 and 21, in the first light guiding ring portion 60, an inner circumferential surface of the circular hole 60a of the central portion is formed in the emission surface 60c. Thereby, as illustrated in FIGS. 19 and 21, the first light guiding ring portion 60 is configured to take the observation light emitted from the first light emitting portion 53 in the inner portion thereof from the incident surfaces 60b of the corner portions of the four directions, guide the taken observation light from the four directions to the circular hole 60a of the central portion, and discharge the guided observation light from the emission surface 60c corresponding to the inner circumferential surface of the circular hole 60a.

In this case, as illustrated in FIGS. 19 and 21, on an external surface of the first light guiding ring portion 60, a first reflection layer 64 is provided by a metal vapor deposition method using aluminum or a plating method, except for the incident surfaces 60b of the corner portions and the emission surface 60c corresponding to the inner circumferential surface of the circular hole 60a. The first reflection layer 64 prevents the observation light, which is incident in the inner portion of the first light guiding ring portion 60, from leaking to the outside of the first light guiding ring portion 60.

As illustrated in FIGS. 19 to 21, the first diffusion/reflection ring portion 61 is formed in an almost circular ring shape, using a synthetic resin such as a clouded or milky acrylic resin with a light diffusing property. The first diffusion/reflection ring portion 61 is formed to have almost the same thickness as that of the first light guiding ring portion 60, and is disposed in the circular hole 60a of the first light guiding ring portion 60. In this case, the first diffusion/reflection ring portion 61 is configured such that an outer circumferential surface thereof is formed in the incident surface 61a and the incident surface 61a thereof is disposed to adhere closely to the emission surface 60c corresponding to the inner circumferential surface of the circular hole 60a of the first light guiding ring portion 60.

As illustrated in FIGS. 18 to 22, the bottom surface of the first diffusion/reflection ring portion 61 is formed in the emission surface 61b that discharges the observation light taken from the incident surface 61a of the outer circumferential surface to the skin H. In the inner circumferential surface of the first diffusion/reflection ring portion 61, a reflection surface 61c that reflects the observation light taken from the incident surface 61a of the outer circumferential surface to the emission surface 61b of the bottom surface is formed to be annularly continuous, as illustrated in FIG. 21. The reflection surface 61c is formed in a portion of a reverse conical face, that is, a portion of the reverse conical face tapered toward the lower side.

As illustrated in FIGS. 19 and 21, on an external surface of the first diffusion/reflection ring portion 61, a second reflection layer 65 is provided by a metal vapor deposition method using aluminum or a plating method, except for the incident surfaces 61a of the outer circumferential surface and the emission surface 61b of the bottom surface. The second reflection layer 65 prevents the observation light, which is incident in the inner portion of the first diffusion/reflection ring portion 61, from leaking to the outside of the first diffusion/reflection ring portion 61 and optically isolates the light receiving unit 33 to be described below.

Thereby, the first diffusion/reflection ring portion 61 is configured to take the observation light discharged from the emission surface 60c corresponding to the inner circumferential surface of the first light guiding ring portion 60 in the inner portion thereof from the incident surface 61a of the outer circumferential surface, diffuse the taken observation light while guiding the observation light along the annular shape of the first diffusion/reflection ring portion 61, reflect the observation light to the emission surface 61b of the bottom surface by the reflection surface 61c provided in the inner circumferential surface, and discharge the diffused and reflected observation light from the emission surface 61b of the bottom surface to the lower side, as illustrated in FIGS. 19 and 21.

As illustrated in FIGS. 19 and 21, the first diffusion ring portion 62 is formed in an almost circular ring shape, using a synthetic resin with a light diffusing property. The first diffusion ring portion 62 is formed in a sheet shape having the small thickness, and is disposed to adhere closely to the emission surface 61b of the bottom surface of the first diffusion/reflection ring portion 61. Similar to the first diffusion/reflection ring portion 61, on each of the outer circumferential surface and the inner circumferential surface of the first diffusion ring portion 62, the second reflection layer 65 that prevents the incident observation light from leaking to the outside of the first diffusion ring portion 62 and optically isolates the light receiving unit 33 to be described below is provided by a metal vapor deposition method using aluminum or a plating method.

Thereby, as illustrated in FIGS. 19 and 21, the first diffusion ring portion 62 is configured to take the observation light discharged from the emission surface 61b of the first diffusion/reflection ring portion 61 in the inner portion thereof from the top surface, sufficiently diffuse the taken observation light to become uniform while guiding the observation light along the annular shape of the first diffusion ring portion 62, and uniformly discharge the diffused observation light from the bottom surface to the skin H without irregularity.

As illustrated in FIGS. 19 and 21, the first diffusion/irradiation ring portion 63 is formed in an almost circular ring shape, using a synthetic resin such as an acrylic resin with diffuseness. The first diffusion/irradiation ring portion 63 is disposed on the lower side of the first diffusion/reflection ring portion 61 through the first diffusion ring portion 62 and is fitted into the mounting hole 3b of the back cover 3 through the first waterproof packing 67. In this case, the first diffusion/irradiation ring portion 63 is formed such that the outer circumferential surface thereof is slightly lager than the outer circumferential surface of the first diffusion/reflection ring portion 61 and the inner circumferential surface thereof is almost equal to the inner circumferential surface of the first diffusion/reflection ring portion 61.

Thereby, the first diffusion/irradiation ring portion 63 is configured to take the observation light discharged from the first diffusion/reflection ring portion 61 and diffused annularly without irregularity in the first diffusion ring portion 62 from the top surface, further diffuse the taken observation light, annularly discharge the diffused observation light from the bottom surface, and uniformly diffuse and irradiate the observation light over the wide area of the ring shape, with respect to the skin H in the place slightly away from the outer circumference of the scattered light taking unit 8.

Even in this case, as illustrated in FIGS. 19 and 21, on the outer circumferential surface and the inner circumferential surface of the first diffusion/irradiation ring portion 63, a third reflection layer 66 is provided by a metal vapor deposition method using aluminum or a plating method, except for the top surface and the bottom surface. The third reflection layer 66 prevents the observation light, which is incident in the inner portion of the first diffusion/irradiation ring portion 63, from leaking to the outside of the first diffusion/irradiation ring portion 63 and optically isolates the light receiving portion 33 to be described below.

The position of the first diffusion/irradiation ring portion 63 is regulated such that the first diffusion/irradiation ring portion comes into contact with a protrusion portion 3c provided in the mounting hole 3b of the back cover 3 and is not pressed into the wristwatch case 1. In this case, as illustrated in FIGS. 19 and 21, the bottom surface of the first diffusion/irradiation ring portion 63 is disposed at the same height as that of a lowermost portion in the bottom surface of the back cover 3. Thereby, the first diffusion/irradiation ring portion 63 contacts the skin H together with the bottom surface of the back cover 3 without generating a step by the bottom surface of the first diffusion/irradiation ring portion 63 and the bottom surface of the back cover 3.

Meanwhile, as illustrated in FIGS. 19, 22, and 23, the second light emitting portions 55 in the inner circumferential side light irradiation path 52 that is disposed on the inner circumferential side of the outer circumferential side light irradiation path 51 are provided in four places corresponding to four directions of the 12 o'clock side, the 3 o'clock side, the 6 o'clock side, and the 9 o'clock side in the concave portion 57a provided in the ring shape in a bottom surface of the circuit board 57 corresponding to the outer circumference of the second light guide member 56, respectively. As illustrated in FIGS. 19, 22, and 23, the second light guide member 56 comprises a second light guiding ring portion 70, a second diffusion/reflection ring portion 71, a second diffusion ring portion 72, and a second diffusion/irradiation ring portion 73.

Similar to the first light guiding ring portion 60, the second light guiding ring portion 70 is made of a material such as transparent glass or a transparent resin having a high light transmitting property, and is formed in a flat, almost square shape, having a size smaller than that of the first light guiding ring portion 60. In the second light guiding ring portion 70, a circular hole 70a is formed in a central portion thereof and incident surfaces 70b where the second light emitting portions 55 are disposed are formed in corner portions, respectively. In this case, the second light guiding ring portion 70 is disposed in the concave portion 57a of the circuit board 57 in a state where the second light guiding ring portion is positioned on the first diffusion/reflection ring portion 61, such that the incident surfaces 70b of the corner portions correspond to the four directions of the 12 o'clock side, the 3 o'clock side, the 6 o'clock side, and the 9 o'clock side.

That is, as illustrated in FIGS. 18 and 22, the incident surface 70b of the second light guiding ring portion 70 is a notched concave portion that is formed by biting each corner portion of the second light guiding ring portion 70 in a semicircular shape, and the second light emitting element 55a of the second light emitting portion 55 is inserted into the notched concave portion having the semicircular shape. Thereby, the second light guiding ring portion 70 is configured such that the observation light emitted from the second light emitting element 55a is incident radially from the four directions, toward the circular hole 70a of the central portion from the four corner portions of the second light guiding ring portion 70.

In the second light guiding ring portion 70, in an inner circumferential surface of the circular hole 70a of the central portion, the emission surface 70c that discharges the observation light taken from the incident surface 70b of the outer circumferential surface is formed. Thereby, as illustrated in FIGS. 21 and 22, the second light guiding ring portion 70 is configured to take the observation light emitted from the second light emitting portion 55 in the inner portion thereof from the incident surfaces 70b of the corner portions of the four directions, guide the taken observation light from the four directions to the circular hole 70a of the central portion, and discharge the guided observation light from the emission surface 70c corresponding to the inner circumferential surface of the circular hole 70a.

In this case, as illustrated in FIGS. 19 and 23, on an external surface of the second light guiding ring portion 70, a fourth reflection layer 74 is provided by a metal vapor deposition method using aluminum or a plating method, except for the incident surfaces 70b of the corner portions and the emission surface 70c of the bottom surface. The fourth reflection layer 74 prevents the observation light, which is incident in the inner portion of the second light guiding ring portion 70, from leaking to the outside of the second light guiding ring portion 70.

As illustrated in FIGS. 19, 22, and 23, the second diffusion/reflection ring portion 71 is formed in an almost circular ring shape, using a synthetic resin such as a clouded or milky acrylic resin with a light diffusing property. The second diffusion/reflection ring portion 71 is formed to have almost the same thickness as the thickness obtained when the first light guiding ring portion 60 and the first diffusion/reflection ring portion 61 are overlapped, and is disposed on the inner circumference of the first diffusion/reflection ring portion 61, in a state where the upper portion of the outer circumferential surface thereof corresponds to the emission surface 70c of the second light guiding ring portion 70.

As illustrated in FIGS. 19 and 23, the second diffusion/reflection ring portion 71 is configured such that the upper portion of the outer circumferential surface is formed in the incident surface 71a, the bottom surface is formed in the emission surface 71b, and the observation light taken from the incident surface 71a is discharged to the skin H. In the inner circumferential surface of the second diffusion/reflection ring portion 71, a reflection surface 71c that reflects the observation light taken from the incident surface 71a of the outer circumferential surface to the emission surface 71b of the bottom surface is formed to be annularly continuous, as illustrated in FIG. 23. The reflection surface 71c is formed in a portion of a reverse conical face, that is, a portion of the reverse conical face tapered toward the lower side.

As illustrated in FIGS. 19 and 23, on an external surface of the second diffusion/reflection ring portion 71, a fifth reflection layer 75 is provided by a metal vapor deposition method using aluminum or a plating method, except for the incident surfaces 71a of the top surface and the emission surface 71b of the bottom surface. The fifth reflection layer 75 prevents the observation light, which is incident in the inner surface of the second diffusion/reflection ring portion 71, from leaking to the outside of the second diffusion/reflection ring portion 71 and optically isolates the light receiving unit 33 to be described below.

As illustrated in FIGS. 19 and 23, the second diffusion ring portion 72 is formed in an almost circular ring shape, using a synthetic resin with a light diffusing property. The second diffusion ring portion 72 is formed in a sheet shape having the small thickness, and is disposed to adhere closely to the emission surface 71b of the bottom surface of the second diffusion/reflection ring portion 71. Similar to the second diffusion/reflection ring portion 71, on each of the outer circumferential surface and the inner circumferential surface of the second diffusion ring portion 72, the fifth reflection layer 75 that prevents the incident observation light from leaking to the outside of the second diffusion ring portion 72 and optically isolates the light receiving unit 33 to be described below is provided by a metal vapor deposition method using aluminum or a plating method.

Thereby, as illustrated in FIGS. 19 and 23, the second diffusion ring portion 72 is configured to take the observation light discharged from the emission surface 71b of the second diffusion/reflection ring portion 71 in the inner portion thereof from the top surface, sufficiently diffuse the taken observation light to become uniform while guiding the observation light along the annular shape of the second diffusion ring portion 72, and uniformly discharge the diffused observation light from the bottom surface to the skin H without irregularity.

As illustrated in FIGS. 19 and 23, the second diffusion/irradiation ring portion 73 is formed in an almost circular ring shape, using a synthetic resin such as an acrylic resin with diffuseness. The second diffusion/irradiation ring portion 73 is disposed on the lower side of the second diffusion/reflection ring portion 71 through the second diffusion ring portion 72 and the outer circumferential surface of the second diffusion/irradiation ring portion 73 is disposed to adhere closely to the inner circumferential surface of the first diffusion/irradiation ring portion 63. In this case, the second diffusion/irradiation ring portion 73 is formed such that the lower portion of the outer circumferential surface is slightly larger than the lower portion of the inner circumferential surface of the first diffusion/irradiation ring portion 63.

Thereby, the second diffusion/irradiation ring portion 73 is configured to take the observation light discharged from the second diffusion/reflection ring portion 71 and annularly diffused without irregularity in the second diffusion ring portion 72 from the top surface, further diffuse the taken observation light, annularly discharge the diffused observation light from the bottom surface, and uniformly diffuse and irradiate the observation light over the wide area of the ring shape, with respect to the skin H in the place positioned between the outer circumference of the scattered light taking unit 8 and the inner circumference of the first diffusion/irradiation ring portion 63.

Even in this case, as illustrated in FIGS. 19 and 23, on the outer circumferential surface and the inner circumferential surface of the second diffusion/irradiation ring portion 73, a sixth reflection layer 76 is provided by a metal vapor deposition method using aluminum or a plating method, except for the top surface and the bottom surface. The sixth reflection layer 76 prevents the observation light, which is incident in the inner portion of the second diffusion/irradiation ring portion 73, from leaking to the outside of the second diffusion/irradiation ring portion 73 and optically isolates the light receiving portion 33 to be described below.

The position of the second diffusion/irradiation ring portion 73 is regulated such that a convex portion of the upper portion in the outer circumferential portion of the second diffusion/irradiation ring portion 73 comes into contact with the concave portion of the lower portion in the inner circumferential surface of the first diffusion/irradiation ring portion 63 coming into contact with a protrusion portion 3c provided in the mounting hole 3b of the back cover 3 and the second diffusion/irradiation ring portion is not pressed into the wristwatch case 1. In this case, as illustrated in FIGS. 19 and 23, the bottom surface of the second diffusion/irradiation ring portion 73 is disposed at the same height as that of a lowermost portion in the bottom surface of the back cover 3. Thereby, the second diffusion/irradiation ring portion 73 contacts the skin H together with the bottom surface of the back cover 3 without generating a step by the bottom surface of the second diffusion/irradiation ring portion 73 and the bottom surface of the back cover 3.

As illustrated in FIGS. 19 and 24 to 26, in the second diffusion/irradiation ring portion 73, the scattered light taking unit 8 that takes the scattered light of the observation light irradiated onto the skin H is provided. The scattered light taking unit 8 is also formed in a circular flat shape, using a material such as transparent glass or a transparent resin with a high refractive index, similar to the second embodiment. In this case, the scattered light taking unit 8 is formed to have almost the same thickness as that of the second diffusion/irradiation ring portion 73. Thereby, the top surfaces and the bottom surfaces of the scattered light taking unit 8 and the first and second diffusion/irradiation ring portions 63 and 73 are disposed on almost the same plane.

As illustrated in FIGS. 19 and 24 to 26, the scattered light taking unit 8 is mounted in the second diffusion/irradiation ring portion 73 between the outer circumferential surface thereof and the inner circumferential surface of the second diffusion/irradiation ring portion 73 through a second waterproof packing 77. The scattered light taking unit 8 is configured to contact the skin H positioned in a central portion of an irradiation area E1 having a ring shape where a bottom surface is irradiated with the observation light by the first and second diffusion/irradiation ring portions 63 and 73. Thereby, the scattered light taking unit 8 is configured to take the scattered light of the observation light irradiated onto the skin H from the bottom surface and irradiate the taken scattered light from the top surface to the light receiving unit 33.

Similar to the second embodiment, the light receiving unit 33 receives the scattered light of the observation light taken by the scattered light taking unit 8 and performs photoelectric conversion. The light receiving unit 33 has the configuration where the light receiving element 33a, such as a silicon photo diode, is provided downward on the bottom surface of the element substrate 33b. As illustrated in FIGS. 19 and 24 to 26, the light receiving unit 33 is provided on the bottom surface of the circuit board 57 in the place positioned at the side (upper side in FIG. 19) opposite to the skin H in the scattered light taking unit 8, that is, the place positioned in the vicinity of the focal position on an optical axis of the scattered light taking unit 8, in a state where the light receiving element 33a is stored in a holder portion 43.

Similar to the second embodiment, the light receiving element 33a of the light receiving unit 33 has a spectral sensitivity characteristic of reacting strongest with light of a specific wavelength band of about λ=940 nm. That is, the light receiving element 33a is configured such that light reception sensitivity is gradually lowered as the wavelength becomes short with respect to light of a wavelength band of 940 nm or less, is rapidly lowered with respect to light of a wavelength band of 940 nm or more, and becomes highest with respect to light having a wavelength of 940 nm.

As illustrated in FIGS. 19 and 24 to 26, at the lower side of the light receiving element 33a, that is, between the light receiving element 33a and the scattered light taking unit 8, an optical filter 17 is disposed in the holder portion 43 positioned on the lower side of the light receiving element 33a. Similar to the second embodiment, the optical filter 17 is configured to transmit light of a specific wavelength band of 900 nm or more and shield light of a wavelength band of 900 nm or less, such that the light receiving element 33a alleviates an influence from a measurement change due to external light such as sunlight.

In this case, the holder portion 43 of the light receiving unit 33 is formed of a metal with a light shielding property, such as aluminum, and its surface is subjected to alumite treatment to have a reflection function. Thereby, the light receiving element 33a can be optically protected. As illustrated in FIGS. 19 and 24 to 26, the holder portion 43 is formed to have the same thickness as that of the first light emitting portion 53 (length of a vertical direction), and is disposed in a central portion of the first and second diffusion/reflection ring portions 61 and 71.

Figure 27:
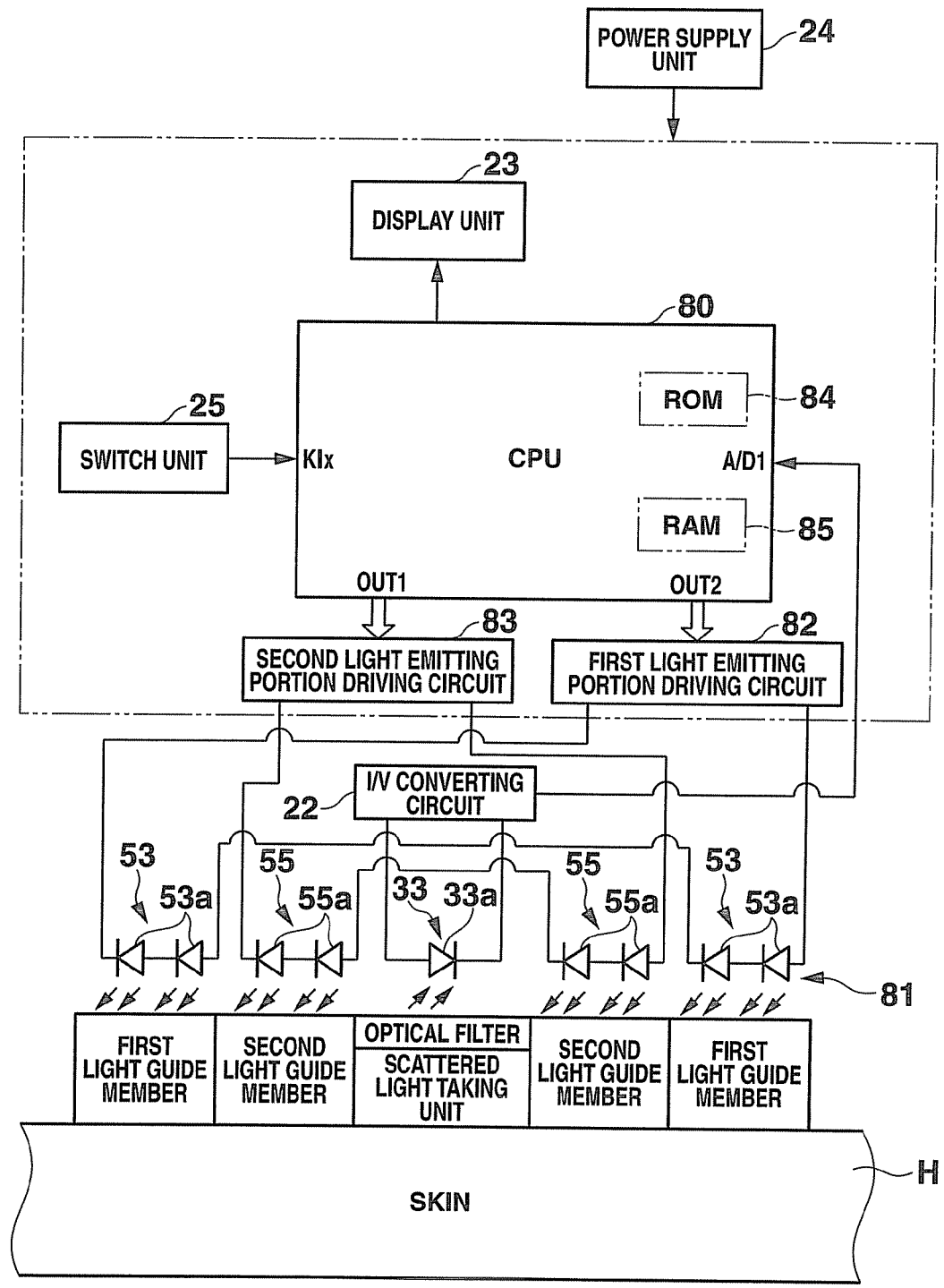
FIG. 27 is a block diagram illustrating a configuration of a circuit of the optical biological information detecting apparatus according to the fourth embodiment of the present invention.

Next, the circuit configuration of the biological information detecting apparatus 50 will be described with reference to a block diagram illustrated in FIG. 27.

Similar to the first embodiment, the circuit configuration of the biological information detecting apparatus 50 comprises a CPU (central processing unit) 80 that performs whole control of the apparatus and a photoelectric signal detecting module 81 comprising the light emitting unit of the first and second light emitting portions 53 and 55 and the light receiving unit 33.

The circuit configuration of the biological information detecting apparatus 50 further comprises the first light emitting portion driving circuit 82 that drives the first light emitting element 53a in the first light emitting portion 53 of the photoelectric signal detecting module 81, a second light emitting portion driving circuit 83 that drives a second light emitting element 55a in the second light emitting portion 55 of the photoelectric signal detecting module 81, the 1I/V converting circuit 22 that converts a current signal output from the light receiving element 33a in the light receiving unit 33 of the photoelectric signal detecting module 81 into a voltage signal, the display unit 23 that displays a measurement result of a biological tissue, such as a pulse wave, as biological information, the power supply unit 24 that supplies a power supply voltage to the individual units, and the switch unit 25 operated by a user.

The CPU 80 comprises a read only memory (ROM) 84 and a random access memory (RAM) 85. The photoelectric signal detecting module 81 comprises the first and second light emitting elements 53a and 55a that emit the observation light of a specific wavelength band and the light receiving element 33a that receives the scattered light of the observation light, when the observation light emitted from the first and second light emitting elements 53a and 55a is irradiated onto the skin H and is scattered in the skin H, and outputs a current signal according to the amount of received light.

The power supply unit 24 supplies power to the CPU 80 and the first and second light emitting portion driving circuits 82 and 83, and the supply of power to the circuit block other than the CPU 80 is controlled by the CPU 80. The four first and second light emitting elements 53a and 55a disposed in the four places of the 12 o'clock side, the 3 o'clock side, the 6 o'clock side, and the 9 o'clock side are connected in series.

If the operation signal from the switch unit 25 is input from a KIx port, the CPU 80 selectively outputs driving signals to the first and second light emitting portion driving circuits 82 and 83 from an OUT1 port and an OUT2 port, continuously controls driving of the first and second light emitting elements 53a and 55a with a constant voltage pulse for a constant time with a constant period, and emits light from the first and second light emitting elements 53a and 55a with constant light intensity.

That is, first, the CPU 80 simultaneously outputs the driving signals to the first and second light emitting portion driving circuits 82 and 83, continuously controls driving of the first and second light emitting elements 53a and 55a with a constant voltage pulse for a constant time with a constant period, and simultaneously emits light from the first and second light emitting elements 53a and 55a with constant light intensity. After that, the CPU 80 outputs the driving signal to only the first light emitting portion driving circuit 82, controls driving of only the first light emitting element 53 with a constant voltage pulse for a constant time with a constant period, and emits light only from the first light emitting element 53a with constant light intensity.

If the observation light emitted from the first and second light emitting elements 53a and 55a is irradiated onto the skin H and the scattered light thereof is received by the light receiving element 33a, the light receiving element 33a outputs a current signal according to the amount of received light. The I/V converting circuit 22 converts the current signal output from the light receiving element 33a into a voltage signal and inputs the signal to an A/D1 port of the CPU 80. The CPU 80 converts the voltage signal, which is input to the A/D1 port, into a digital signal by an incorporated A/D converter at predetermined timing of the constant current pulse during a driving period and stores the signal as time-series data in the RAM 85.

That is, when the CPU 80 causes both the first and second light emitting elements 53a and 55a to emit light, the light receiving element 33a receives the scattered light of the observation light and stores the voltage signal converted by the I/V converting circuit 22 in the RAM 85 as first time-series data. When the CPU 80 causes only the first light emitting element 53a to emit the light, the light receiving element 33a receives the scattered light of the observation light and stores the voltage signal converted by the I/V converting circuit 22 in the RAM 85 as second time-series data.

The CPU 80 performs a frequency analysis on the first and second time-series data and performs an operation. The CPU 80 calculates data that corresponds to third time-series data corresponding to an irradiation area E3 illustrated in FIG. 26, stores the data as biological information such as a pulse wave in the RAM 85, outputs the data to the display unit 23, and displays the data on the display unit 23.

Next, a biological information detecting method in the biological information detecting apparatus 50 will be described with reference to FIG. 31.

The biological information detecting method comprises a first measuring step S41 of causing the first and second light emitting elements 53a and 55a to simultaneously emit observation light, irradiating the observation light onto the skin H by the outer circumferential side light irradiation path 51 and the inner circumferential side light irradiation path 52, taking the scattered light of the irradiated observation light in the skin H by the scattered light taking unit 8, receiving the taken scattered light by the light receiving element 33*a*, and detecting the first biological information based on the received scattered light.

The biological information detecting method further comprises a second measuring step S42 of causing only the first light emitting element 53*a* to emit observation light, irradiating the observation light onto the skin H by the outer circumferential side light irradiation path 51, taking the scattered light of the irradiated observation light in the skin H by the scattered light taking unit 8, receiving the taken scattered light by the light receiving element 33*a*, and detecting the second biological information based on the received scattered light, and an operating step S43 of operating the first biological information detected by the first measuring step S41 and the second biological information detected by the second measuring step S42 and calculating biological information unique to a measurer.

Next, a function of the biological information detecting apparatus 50 will be described.

The wristwatch case 1 is previously mounted on the arm and the bottom surface of the back cover 3 is made to contact the skin H of the arm, as illustrated in FIG. 17. At this time, the bottom surface of the back cover 3 is moderately curved and protruded. However, the bottom surface of each of the first diffusion/irradiation ring portion 63 of the outer circumferential side light irradiation path 51, the second diffusion/irradiation ring portion 73 of the inner circumferential side light irradiation path 52, and the scattered light taking unit 8 in the biological information detecting apparatus 50 is formed to become a flat surface, and the flat surfaces are disposed on the same plane without a step. Thereby, the flat surfaces of the first and second diffusion/irradiation ring portions 63 and 73 and the scattered light taking unit 8 equally contact the surface of the skin H of the arm.

In this state, if the switch unit 25 is operated and a measurement start command is given to the CPU 80, first, the CPU 80 outputs driving signals to the first and second light emitting portion driving circuits 82 and 83, and the first and second light emitting portion driving circuits 82 and 83 continuously output a constant current pulse to the first and second light emitting elements 53*a* and 55*a* for a predetermined time with a constant period and simultaneously control the driving of the first and second light emitting elements 53*a* and 55*a*.

After the driving of the first and second light emitting elements 53*a* and 55*a* is simultaneously controlled, the CPU 80 outputs the driving signal to only the first light emitting portion driving circuit 82, and only the first light emitting portion driving circuit 82 continuously outputs a constant current pulse to the first light emitting element 53*a* for a constant time with a constant period, and controls the driving of the first light emitting element 53*a*.

While the driving is controlled as described above, the first and second light emitting elements 53*a* and 55*a* stably emit the observation light with constant light intensity. At this time, if the first and second light emitting elements 53*a* and 55*a* are driven by the first and second light emitting portion driving circuits 82 and 83, respectively, the first and second light emitting elements 53*a* and 55*a* emit light of an infrared band of $\lambda p=940$ nm as the observation light.

Figure 24:
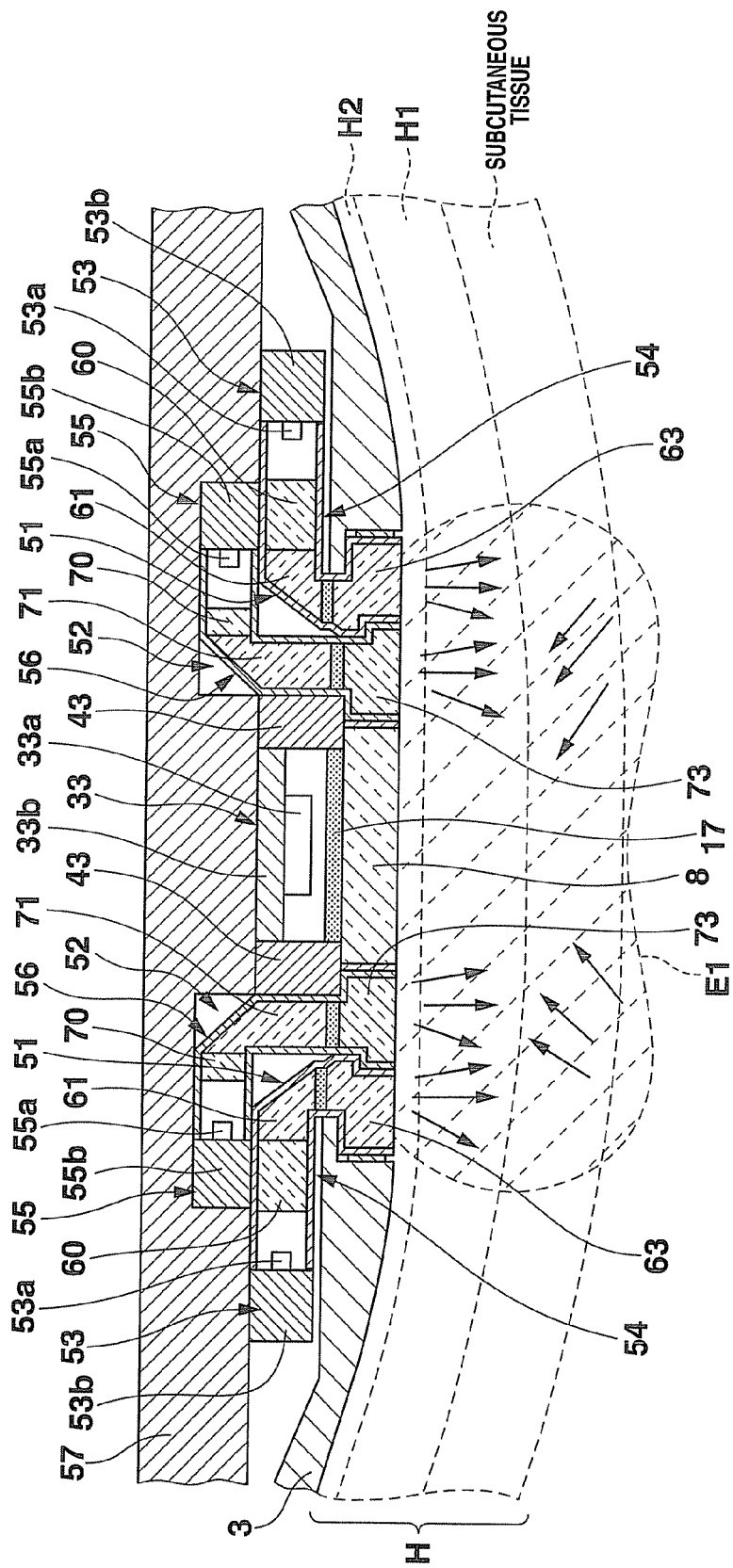
FIG. 24 is a cross-sectional view illustrating an irradiation state (irradiation area E1) of observation light when both first and second light emitting portions are made to simultaneously emit light while the back cover of the wristwatch illustrated in FIG. 19 contacts a skin of an arm.

As illustrated in FIGS. 21 and 24, the emitted observation light is taken in the first and second light guiding ring portions 60 and 70 from the incident surfaces 60*b* and 70*b* of the four directions in the first and second light guiding ring portions 60 and 70 of the first and second light guide units 54 and 56. The taken observation light is guided to the circular holes 60*a* and 70*a* of the central portions by the first and second light guiding ring portions 60 and 70 and is annularly discharged from the emission surfaces 60*c* and 70*c* of the first and second light guiding ring portions 60 and 70.

The observation light discharged from the first and second light guiding ring portions 60 and 70 is incident from the incident surfaces 61*a* and 71*a* of the first and second diffusion/reflection ring portions 61 and 71. The incident observation light is annularly guided along the first and second diffusion/reflection ring portions 61 and 71 while being diffused by the first and second diffusion/reflection ring portions 61 and 71, and is reflected to the emission surfaces 61*b* and 71*b* of the first and second diffusion/reflection ring portions 61 and 71 by the reflection surfaces 61*c* and 71*c* provided in the inner circumferential portions of the first and second diffusion/reflection ring portions 61 and 71.

The reflected observation light is discharged to the lower side toward the skin H from the emission surfaces 61*b* and 71*b* of the first and second diffusion/reflection ring portions 61 and 71. The observation light discharged from the first and second diffusion/reflection ring portions 61 and 71 is incident in the first and second diffusion ring portions 62 and 72 disposed on the lower sides of the first and second diffusion/reflection ring portions 61 and 71.

The incident observation light is sufficiently diffused to become uniform and discharged to the lower side, while being annularly guided by the first and second diffusion ring portions 62 and 72. The observation light uniformly discharged from the first and second diffusion ring portions 62 and 72 is incident in the first and second diffusion/irradiation ring portions 63 and 73 disposed on the lower sides of the first and second diffusion ring portions 62 and 72.

The observation light incident in the first and second diffusion/irradiation ring portions 63 and 73 is further diffused by the first and second diffusion/irradiation ring portions 63 and 73, and is annularly discharged as the uniform observation light from the bottom surfaces of the first and second diffusion/irradiation ring portions 63 and 73 contacting the skin H. The discharged observation light is uniformly irradiated onto the skin H of the arm over the wide range of the ring shape. As illustrated in FIG. 24, the irradiated observation light is incident in the epidermis H2 and the dermis H1 in the irradiation area E1 of the skin H.

At this time, even though the epidermis H2 contains the large amount of melanine pigment, the observation light is light of an infrared band of $\lambda p=940$ nm. For this reason, the amount of light absorbed by the melanine pigment is small and the light is securely incident in the dermis H1. Since the epidermis H2 has the layer thickness of about 0.1 mm to 0.2 mm, which is smaller than that of the dermis H1, most of the irradiated observation light transmits the epidermis H2 and is incident in the dermis H1 having the layer thickness of about 2 mm.

The observation light incident in the inner portion of the dermis H1 is uniformly irradiated over a wide area of a ring shape, as compared with the case where the observation light is spotlightingly irradiated onto a portion. For this reason, since the amount of hemoglobin that is a light absorbing substance in the dermis H1 in the irradiation area E1 increases, the large amount of observation light is absorbed in the dermis H1 and the amount of observation light that arrives at a subcutaneous tissue of the inner side (lower side in FIG. 24) of the dermis H1 decreases.

The observation light incident in the dermis H1 is absorbed and scattered by the biological tissue of the dermis H1, and a portion of the scattered light transmits the epidermis H2 again and is discharged from the surface of the epidermis H2. Even at this time, since the small amount of scattered light is absorbed by the melanine pigment, the scattered light securely transmits the epidermis H2 and is taken in the scattered light taking unit 8.

Since the scattered light taking unit 8 is formed of a material having a high refractive index, the scattered light taken by the scattered light taking unit 8 among the scattered light scattered by the biological tissue in the dermis H1 and the scattered light taken from the outer circumferential portion of the scattered light taking unit 8 can be incident in the light receiving unit 33 disposed on the side opposite to the skin H, from a front direction. Among the scattered light transmitted through the scattered light taking unit 8, light of a specific wavelength band of 900 nm or more is selected by the optical filter 17, the selected light of the specific wavelength band transmits the optical filter 17, and the transmitted light of the specific wavelength band is received by the light receiving element 33a of the light receiving unit 33 and is subjected to photoelectric conversion.

Figure 25:
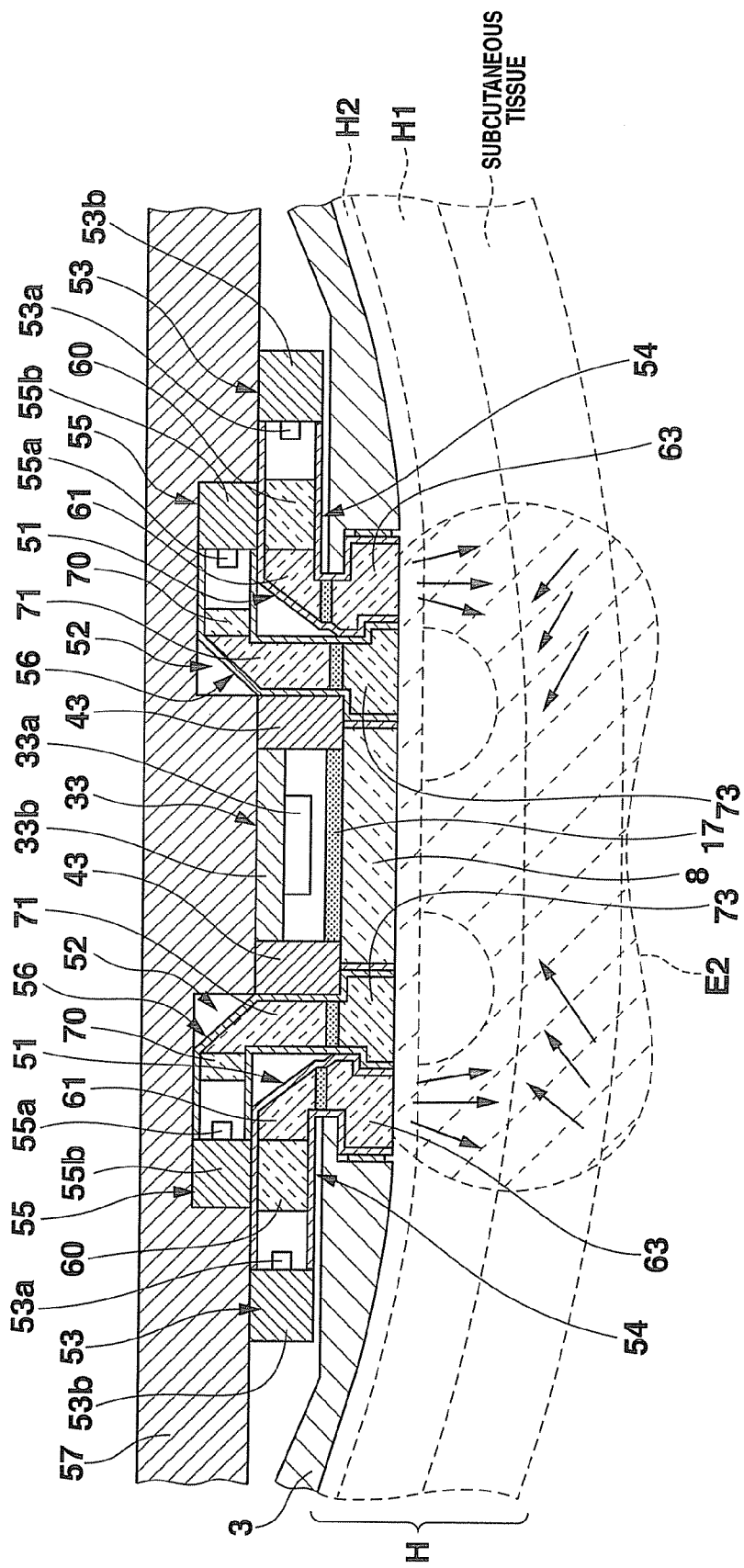
FIG. 25 is a cross-sectional view illustrating an irradiation state (irradiation area E2) of observation light when only the first light emitting portion is made to emit light after the irradiation state (irradiation area E1) of the observation light illustrated in FIG. 24.

When only the first light emitting portion 53 is driven by the first light emitting portion driving circuit 82 and only the first light emitting element 53a emits light, the light is annularly discharged as the observation light from the bottom surface of the first diffusion/irradiation ring portion 63 and is irradiated onto the irradiation area E2 of the skin H of the arm. As illustrated in FIG. 25, the irradiated observation light is scattered in the epidermis H2 and the dermis H1 in the irradiation area E2 of the skin H, taken by the scattered light taking unit 8, received by the light receiving element 33a of the light receiving unit 33, and subjected to photoelectric conversion.

Among the current signal subjected to the photoelectric conversion by the light receiving element 33a, the electric signal obtained when both the first and second light emitting elements 53a and 55a emit light and the electric signal obtained when only the first light emitting element 53a emits light are converted into a voltage signal by the I/V converting circuit 22, and the voltage signal is converted into a digital signal by the A/D converter of the CPU 80.

Among the converted digital signal, the electric signal obtained when both the first and second light emitting elements 53a and 55a emit light is stored in the RAM 85 as the first time-series data illustrated in FIG. 29A by the CPU 80, and the electric signal obtained when only the first light emitting element 53a emits light is stored in the RAM 85 as the second time-series data illustrated in FIG. 29B by the CPU 80.

Figure 26:
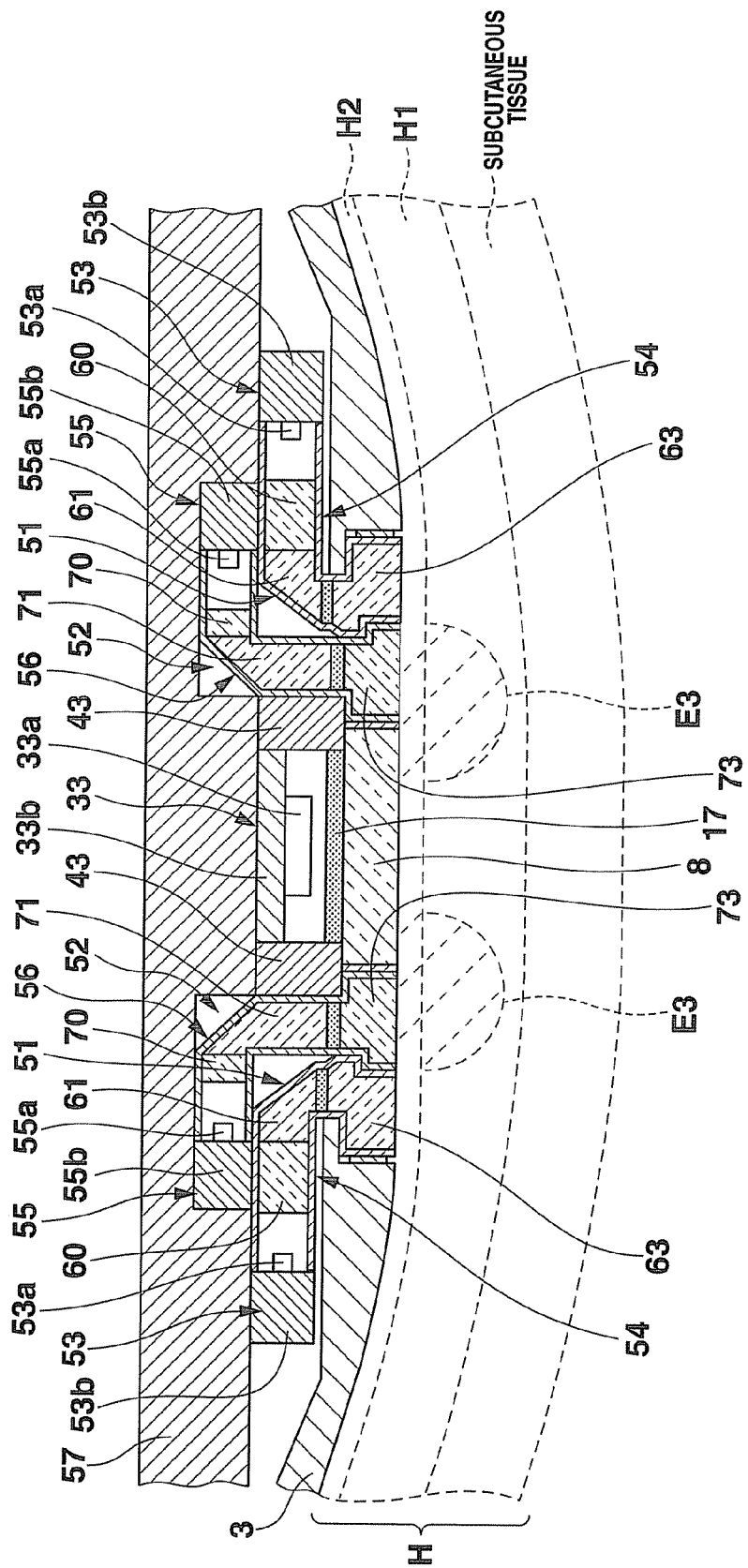
FIG. 26 is a cross-sectional view illustrating an estimated irradiation state (irradiation area E3) of observation light when biological information, such as a pulse wave, is optically measured after the irradiation state (irradiation area E2) of the observation light illustrated in FIG. 25.

The CPU 80 performs a frequency analysis on the first and second time-series data, operates the frequency-analyzed first and second time-series data, calculates data corresponding to the third time-series data corresponding to the irradiation area E3 illustrated in FIG. 26, estimates the calculated data corresponding to the third time-series data illustrated in FIG. 29C as the biological information such as the pulse wave, stores the estimated data in the RAM 85, and displays the data on the display unit 23.

Meanwhile, the outline of the operational principle of the biological information detecting apparatus 50 is as described above. According to the operational principle, absorbance with which hemoglobin in blood absorbs light greatly changes at about 600 nm, and the absorbance is very high at a wavelength shorter than 600 nm, as compared with a wavelength of 600 nm or more. This reason is as follows. The surface-side inner portion of the skin H consists essentially of the dermis H1 including the blood capillary corresponding to an observation object of the pulse wave and the epidermis H2 containing the melanine pigment of the surface side, and the observation light may be absorbed by the melanine pigment, if the large amount of melanine pigment is contained in the epidermis H2.

That is, the melanine pigment has extraordinarily high absorbance in a wavelength band from ultraviolet light to visible light. When the large amount of melanine pigment is contained in the epidermis H2 (for example, in the case of a person of a dark skin color), even though observation light having a wavelength of 600 nm or less is irradiated onto the skin, the observation light that reaches the dermis H1 including the blood capillary, repeats scattering and absorption in a tissue of the dermis H1, passes through the epidermis H2 again, and arrives at the light receiving element 33a is weak light and cannot be sufficiently received.

For this reason, if the light of the infrared band of 940 nm is observed and emitted by the first and second light emitting elements 53a and 55a, the amount of observation light absorbed by the melanine pigment contained in the epidermis H2 can be minimally suppressed and a biological tissue, such as a pulse wave, can be accurately measured. At this time, if the amount of light received in the light receiving element 33a when the observation light is emitted by both the first and second light emitting elements 53a and 55a and the amount of light received in the light receiving element 33a when the observation light is emitted by only the first light emitting element 53a are measured and the difference therebetween is calculated, the amount of light received in the irradiation area E3 that is an area where the measurement is difficult can be estimated. Thereby, the biological tissue, such as the pulse wave, can be further accurately measured.

As such, according to the biological information detecting apparatus 50, the same function and effect as those of the second embodiment can be achieved. The biological information detecting apparatus 50 comprises the first and second light emitting elements 53a and 55a, the first and second light guide members 54 and 56, the outer circumferential side light irradiation path 51 through which the observation light emitted from the first light emitting element 53a is annularly irradiated onto the skin H by the first light guide member 54, and the inner circumferential side light irradiation path 52 through which the observation light emitted from the second light emitting element 55a is annularly irradiated onto the skin H by the second light guide member 56. Therefore, the amount of light received in the light receiving element 33a when the observation light is emitted by both the first and second light emitting elements 53a and 55a and the amount of light received in the light receiving element 33a when the observation light is emitted by only the first light emitting element 53a can be measured.

For this reason, if the difference between the amount of light received in the light receiving element 33a when the observation light is emitted by both the first and second light emitting elements 53a and 55a and the amount of light received in the light receiving element 33a when the observation light is emitted by only the first light emitting element 53a is operated, the amount of light received in the irradiation area E3 where the measurement is difficult can be estimated. Thereby, the biological tissue, such as the pulse wave, can be further accurately measured.

That is, in the originally desired measurement area, as illustrated in FIG. 26, only the second light emitting element 55a may be made to emit observation light, the emitted observation light may be irradiated onto the skin H, and the scattered light that is irradiated and scattered in the skin H may be received by the light receiving element 33a. However, if only the amount of light received in the light receiving element 33a when the observation light is emitted by only the second light emitting element 55a is measured, an error due to an influence from the melanine pigment contained in the epidermis H2 or the external light is large, and the biological tissue, such as the pulse wave, cannot be accurately measured.

In this case, the inner circumferential side light irradiation path 52 causes the observation light to be annularly irradiated onto the skin H along the outer circumference of the scattered light taking unit 8, and the outer circumferential side light irradiation path 51 causes the observation light to be annularly irradiated onto the skin H along the outer circumference of the irradiation area E2 of the observation light irradiated by the inner circumferential side light irradiation path 52. Therefore, the annular irradiation area E1 when the observation light is emitted by the first and second light emitting elements 53a and 55a and irradiated onto the skin H can be sufficiently enlarged along the outer circumference of the scattered light taking unit 8, and the annular irradiation area E2 when the observation light is emitted by only the first light emitting element 53a and is irradiated onto the skin H can be made to be away from the outer circumference of the scattered light taking unit 8.

For this reason, if the amount of light received in the light receiving element 33a when the observation light is emitted by both the first and second light emitting elements 53a and 55a and the amount of light received in the light receiving element 33a when the observation light is emitted by only the first light emitting element 53a are measured and the difference therebetween is operated, the amount of light received in the irradiation area E3 where the measurement is difficult can be accurately estimated. Thereby, the biological tissue, such as the pulse wave, can be accurately measured.

Even in this case, if the observation light of the specific wavelength band of $\lambda p=940$ nm is emitted by the first and second light emitting elements 53a and 55a, the observation light can be annularly diffused in and irradiated onto the skin H by the first and second light guide members 54 and 56. Therefore, the observation light can be uniformly irradiated over the wide range of the skin H, and the scattered light of the observation light that is scattered in the skin H can be received by the light receiving element 33a of the light receiving unit 33 disposed to correspond to the central portion in the annular irradiation areas E1 and E2. As a result, the scattered light of the observation light can be efficiently and stably received by the light receiving element 33a.

For this reason, the observation light from the first and second light emitting elements 53a and 55a can be uniformly irradiated over the wide range of the skin H, and the outer circumferential side light irradiation path 51 and the inner circumferential side light irradiation path 52 through which the observation light from the first and second light emitting elements 53a and 55a is irradiated onto the skin H and the light reception path through which the scattered light of the observation light scattered in the skin H is received can be optically perfectly isolated by the first to sixth reflection layers 64 to 66 and 74 to 76 and the holder portion 43. Therefore, the scattered light of the observation light that is diffused in and irradiated onto the skin H can be efficiently and stably received by the light receiving element 33a. Thereby, a biological tissue, such as a pulse wave, can be accurately measured.

Since the first and second light emitting lights 53a and 55a are disposed in the plural places of the outer circumferential surfaces of the first and second light guiding ring members 54 and 56, for example, in the corner portions positioned in four directions of the 12 o'clock side, the 3 o'clock side, the 6 o'clock side, and the 9 o'clock side, respectively, the observation light of the sufficiently large amount can be discharged from the emission surfaces 60c and 70c of the first and second light guiding ring portions 60 and 70, and the observation light of the large amount can be discharged from the emission surfaces 61b and 71b of the first and second diffusion/reflection ring portions 61 and 71 to the skin H.

On the emission surfaces 61b and 71b of the first and second diffusion/reflection ring portions 61 and 71, the first and second diffusion ring portions 62 and 72 that take the observation light discharged from the emission surfaces 61b and 71b and uniformly diffuse the observation light while guiding the observation light along an annular shape are provided. Therefore, when the observation light diffused and reflected by the first and second diffusion/reflection ring portions 61 and 71 is taken by the first and second diffusion ring portions 62 and 72 and the taken observation light is discharged from the bottom surface, the observation light can be uniformly discharged along the annular shape without irregularity.

Since the optical filter 17 that transmits the light of the specific wavelength band is provided on the bottom surface corresponding to the incident surface of the light receiving element 33a, irradiation of the unnecessary light, such as the external light, onto the light receiving element 33a can be alleviated by the optical filter 17. Thereby, since only the scattered light of the observation light emitted from the first and second light emitting elements 53a and 55a and scattered in the skin H can be securely received by the light receiving element 33a, the biological tissue can be accurately measured and detection precision of the pulse wave of the human body can be enhanced.

In this case, since the light receiving element 33a has a spectral sensitivity characteristic of reacting with the light of the specific wavelength band of about 900 nm transmitted by the optical filter 17, only light of the specific wavelength band transmitted through the optical filter 17 can be accurately received and can be subjected to photoelectric conversion. At this time, the unnecessary light included in the external light such as the sunlight can be shielded by the optical filter 7 and the change of the light receiving element 33a due to the external light can be alleviated. Thereby, the biological tissue can be accurately measured and detection precision of the pulse wave of the human body can be enhanced.

In the wristwatch, since the biological information detecting apparatus 50 is provided in the back cover 3 in the wristwatch case 1, the wristwatch case 1 can be mounted on the arm and used. That is, if the wristwatch case 1 is mounted on the arm, since the back cover 3 contacts the skin H of the arm, a portion of the biological information detecting apparatus 50 that is exposed from the mounting hole 3b of the contacted back cover 3 can be contacted with the skin H. For this reason, the biological tissue can be measured anytime and anywhere, in a state where the wristwatch case 1 is mounted on the arm.

According to the biological information detecting method, the first and second light emitting elements 53a and 55a are made to simultaneously emit the observation light, the emitted observation light is irradiated onto the skin H by the outer circumferential side light irradiation path 51 and the inner circumferential side light irradiation path 52, the scattered light of the irradiated observation light in the skin H is taken by the scattered light taking unit 8, the taken scattered light is received by the light receiving element 33a, and the first biological information is detected. After that, only the first light emitting element 53a is made to emit the observation light, the observation light is irradiated onto the skin H by the outer circumferential side light irradiation path 51, the scattered light of the irradiated observation light in the skin H is taken by the scattered light taking unit 8, the taken scattered light is received by the light receiving element 33a, and the second biological information is detected. If the first and second biological information is operated and biological information unique to a measurer is calculated, the amount of light received in the irradiation area E3 where the measurement is difficult can be estimated. Thereby, the biological tissue unique to the measurer, such as the pulse wave, can be accurately measured.

That is, as illustrated in FIGS. 17 to 29, the first biological information detecting apparatus 50 that executes the second biological information detecting method comprises the first and second light emitting elements 53a and 55a that emit the observation light of the specific wavelength band to optically observe the skin tissue of the human body, the annular first and second light guide members 54 and 56 that guide the observation light emitted from the first and second light emitting elements 53a and 55a and annularly diffuse and irradiate the observation light with respect to the skin H, the scattered light taking unit 8 that is disposed to contact the skin H at the position of the central portion surrounded by the annular irradiation areas E1 and E2 where the observation light is annularly irradiated by the annular first and second light guide members 54 and 56, and takes the scattered light scattered in the skin H, and the light receiving element 33a that is disposed on the side opposite to the skin H in the scattered light taking unit 8 and receives the scattered light taken by the scattered light taking unit 8.

In the biological information detecting apparatus 50 having the above configuration, the biological information detecting method according to the fourth embodiment uses the outer circumferential side light irradiation path 51 through which the observation light emitted from the first light emitting element 53a is annularly irradiated onto the skin H in the place apart from the outer circumference of the scattered light taking unit 8 by the first light guide member 54, and the inner circumferential side light irradiation path 52 through which the observation light emitted from the second light emitting element 55a is annularly irradiated onto the skin H in the place between the outer circumference of the scattered light taking unit and the irradiation area of the observation light based on the outer circumferential side light irradiation path by the second light guide member 56, as the light irradiation path along which the observation light is annularly irradiated onto the skin H.

Figure 31:
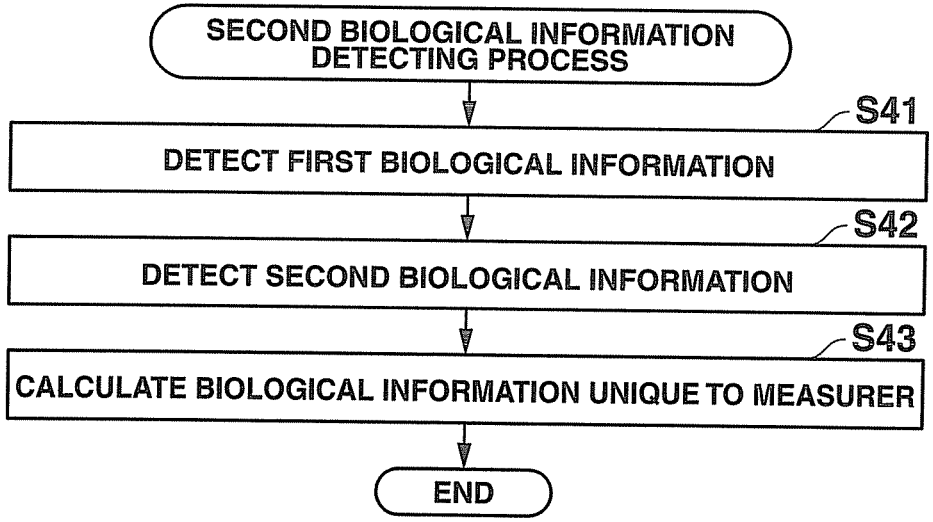
FIG. 31 is a flow chart illustrating an optical biological information detecting method according to a second embodiment of the present invention.

As illustrated in FIG. 31, the biological information detecting method according to the fourth embodiment comprises a first measuring step S41 of causing the first and second light emitting elements 53a and 55a to simultaneously emit light, irradiating the observation light onto the skin H by the outer circumferential side light irradiation path 51 and the inner circumferential side light irradiation path 52, taking the scattered light of the irradiated observation light in the skin H by the scattered light taking unit 8, receiving the taken scattered light by the light receiving element 33a, and detecting the first biological information based on the received scattered light, a second measuring step S42 of causing only the first light emitting element 53a to emit light, irradiating the observation light onto the skin H by the outer circumferential side light irradiation path 51, taking the scattered light of the irradiated observation light in the skin H by the scattered light taking unit 8, receiving the taken scattered light by the light receiving element 33a, and detecting the second biological information based on the received scattered light, and an operating step S43 of operating the first biological information detected by the first measuring step S41 and the second biological information detected by the second measuring step S42 and calculating biological information unique to a measurer.

According to the biological information detecting method having the above configuration, the biological information can be accurately and easily detected based on the received scattered light, similar to the cases of the above-described biological information detecting methods.

In the fourth embodiment, the case where the first and second light guide members 54 and 56 comprise the first and second light guiding ring portions 60 and 70, the first and second diffusion/reflection ring portions 61 and 71, the first and second diffusion ring portions 62 and 72, and the first and second diffusion/irradiation ring portions 63 and 73 has been described, but the present invention is not limited thereto. For example, as described in the third embodiment, the first and second light guide members 54 and 56 may be configured to comprise only the first and second light guiding ring portions 60 and 70 and the first and second diffusion/reflection ring portions 61 and 71. In this case, the scattered light taking unit 8 does not need to be provided. Even in this configuration, the same function and effect as those of the fourth embodiment can be achieved and the size of the apparatus can be further decreased as compared with the fourth embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical biological information detecting apparatus, comprising:
  a light emitting unit which emits observation light of a specific wavelength band to optically observe a desired portion of a tissue of a skin of a human body;
  an annular light guide unit which is adapted to contact a desired area of a surface of the skin corresponding to the desired portion of the tissue of the skin, which guides the observation light to the desired area of the surface of the skin, and which annularly irradiates the observation light onto the desired area of the surface of the skin; and
  a light receiving unit which is disposed at a position surrounded by the annular light guide unit, and which receives scattered light scattered by the desired portion of the tissue of the skin after the observation light is annularly irradiated onto the desired area of the surface of the skin by the annular light guide unit, the light receiving unit including an optical filter, a light receiving element and a holder portion which has a light shielding function and in which the light receiving element and the optical filter are disposed to adapt the optical filter to contact a position of the surface of the skin surrounded by the annular light guide unit, and the holder portion shielding light excluding the scattered light toward the optical filter.

2. The optical biological information detecting apparatus according to claim 1, wherein
  the annular light guide unit comprises:
  a light guiding ring portion which comprises an outer circumferential surface and an inner circumferential surface defining a circular hole, the outer circumferential surface being provided with an incident surface on which the observation light is incident from the light emitting unit, and the inner circumferential surface being provided with an emission surface to emit the observation light incident in the incident surface; and a diffusion/reflection ring portion which is disposed in the circular hole of the light guiding ring portion, which comprises an outer circumferential surface facing the inner circumferential surface of the circular hole and a skin surface facing surface facing the desired area of the surface of the skin, the outer circumferential surface being provided with an incident surface on which the observation light emitted from the emission surface of the light guiding ring portion is incident, the skin surface facing surface being provided with an annular emission surface to annularly diffuse the observation light incident in the incident surface and to annularly irradiate the diffused observation light onto the desired area of the surface of the skin, and which guides the observation light incident in the incident surface to the annular emission surface by reflection.

3. The optical biological information detecting apparatus according to claim 2, wherein each of the light guiding ring portion and the diffusion/reflection ring portion has the same predetermined height as to each other in a direction crossing the surface of the skin and are disposed in a direction along the surface of the skin without generating a step in the crossing direction, and the light emitting unit and the light receiving unit are disposed within a range of the predetermined height.

4. The optical biological information detecting apparatus according to claim 2, further comprising:

a diffusion/irradiation ring portion which is provided to correspond to the annular emission surface of the skin surface facing surface of the diffusion/reflection ring portion and to face the desired area of the surface of the skin, which transmits the annularly diffused observation light emitted from the annular emission surface of the diffusion/reflection ring portion, and which annularly diffuses and irradiates the annularly diffused observation light toward the desired area of the surface of the skin.

5. The optical biological information detecting apparatus according to claim 1, wherein the observation light emitted from the light emitting unit is a light of an infrared band of 800 nm or more which has a low absorbance to melanine pigment contained in the skin.

6. The optical biological information detecting apparatus according to claim 1, wherein the annular light guide unit comprises a reflection layer that reflects the observation light emitted from the light emitting unit to the desired area of the surface of the skin, and the reflection layer prevents the scattered light until the scattered light is received by the light receiving unit after being scattered in the desired portion of the tissue of the skin from being mixed with the observation light in the light guide unit.

7. The optical biological information detecting apparatus according to claim 1, wherein:

the optical filter transmits only light of a specific wavelength band of 800 nm or more among the scattered light toward the light receiving unit.

8. The optical biological information detecting apparatus according to claim 1, wherein the light receiving unit has a spectral sensitivity characteristic which reacts with only light of a specific wavelength band among the scattered light toward the light receiving unit.

9. The optical biological information detecting apparatus according to claim 1, wherein the optical biological information detecting apparatus is combined with a wristwatch which comprises a time piece module and a body case including an internal space to store the time piece module and a back cover, the light emitting unit, the light guide unit, and the light receiving unit are provided in the internal space of the body case of the wristwatch, and the back cover is provided with an observation light/scattered light transmitting structure which transmits the observation light annularly irradiated from the light guide unit to the desired area of the surface of the skin and which transmits the scattered light scattered by the desired portion of the tissue of the skin after the observation light is annularly irradiated onto the desired area of the surface of the skin by the annular light guide unit.

* * * * *